(12) United States Patent
Pedersen et al.

(10) Patent No.: US 9,217,039 B2
(45) Date of Patent: *Dec. 22, 2015

(54) ANTI-HER3 ANTIBODIES AND COMPOSITIONS

(75) Inventors: Mikkel Wandahl Pedersen, Alleroed (DK); Helle Jacobsen, Virum (DK); Klaus Koefoed, København S (DK)

(73) Assignee: SYMPHOGEN A/S, Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/882,807

(22) PCT Filed: Oct. 31, 2011

(86) PCT No.: PCT/IB2011/054835
§ 371 (c)(1),
(2), (4) Date: Jun. 13, 2013

(87) PCT Pub. No.: WO2012/059858
PCT Pub. Date: May 10, 2012

(65) Prior Publication Data
US 2013/0287684 A1 Oct. 31, 2013

Related U.S. Application Data

(60) Provisional application No. 61/531,407, filed on Sep. 6, 2011, provisional application No. 61/408,782, filed on Nov. 1, 2010.

(30) Foreign Application Priority Data

Nov. 2, 2010 (DK) .................................. 2010 00988
Sep. 5, 2011 (DK) .................................. 2011 00672

(51) Int. Cl.
| | | |
|---|---|---|
| *A61K 39/395* | (2006.01) |
| *C07K 16/40* | (2006.01) |
| *C07K 16/28* | (2006.01) |
| *C07K 16/32* | (2006.01) |
| *A61K 39/00* | (2006.01) |

(52) U.S. Cl.
CPC ............. *C07K 16/40* (2013.01); *A61K 39/3955* (2013.01); *C07K 16/2863* (2013.01); *C07K 16/32* (2013.01); *A61K 2039/505* (2013.01); *A61K 2039/507* (2013.01); *C07K 2317/24* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 5,968,511 A | 10/1999 | Akita et al. |
| 7,285,649 B2 * | 10/2007 | Akita et al. .................. 536/23.1 |
| 2005/0136494 A1 | 6/2005 | Akita et al. |
| 2006/0121044 A1 | 6/2006 | Amler et al. |
| 2010/0056761 A1 * | 3/2010 | Schoeberl et al. ......... 530/387.7 |
| 2010/0255010 A1 | 10/2010 | Fuh et al. |
| 2010/0256340 A1 | 10/2010 | Brinkmann et al. |

FOREIGN PATENT DOCUMENTS

| WO | WO9735885 | 10/1997 |
| WO | WO0177342 | 10/2001 |
| WO | WO03013602 | 2/2003 |
| WO | WO2006033700 | 3/2006 |
| WO | WO 2007/077028 | 7/2007 |
| WO | WO 2008/100624 | * 8/2008 |
| WO | WO-2008100624 | 8/2008 |
| WO | WO2010019952 | 2/2010 |
| WO | WO-2010022736 | 3/2010 |
| WO | WO2010040356 | 4/2010 |
| WO | WO2010108127 | 9/2010 |
| WO | WO-2010115552 | 10/2010 |
| WO | WO2010127181 | 11/2010 |
| WO | WO-2011003557 | 1/2011 |
| WO | WO-2011022727 | 2/2011 |
| WO | WO2011044311 | 4/2011 |
| WO | WO2011060206 | 5/2011 |
| WO | WO-2011136911 | 11/2011 |
| WO | WO-2012022814 | 2/2012 |
| WO | WO-2012059858 | 5/2012 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Schoeberl et al., "An ErbB3 antibody, MM-121, is active in cancers with ligand-dependent activation," Cancer Research 70(6):2845-2494 (2010).
Lou, Driving Cancer Through ErbB3, SciBX, 6(22):1-4 (2013).
PCT International Application No. PCT/IB2011/054835, International Search Report, Feb. 22, 2012.
Franklin et al., "Insights into ErbB signaling from the structure of the ErbB2-pertuzumab complex," Cancer Cell 5(4):317-328 (2004).
Schaefer et al., "A Two-in-One Antibody against HER3 and EGFR Has Superior Inhibitory Activity Compared with Monospecific Antibodies," Cancer Cell 20:472-486 (2011).
Vlacich et al., "Resistance to EGFR-Targeted Therapy: A Family Affair," Cancer Cell 20:423-425 (2011).
Wimmer et al., "HER3 Expression in Cutaneous Tumors," Anticancer Res 28:973-980 (2008).

* cited by examiner

*Primary Examiner* — Laura B Goddard

(74) *Attorney, Agent, or Firm* — Ropes & Gray LLP; Z. Ying Li; Ryan Murphey

(57) ABSTRACT

The present invention relates to novel therapeutic recombinant antibodies directed against HER3 (ErbB3), as well as compositions comprising mixtures of at least two of said recombinant anti-HER3 antibodies, and use of the antibodies and antibody compositions for treatment of cancer.

14 Claims, 21 Drawing Sheets

Figure 33

| | Domain I | | | | | Epitope bin III | Domain I / Murine Her3 | | Domain I / II | |
|---|---|---|---|---|---|---|---|---|---|---|
| | Epitope bin I | | | Epitope bin II | | | Epitope bin IV | | Epitope bin V | |
| | 4785 | 4935 | 5143 | 5082 | 4889 | 5038 | 5101 | 5106 | 5144 | 5259 |
| 4785 | 96 | 97 | 98 | 8 | -1 | 3 | 1 | 1 | 0 | 0 |
| 4935 | 96 | 97 | 99 | 5 | 0 | 3 | 0 | 0 | 0 | -1 |
| 5143 | 93 | 95 | 97 | 62 | -3 | -1 | -1 | -1 | -1 | -4 |
| 5082 | 23 | 5 | 63 | 99 | 96 | -1 | -1 | 0 | 0 | 0 |
| 4889 | 23 | 3 | 21 | 99 | 98 | 0 | 0 | 1 | 2 | 1 |
| 5038 | 0 | 5 | 0 | 0 | -1 | 96 | 1 | 1 | 0 | 0 |
| 5101 | 30 | 28 | 27 | 28 | 30 | 28 | 92 | 90 | 28 | 24 |
| 5106 | 6 | 6 | 8 | 8 | 1 | 7 | 93 | 91 | 8 | 2 |
| 5144 | -4 | -1 | -8 | 14 | 9 | -8 | 6 | 7 | 81 | 80 |
| 5259 | -4 | -1 | -5 | 15 | 10 | -5 | 5 | 9 | 84 | 84 |

ANTI-HER3 ANTIBODIES AND COMPOSITIONS

This application is a United States National Stage Application under 35 U.S.C. §371 of International Application PCT/IB2011/054835, filed Oct. 31, 2011 (pending), which claims priority to and the benefit of U.S. Provisional Application 61/531,407, filed Sep. 6, 2011, and U.S. Provisional Application 61/408,782, filed Nov. 1, 2010, Danish Application No. PA 2010 00988, filed Nov. 1, 2010 (expired) and Danish Application No. PA 2011 00672, filed Sep. 5, 2011 (expired). The entire disclosure of each of the above applications is hereby incorporated by reference in its entirety.

The instant application contains a Sequence Listing that has been submitted in ASCII format via EFS-Web and is hereby incorporated by reference in its entirety. Said ASCII file, created on Apr. 30, 2013, is named 110285-0042-301-Sequence-Listing.txt and is 67,766 bytes in size.

FIELD OF THE INVENTION

The present invention relates to novel recombinant antibodies targeting the HER3 receptor and compositions comprising two or more of these antibodies for use in human cancer therapy.

BACKGROUND OF THE INVENTION

The EGFR Receptor Family

The epidermal growth factor receptor (EGFR) family (also known as the ErbB family) is a subgroup of the receptor tyrosine kinases (RTKs) and consists of four members: HER1/EGFR/ErbB, HER2/ErbB2, HER3/ErbB3 and HER4/ErbB4. The members of the EGFR family are closely related single-chain modular glycoproteins with an extracellular ligand binding region, a single transmembrane domain and an intracellular tyrosine kinase (reviewed in Ferguson (2008) *Annu Rev Biophys.* 37: 353-373). In normal physiological settings the ErbB family regulates key events in coordination of cell growth, differentiation and migration (Citri et al. (2006) *Nat Rev Mol Cell Biol.* 7: 505-516). EGFR, HER2 and HER3 are believed to play crucial roles in the malignant transformation of normal cells and in the continued growth of cancer cells (pro-survival pathway). EGFR and HER2 have been found to be overexpressed by many epithelial cancers (Slamon et al. (1987) *Science*, 235: 177-182; Arteaga (2002) *Oncologist* 7 Suppl 4: 31-39; Bodey et al. (1997) *Anticancer Res.* 17: 1319-1330; Rajkumar et al. (1996) *J. Pathol.* 179: 381-385). Overexpression of EGFR and HER2 has furthermore been linked to disease progression, reduced survival, poor response and chemotherapy resistance in several human epithelial cancers (Slamon et al. (1987) supra; Baselga et al. (2002) *Oncologist* 7 Suppl 4: 2-8).

HER3 Structure

The third member of the ErbB family, known as human epidermal growth factor receptor 3 (HER3, ErbB3) was identified in 1989 by Kraus et al. (*Proc Natl Acad Sci USA* 1989; 86: 9193-9197). The HER3 gene encodes a protein of 1342 amino acids with striking structural similarities to EGFR and HER2. Features such as overall size, four extracellular subdomains (I-IV) with two cysteine clusters (domains II and IV), and a tyrosine kinase domain show structural similarities to EGFR and HER2 (Cho and Leahy (2002) *Science*, 297: 1330-1333). The tyrosine kinase domain of HER3 shows 59% sequence homology to the tyrosine kinase domain of EGFR (Brennan et al. (2000) *Oncogene*, 19: 6093-6101).

Regulation of HER3 Activation

Neu differentiation factor (NDF), heregulin (HRG) and neuregulin 1 (NRG1) are synonyms for the glycoprotein which is a ligand for HER3 (Peles et al. (1992) *Cell*, 69: 205-216; Wen et al. (1992) *Cell*, 69: 559-572). At least 15 isoforms of the NRG1 protein have been identified. The isoforms are produced from the single NRG1 gene through alternative splicing and multiple promoters (Falls et al. (2003) *Exp Cell Res*, 284: 14-30). Three structural characteristics apply for the functional differences of the isoforms. These structural characteristics are the type of EGF-like domain (α or β), the N-terminal sequence (type I, II or III) and whether the isoform is initially synthesized as a transmembrane or non-membrane protein (Falls et al. (2003) supra). The type I sub-group of NRG1 isoforms have a unique N-terminal sequence followed by an immunoglobulin-like domain and then an EGF-like domain. Type II variants contain an N-terminal kringle-like sequence, the immunoglobulin domain and the EGF-like domain. The type III variants contain an N-terminal hydrophobic domain within a cysteine-rich region, omit the immunoglobulin domain and then continue into the EGF-like domain and various downstream alternative exons. Downstream from the EGF-like domain the NRG1 isoform may contain a linker sequence, a transmembrane domain and a cytoplasmic tail (Falls et al. (2003) supra). Some of the NRG1 isoforms are subject to glycosylation in the spacer region between the immunoglobulin-like domain and the EGF-like domain (Hayes et al. (2008) *J Mammary Gland Biol Neoplasia*, 13: 205-214).

As is the case for EGFR, HER3 exists in a tethered conformation and in an extended conformation. In the tethered conformation the dimerization arm is buried by interactions with domain IV, leaving domains I and III too far apart for efficient ligand binding (Cho and Leahy et al. (2002) supra). Ligand binding to the extracellular domains I and III occurs in the extended conformation of HER3 and leads to heterodimerization with other members of the ErbB family (or other RTK members, e.g. MET), the extended and ligand-bound HER3 molecule preferentially heterodimerizing with HER2 (Pinkas-Kramarski et al. (1996) *EMBO J*, 15: 2452-2467). No HER3 homodimers are formed upon ligand binding (Ferguson et al. (2000) *EMBO J*, 19: 4632-4643).

In contrast to EGFR and HER2, the tyrosine kinase of HER3 has impaired catalytic activity, insufficient for any detectable biological response (Pinkas-Kramarski et al. (1996) supra; Guy et al. (1994) *Proc Natl Aced Sci USA*, 91: 8132-8136). Two amino acid residues which are highly conserved in the catalytic domains of protein kinases (Hanks et al. (1988) *Science*, 241: 42-52) are altered in the catalytic domain of HER3. These are the substitution of aspargine for aspartic acid at residue 815 and substitution of histamine for glutamate at residue 740. The two amino acid substitutions may be the reason why HER3 lacks catalytic activity of its tyrosine kinase domain (Plowman et al. (1990) *Proc Natl Acad Sci USA*, 87: 4905-4909). Because of the impaired intrinsic kinase activity of HER3, the receptor needs to heterodimerize with another ErbB family member in order to respond to its own ligand binding (Berger et al. (2004) *FEBS Lett*, 569: 332-336).

Termination of HER3 Signaling

Little is known about endocytosis of HER3. Moreover, different studies have suggested that HER3 is endocytosis impaired to the same extent as HER2 (Baulida et al. (1996) *J Biol Chem*, 271: 5251-5257). In agreement with this the HER3-NRG1 complex was found to be internalized less efficiently and slower than the EGFR-EGF complex, supporting that HER3 is not endocytosed as efficiently as EGFR (Baulida et al. (1997) *Exp Cell Res*, 232: 167-172; Waterman et al. (1999) *EMBO J*, 18: 3348-3358). However, when the C-terminal tail of EGFR was replaced with the C-terminal tail of HER3, EGFR became endocytosis impaired, suggesting that a region in the C-terminus of HER3 protects the receptor against internalization (Waterman et al. (1999) supra). It has also been suggested that NRG1 does not efficiently target HER3 to degradation due to the dissociation of the ligand-receptor complexes in endosomes, as it is observed when EGF is activated by TGFα (Waterman et al. (1999) supra).

Expression and Physiological Role of HER3

HER3 has like EGFR and HER2 been shown to be of importance in the mammary gland development (Schroeder et al. (1998) *Cell Growth Differ*, 9: 451-464). While EGFR and HER2 are highly expressed and co-localized in the pubscent mouse mammary gland, HER3 is only expressed at low levels in postpubscent mammary glands from virgin mice, but is expressed at higher levels during pregnancy and lactation (Schroeder et al. (1998) supra). The higher expression levels of HER3 during pregnancy and lactation implies the importance of HER3 in the later stages of mammary gland development and differentiation (Jackson-Fisher et al. (2008) *Breast Cancer Res*, 10: R96). Studies with HER3-deficient mice further indicated the regulatory role of HER3 in morphogenesis of mammary epithelium through the PI3K/AKT signaling pathway (Jackson-Fisher et al. (2008) supra). Other studies showed high levels of HER3 expression by ductal epithelial cells in rats by day 14-16 of pregnancy, also demonstrating the regulatory role of HER3 in morphogenesis of mammary epithelium (Darcy et al. (2000) *J Histochem Cytochem*, 48: 63-80).

Targeted knockout of the HER3 gene in mice resulted in embryonic lethality at day 13.5 due to underdeveloped cardiac valves which were unable to support proper cardiac function due to blood reflux (Erickson et al. (1997) *Development*, 124: 4999-5011). Other defects include abnormalities in brain development, especially in the midbrain region including the cerebellum, and severe defects in Schwann cells of peripheral axons of sensory and motor neurons (Erickson et al. (1997) supra; Riethmacher et al. (1997) *Nature*, 389: 725-730).

In vitro studies have also implicated HER3, in combination with HER2, in the development of keratinocytes (Marikovsky et al. (1995) *Oncogene*, 10: 1403-1411), Schwann cell precursors (Syroid et al. (1996) *Proc Natl Aced Sci USA*, 93: 9229-9234), oligodendrocytes (Vartanian et al. (1997) *J Cell Biol*, 137: 211-220) and the neuromuscular synapse (Zhu et al. (1995) *EMBO J*, 14: 5842-5848).

The tissue distribution of HER3 is not much different from EGFR (www.proteinatlas.org). Despite the impaired kinase activity of HER3, the receptor plays an essential role in the ErbB network through the PI3K/AKT signaling (Citri et al. (2003) *Exp Cell Res*, 284: 54-65). Due to the requirement of heterodimerization for initiation of signaling, the physiological role of HER3 may overall resemble those identified for EGFR and HER2. The precise role of HER3 in the human adults is unknown, however, due to the embryonic lethality of HER3 knockout in mice and the sparse data on HER3 inhibition.

HER3 and Cancer

HER3 is unique in its ability to channel ErbB signaling to the PI3K/AKT signaling pathway, which favors tumor growth and progression (Prigent et al. (1994) *EMBO J*, 13: 2831-2841). The critical role of HER3 in regulation of tumor growth is also supported by the observation that HER2 overexpression in human breast cancer often is associated with higher levels of HER3 expression (Naidu et al. (1998) *Br J Cancer*, 78: 1385-1390). Moreover, overexpression of HRG results in increased transformation and tumorigenicity (Atlas et al. (2003) *Mol Cancer Res*, 1: 165-175), while blockade of NRG inhibits tumorigenicity and metastasis (Tsai et al. (2003) *Oncogene*, 22: 761-768), indicating the importance of the presence of a HER3 ligand for cancer development.

The presence of HER2 homodimers on the cell surface and thereby exaggeration of HER2 signaling causes transformation of epithelial cells (reviewed in Yarden and Sliwkowski (2001) *Nat Rev Mol Cell Biol*, 2: 127-137). However the HER2-HER3 dimer has the ability to induce signal transduction through both the mitogen-activated protein kinase (MAPK) and the AKT pathway. Activation of both the MAPK pathway and the AKT pathway implies the additional oncogenic potential of the HER2-HER3 heterodimer compared to the HER2 homodimer (reviewed in Citri et al. (2003) supra).

High expression of HER3 is found in many of the same tumor types that overexpress HER2, including bladder and colorectal cancer in addition to breast cancer (Bodey et al. (1997) *Anticancer Res*, 17: 1319-1330; Rajkumar et al. (1996) *J Pathol*, 179: 381-385; Lemoine et al. (1992) *BrJ Cancer*, 66: 1116-1121; Maurer et al. (1998) *Hum Pathol*, 29: 771-777). While more studies are needed to establish the association between HER3 overexpression and clinical outcome, the clinical indications support the results from in vitro studies that neither HER2 nor HER3 can be considered as stand-alone receptors in relation to cancer.

Anti-HER3 Antibodies

A number of anti-HER3 antibodies have been described in the literature. See, for example, WO 2011/060206, WO 2011/044311, WO 2011/022727, WO 2010/127181, WO 2008/100624, WO 2007/077028, WO 03/013602 and WO 97/35885.

AMG 888 (Amgen/Daiichi Sankyo) is a fully human monoclonal antibody that is said to inhibit human HER3 oncogenic signaling. AMG 888 is currently being investigated in clinical trials for treatment of cancer.

MM-121 (Merrimack Pharmaceuticals) is an anti-HER3 antibody that is said to block heregulin binding to and hence activation of HER3; see WO 2010/019952 and Schoeberl et al., *Cancer Res.* 70(6):2485-94, March 2010. MM-121 is also currently being investigated in clinical trials for treatment of cancer.

Pertuzumab is an anti-HER2 antibody that functions as a HER dimerization inhibitor which inhibits dimerization of HER2 to HER3 and the other EGFR receptors. Franklin et al. (*Cancer Cell* 2004, 5(4):317-28) disclose that pertuzumab binds HER2 near the center of domain II, sterically blocking a binding pocket necessary for HER2-HER3 heterodimerization and signaling. The amino acid sequence of pertuzumab is disclosed in WO 2006/033700 and US 2006/0121044 A1.

In spite of the fact that certain anti-HER3 antibodies are known and in some cases being investigated in clinical trials, no anti-HER3 antibodies are currently approved for therapeutic use. In view of the critical role of HER3 in regulation of tumor growth as outlined above, there is therefore a need for new antibodies that target the HER3 receptor as well as mixtures of such anti-HER3 antibodies.

SUMMARY OF THE INVENTION

The present invention is directed to novel recombinant antibodies targeting the HER3 receptor as well as compositions comprising two or more of these antibodies and use of the antibodies and compositions for human cancer therapy, e.g. for the treatment of breast cancer, ovarian cancer, gastric cancer and other cancers that express or overexpress HER3, or that have a signature of HER3 pathway activation (e.g. NSCLC, glioblastoma). Compared to the currently available treatments for such cancers, including available monoclonal antibodies directed against other receptors of the EGFR family, it is contemplated that the antibodies of the invention may provide a superior clinical response either alone or, preferably, in a composition comprising two or more such antibodies, and optionally in combination with other treatments such as chemotherapy.

In one aspect, the invention relates to novel recombinant anti-HER3 antibodies based on the antibodies referred to herein as antibodies 4785, 4889, 4935, 5038, 5082, 5101, 5106, 5143, 5144 and 5259, as well as humanized and/or affinity matured variants thereof. In one embodiment, this aspect of the invention relates to a recombinant anti-HER3 antibody molecule comprising the heavy chain CDR3 sequence of any one of the antibodies referred to herein as antibodies 4785, 4889, 4935, 5038, 5082, 5101, 5106, 5143, 5144 and 5259.

Further embodiments of this aspect of the invention include: a recombinant anti-HER3 antibody molecule comprising the heavy chain CDR3 sequence and the light chain CDR3 sequence of any one of antibodies 4785, 4889, 4935, 5038, 5082, 5101, 5106, 5143, 5144 and 5259, and which competes for binding with said antibody; a recombinant anti-HER3 antibody molecule comprising the heavy chain CDR1, CDR2 and CDR3 sequences and light chain CDR1, CDR2 and CDR3 sequences of any one of these antibodies; and a recombinant anti-HER3 antibody comprising the heavy chain variable region sequence and the light chain variable region sequence of any one of these antibodies, or comprising a heavy chain variable region sequence and a light chain variable region sequence each having at least 90% sequence identity, preferably at least 95% sequence identity, such as at least 96%, at least 97%, at least 98% or at least 99% sequence identity, with the heavy chain variable region and light chain variable region sequences, respectively, of any one of these antibodies, and which competes for binding with said antibody.

Another aspect of the invention relates to a recombinant antibody composition, comprising at least first and second recombinant anti-HER3 antibodies, wherein the first and second antibodies bind distinct epitopes of HER3, and wherein one or both of the first and second antibodies are selected from the group of antibodies outlined above.

A further aspect of the invention relates to an immunoconjugate comprising a recombinant anti-HER3 antibody of the invention conjugated to an anti-cancer agent. A related aspect relates to compositions comprising at least first and second recombinant anti-HER3 antibodies of the invention, wherein at least one anti-HER3 antibody in said composition is an immunoconjugate.

A further aspect of the invention relates to a nucleic acid molecule having a nucleotide sequence that encodes an anti-HER3 antibody of the invention, as well as expression vectors comprising such a polynucleotide and host cells that have been transfected with such an expression vector.

A still further aspect of the invention relates to methods for producing antibodies and polyclonal antibody compositions of the invention.

A still further aspect of the invention relates to methods for treating a disease in a human or animal subject, in particular treatment of cancer in humans, by administering an anti-HER3 antibody or composition of the invention to said subject. A related aspect is the use of one or more anti-HER3 antibodies of the invention for preparation of a medicament for use in treating a disease in a human or animal, in particular for the treatment of cancer in humans.

A still further aspect of the invention relates to a method for inducing internalization of HER3 on the surface of cells that express or overexpress HER3, the method comprising contacting the cells with a recombinant anti-HER3 antibody or immunoconjugate or a recombinant anti-HER3 antibody composition of the invention.

Additional aspects of the invention and particular embodiments will be apparent from the description and examples below.

DRAWING DESCRIPTION

FIG. 33 shows a table with the results of epitope binning of anti-HER3 antibodies by antibody cross-competition analysis.

DETAILED DESCRIPTION OF THE INVENTION

Definitions

Figure 1:
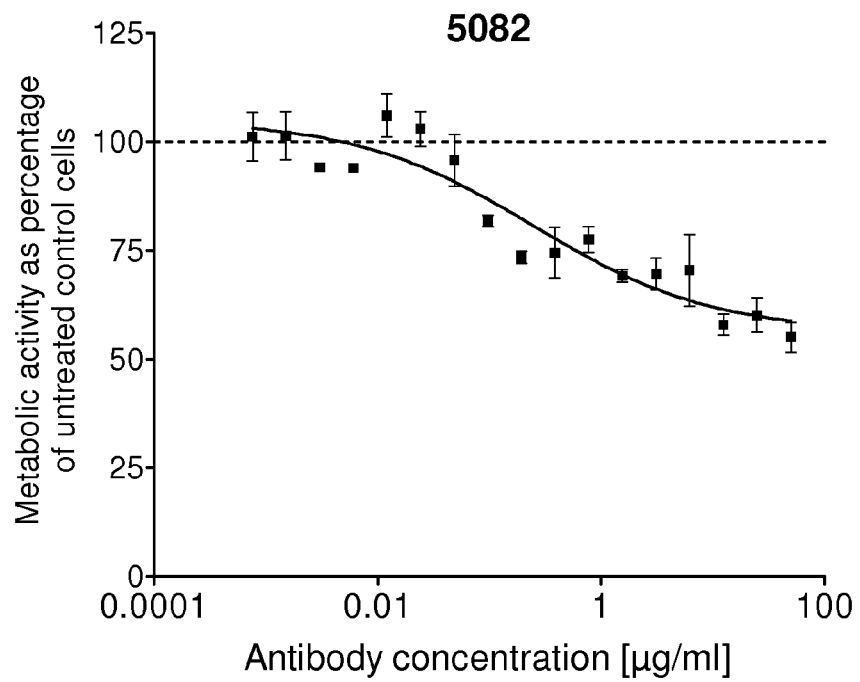
FIGS. 1-10 show the metabolic activity of MDA-MB-175 cells treated with different concentrations of the indicated anti-HER3 antibodies for 96 hours.
Figure 2:
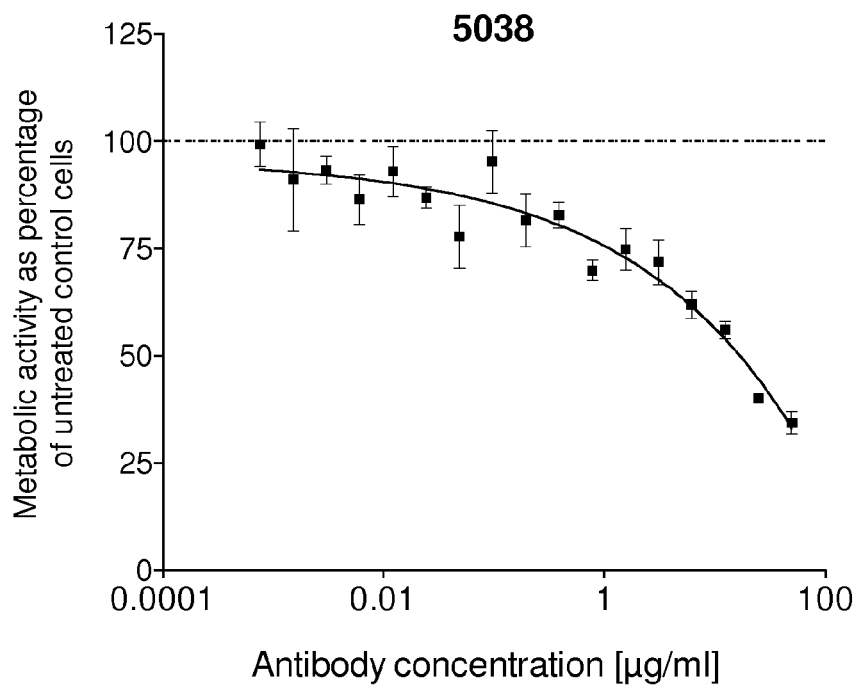
Figure 3:
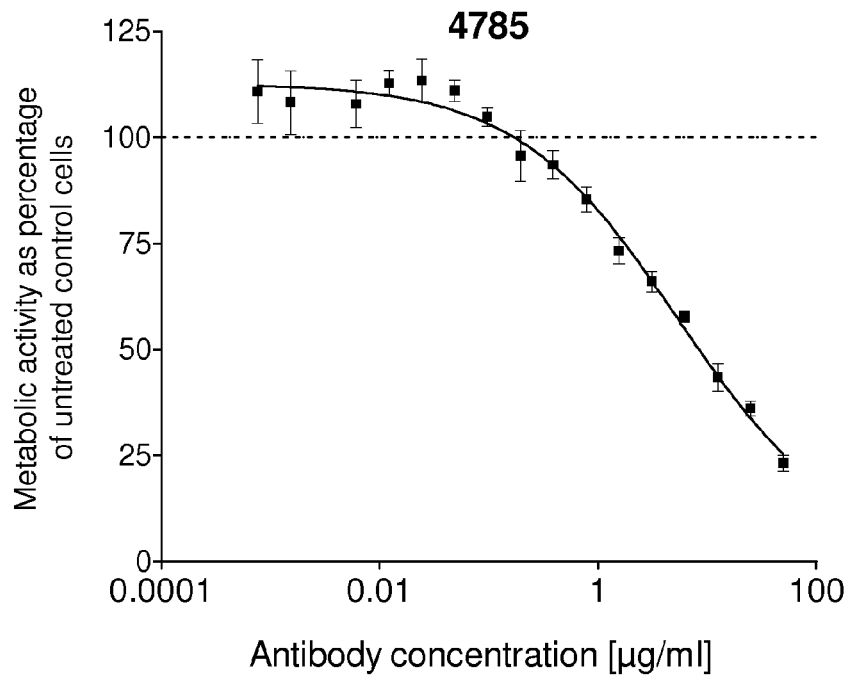
Figure 4:
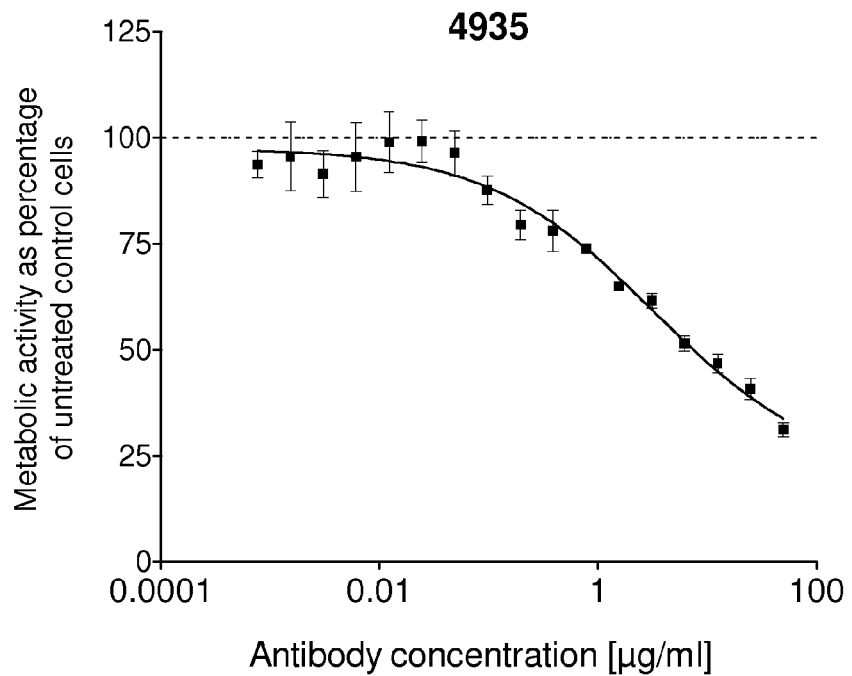
Figure 5:
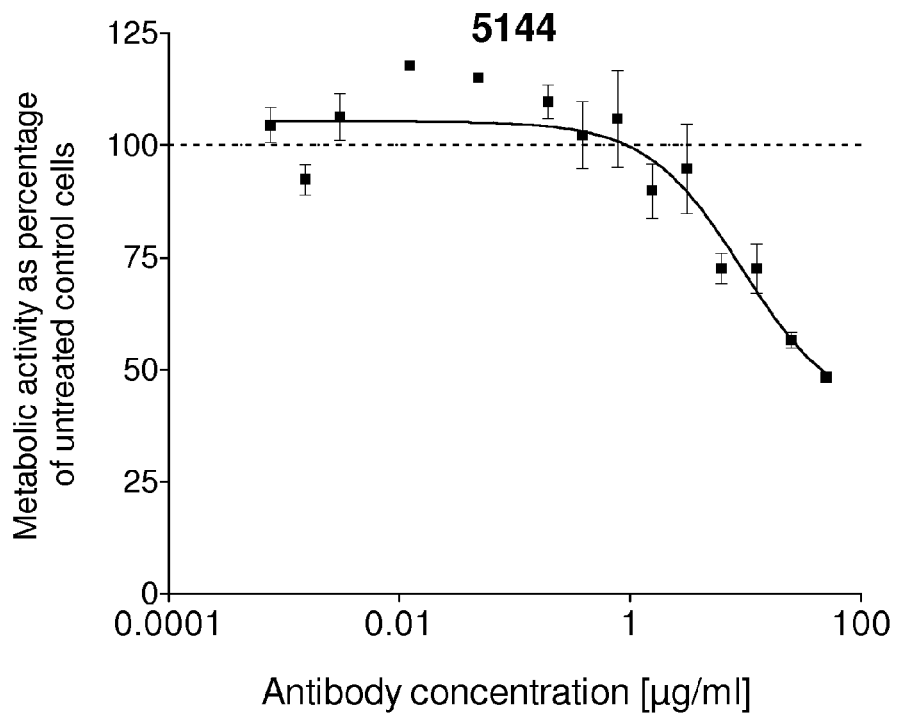
Figure 6:
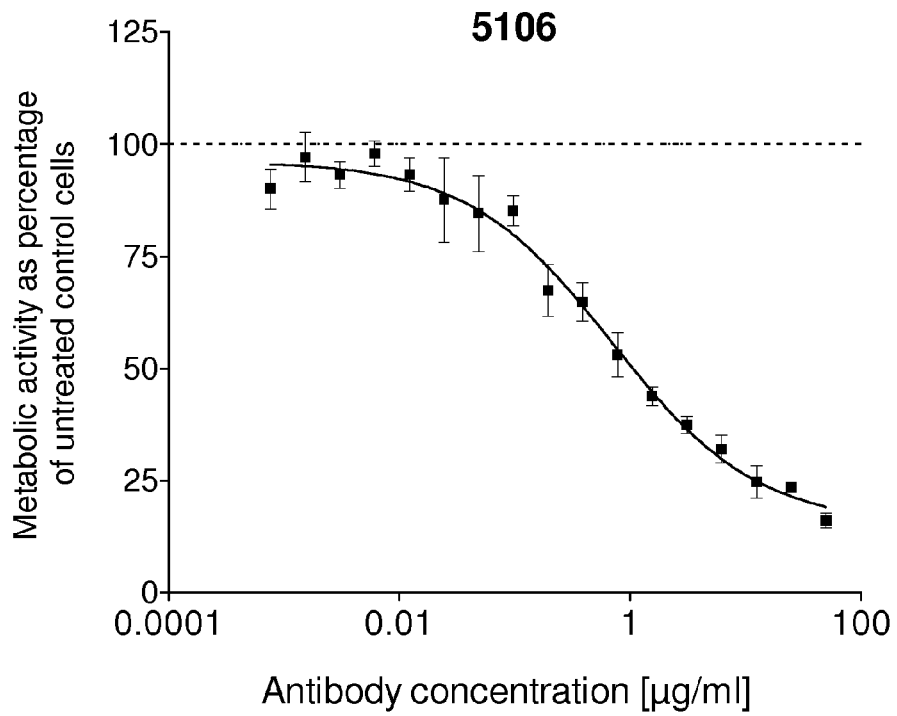
Figure 7:
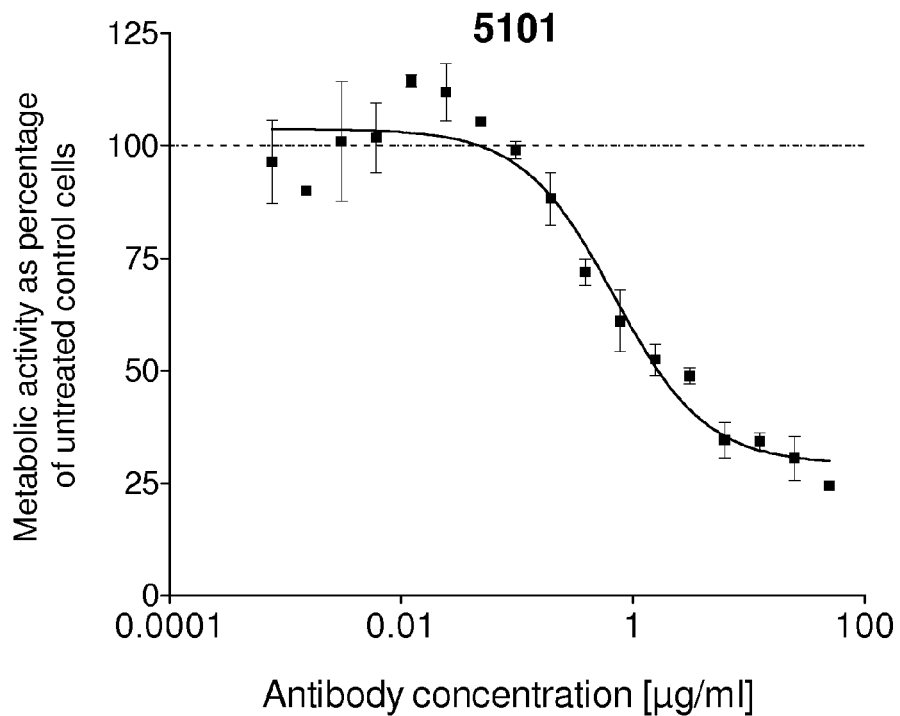
Figure 8:
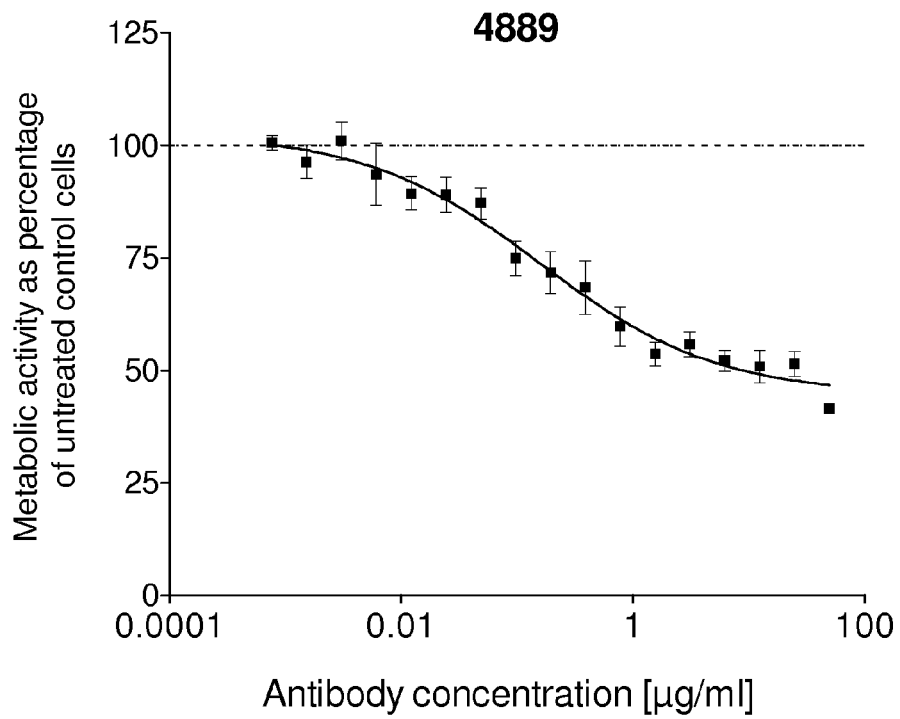
Figure 9:
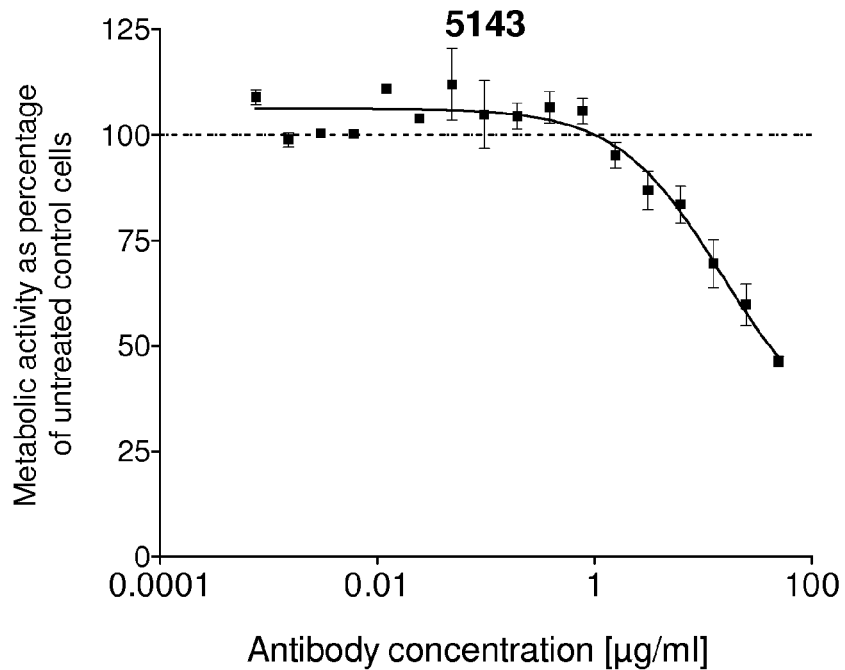
Figure 10:
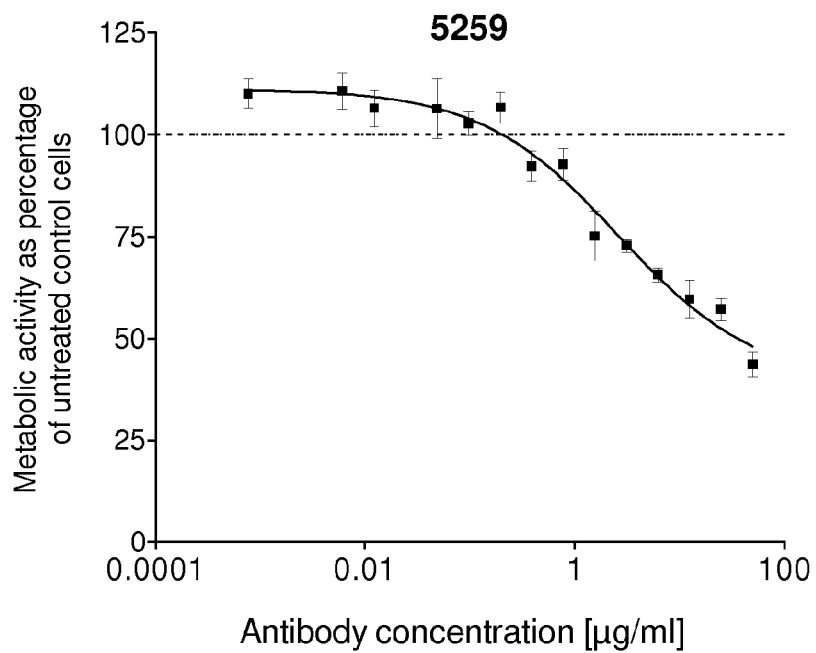

The term "antibody" or "antibody molecule" describes a functional component of serum and is often referred to either as a collection of molecules (antibodies or immunoglobulin) or as one molecule (the antibody molecule or immunoglobulin molecule). An antibody is capable of binding to or reacting with a specific antigenic determinant (the antigen or the antigenic epitope), which in turn may lead to induction of immunological effector mechanisms. An individual antibody is usually regarded as monospecific, and a composition of antibodies may be monoclonal (i.e., consisting of identical antibody molecules) or polyclonal (i.e., consisting of two or more different antibodies reacting with the same or different epitopes on the same antigen or even on distinct, different antigens). Each antibody has a unique structure that enables it to bind specifically to its corresponding antigen, and all natural antibodies have the same overall basic structure of two identical light chains and two identical heavy chains. Antibodies are also known collectively as immunoglobulins.

The terms "antibody" or "antibodies" as used herein are also intended to include chimeric and single chain antibodies, as well as binding fragments of antibodies, such as Fab, Fv fragments or single chain Fv (scFv) fragments, as well as multimeric forms such as dimeric IgA molecules or pentavalent IgM. An antibody may be of human or non-human origin, for example a murine or other rodent-derived antibody, or a chimeric, humanized or reshaped antibody based e.g. on a murine antibody.

Each heavy chain of an antibody typically includes a heavy chain variable region (VH) and a heavy chain constant region. The heavy chain constant region typically includes three domains, referred to as CH1, CH2 and CH3. Each antibody light chain typically includes a light chain variable region (VL) and a light chain constant region. The light chain constant region typically includes a single domain, referred to as CL. The VH and VL regions may be further subdivided into regions of hypervariability ("hypervariable regions", which may be hypervariable in sequence and/or in structurally defined loops). These are also referred to as complementarity determining regions (CDRs), which are interspersed with regions that are more conserved, termed framework regions (FRs). Each VH and VL typically includes three CDRs and four FRs, arranged from the amino terminus to the carboxy terminus in the following order: FR1, CDR1, FR2, CDR2, FR3, CDR3, FR4. The amino acid residues in the variable regions are often numbered using a standardized numbering method known as the Kabat numbering scheme (Kabat et al. (1991) Sequences of Proteins of Immunological Interest, 5th Ed. Public Health Service, National Institutes of Health, Bethesda, Md., USA).

In the appended sequence listing, the light chain (LC) DNA and amino acid sequences include both the light chain variable region (VL) sequence and the human kappa constant region sequence. As mentioned below in Example 1, the human kappa constant region starts with the amino acids—TVAAP- (Thr Val Ala Ala Pro) and ends at the C-terminal with the amino acids—NRGEC (Asn Arg Gly Glu Cys). Therefore, as used herein, the terms "light chain variable region sequence" or "VL" are understood to refer to the N-terminal part of a light chain sequence in the sequence listing before the start of the human kappa constant region (i.e. before the amino acids TVAAP).

The antibody numbers used herein in the context of whole antibodies, e.g. "antibody 5082", refer to the specific antibodies described in the examples and defined in the appended sequence listing. For example, antibody 5082 is an antibody with a heavy chain comprising the heavy chain variable region sequence set forth in SEQ ID NO:18 and the IGHG1 heavy chain constant region sequence set forth in SEQ ID NO:44, and a light chain with the amino acid sequence set forth in SEQ ID NO:20, where the light chain sequence as explained above includes both the light chain variable region sequence (residues 1-108 in SEQ ID NO:20) and the human kappa constant region sequence (residues 109-214 in SEQ ID NO:20).

The invention is also intended to encompass antibodies that are "derived from" or "based on" a specified antibody described herein, where such an antibody comprises, depending on the particular context, one of the following: the heavy chain CDR3 sequence of said specified antibody; the heavy chain CDR3 sequence and the light chain CDR3 sequence of said specified antibody; the heavy chain CDR1, CDR2 and CDR3 sequences and light chain CDR1, CDR2 and CDR3 sequences of said specified antibody; or the heavy chain variable region sequence and the light chain variable region sequence of said specified antibody, or a humanized and/or affinity matured variant of said heavy chain variable region sequence and/or light chain variable region sequence, or a heavy chain and/or light chain variable region sequence having at least 90% sequence identity, preferably at least 95% sequence identity, such as at least 96%, at least 97%, at least 98% or at least 99% sequence identity, with the respective heavy chain variable region and light chain variable region sequences. An antibody that is derived from or based on a specified antibody described herein will generally bind the same HER3 epitope as said specified antibody and will preferably exhibit substantially the same activity as said specified antibody. An antibody is considered to bind the same HER3 epitope as the specified antibody if it competes for binding with said specified antibody.

The specificity of an antibody's interaction with a target antigen resides primarily in the amino acid residues located in the six CDRs of the heavy and light chain. The amino acid sequences within CDRs are therefore much more variable between individual antibodies than sequences outside of CDRs. Because CDR sequences are responsible for most antibody-antigen interactions, it is possible to express recombinant antibodies that mimic the properties of a specific naturally occurring antibody, or more generally any specific antibody with a given amino acid sequence, by constructing expression vectors that express CDR sequences from the specific antibody grafted into framework sequences from a different antibody. As a result, it is possible to "humanize" a non-human antibody and still substantially maintain the binding specificity and affinity of the original antibody. A more detailed discussion of humanization is provided below.

A "chimeric antibody" refers in its broadest sense to an antibody that contains one or more regions from one antibody and one or more regions from one or more other antibodies. As used herein, a "chimeric antibody" is generally an antibody that is partially of human origin and partially of non-human origin, i.e. derived in part from a non-human animal, for example a mouse or other rodent, or an avian such as a chicken. Chimeric antibodies are preferred over non-human antibodies in order to reduce the risk of a human anti-antibody response, e.g. a human anti-mouse antibody response in the case of a murine antibody. An example of a typical chimeric antibody is one in which the variable region sequences are murine sequences derived from immunization of a mouse, while the constant region sequences are human. In the case of a chimeric antibody, the non-human parts, i.e. typically the framework regions of the variable region sequences, may be subjected to further alteration in order to humanize the antibody.

The term "humanize" refers to the fact that where an antibody is wholly or partially of non-human origin, for example a murine antibody obtained from immunization of mice with an antigen of interest or a chimeric antibody based on such a murine antibody, it is possible to replace certain amino acids, in particular in the framework regions and constant domains of the heavy and light chains, in order to avoid or minimize an immune response in humans. It is known that all antibodies have the potential for eliciting a human anti-antibody response, which correlates to some extent with the degree of "humanness" of the antibody in question. Although it is not possible to precisely predict the immunogenicity and thereby the human anti-antibody response of a particular antibody, non-human antibodies tend to be more immunogenic than human antibodies. Chimeric antibodies, where the foreign (usually rodent) constant regions have been replaced with sequences of human origin, have been shown to be generally less immunogenic than antibodies of fully foreign origin, and the trend in therapeutic antibodies is towards humanized or fully human antibodies. For chimeric antibodies or other antibodies of non-human origin, it is therefore preferred that they be humanized to reduce the risk of a human anti-antibody response.

For chimeric antibodies, humanization typically involves modification of the framework regions of the variable region sequences. Amino acid residues that are part of a complementarity determining region (CDR) will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, preferably by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues.

Numerous methods for humanization of an antibody sequence are known in the art; see e.g. the review by Almagro & Fransson (2008) *Front Biosci.* 13: 1619-1633. One commonly used method is CDR grafting, which for e.g. a murine-derived chimeric antibody involves identification of human germline gene counterparts to the murine variable region genes and grafting of the murine CDR sequences into this framework. CDR grafting may be based on the Kabat CDR definitions, although a recent publication (Magdelaine-Beuzelin et al. (2007) *Crit. Rev. Oncol Hematol.* 64: 210-225) has suggested that the IMGT definition (www.imgt.org) may improve the result of the humanization. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al. (1997) *PNAS USA*, vol. 94, pp. 412-417 and the stepwise in vitro affinity maturation method of Wu et al. (1998) *PNAS USA*, vol. 95, pp. 6037-6042.

As noted above, the present invention encompasses humanized antibodies, i.e. antibodies as otherwise described that have been subjected to humanization. These may also be referred to as "humanized variants" of an antibody of the invention. In particular, the terms "heavy chain variable region sequence" and "light chain variable region sequence" as used herein with reference to any specific amino acid sequence are intended to encompass not only that specific sequence but also any humanized variant thereof. Affinity matured variants of the anti-HER3 antibodies described herein are also intended to by encompassed by the present invention.

As used herein, a reference to a heavy chain variable region sequence or a light chain variable region sequence with a particular minimum level of sequence identity compared to a specified heavy chain variable region or light chain variable region sequence, e.g. having at least 90% or at least 95% sequence identity with the reference sequence, such as at least 96%, at least 97%, at least 98% or at least 99% sequence identity, is intended to include, but not to be limited to, humanized and/or affinity matured variants of such reference sequence.

The term "recombinant antibody" refers to an antibody that is expressed from a cell or cell line transfected with an expression vector (or possibly more than one expression vector, typically two expression vectors) comprising the coding sequence of the antibody, where said coding sequence is not naturally associated with the cell.

The term "vector" refers to a nucleic acid molecule into which a nucleic acid sequence can be inserted for transport between different genetic environments and/or for expression in a host cell. A vector that carries regulatory elements for transcription of the nucleic acid sequence (at least a suitable promoter) is referred to as an "an expression vector". The terms "plasmid" and "vector" may be used interchangeably. Expression vectors used in the context of the present invention may be of any suitable type known in the art, e.g. a plasmid or a viral vector.

The terms "polyclonal antibody" or "mixture of [monoclonal] antibodies" refer to a composition of two or more different antibody molecules which are capable of binding to or reacting with different specific antigenic determinants on the same or on different antigens. In the context of the present invention, the individual antibodies of a polyclonal antibody bind to different antigenic determinants of HER3. Preferably the individual antibodies of a polyclonal antibody of the invention bind to different epitopes of HER3, more preferably distinct and substantially non-overlapping epitopes. The variability of a polyclonal antibody is generally thought to be located in the variable regions of the antibody molecules. A "recombinant polyclonal anti-HER3 antibody composition" is a composition comprising a mixture of two or more recombinant monoclonal antibodies that bind HER3.

It is well-known in the art that antibodies exist as different isotypes, such as the human isotypes IgG1, IgG2, IgG3, IgG4, IgA1 and IgA2, or the murine isotypes IgG1, IgG2a, IgG2b, IgG3 and IgA. An antibody of the invention may be of any isotype. Although it is possible for the individual antibodies of a polyclonal antibody composition of the invention to include antibodies of more than one isotype, they are preferably all of the same isotype.

A recombinant antibody composition comprising "at least first and second recombinant anti-HER3 antibodies" will comprise at least two of the specified antibodies, but may include more than two of the anti-HER3 antibodies described herein. In certain cases such a recombinant antibody composition may include a relatively large number of individual anti-HER3 antibodies, e.g. up to 10 or more, such as up to 15 or 20, but will normally include less than 10 different anti-HER3 antibodies, i.e. 2, 3, 4, 5, 6, 7, 8 or 9 antibodies. Recombinant antibody compositions of the invention will more typically include not more than about 6 different anti-HER3 antibodies, and in many cases they will include not more than 4 different anti-HER3 antibodies. In preferred embodiments, a recombinant antibody composition of the invention will therefore include 2, 3 or 4 different anti-HER3 antibodies, typically 2 or 3 different anti-HER3 antibodies.

The term "CDR" or "complementarity determining region" refers to the "hypervariable" regions found in the variable domains of an antibody that are primarily responsible for determining the antibody's binding specificity. See the definition in Lefranc et al (2003), IMGT unique numbering for immunoglobulin and T cell receptor variable domains and Ig superfamily V-like domains, *Dev. Comp Immunol.* 27, 55-77. Each of the heavy and light chains of an antibody contain three CDR regions, referred to as CDR1, CDR2 and CDR3, of which CDR3 shows the greatest variability.

The term "epitope" is used to describe a part of a larger molecule (e.g. antigen or antigenic site) having antigenic or immunogenic activity in an animal. An epitope having immunogenic activity is a portion of a larger molecule that elicits an antibody response in an animal. An epitope having antigenic activity is a portion of a larger molecule to which an antibody immunospecifically binds as determined by any method known in the art. Antigenic epitopes are not necessarily immunogenic. An antigen is a substance to which an antibody or antibody fragment immunospecifically binds, e.g. a toxin, virus, bacteria, protein or DNA. An antigen or antigenic site often has more than one epitope, unless it is very small, and is often capable of stimulating an immune response. Epitopes may be linear or conformational. A linear epitope generally consists of about 6 to 10 adjacent amino acids on a protein molecule that are recognized by an antibody. In contrast, a conformational epitope consists of amino acids that are not arranged sequentially, but where an antibody recognizes a particular three-dimensional structure. When a protein molecule folds into a three-dimensional structure, the amino acids forming the epitope are juxtaposed, enabling the antibody to recognize the conformational epitope. In a denatured protein only linear epitopes are recognized. A conformational epitope, by definition, must be on the outside of the folded protein.

The term "distinct epitopes" refers to the fact that when two different antibodies of the invention bind distinct epitopes, there is less than 100% competition for antigen binding, preferably less than 80% competition for antigen binding, more preferably less than 50% competition for antigen binding, and most preferably as little competition as possible, such as less than about 25% competition for antigen binding. Antibodies capable of competing with each other for binding to the same antigen may bind the same or overlapping epitopes or may have a binding site in the close vicinity of one another, so that competition is mainly caused by steric hindrance. An analysis for "distinct epitopes" of antibody pairs may be performed by methods known in the art, for example by way of binding experiments under saturating antibody conditions using either FACS (fluorescence activated cell sorting) or other flow cytometry analysis on cells expressing HER3 and individual fluorescent labeled antibodies, or by Surface Plasmon Resonance (SPR) using HER3 antigen captured or conjugated to a flow cell surface. A method for determining competition between antibodies using SPR is described in Example 12 below.

The distinct epitopes are preferably "non-overlapping" in the sense that two different anti-HER3 antibodies in a composition of the invention have a sufficiently low competition for antigen binding that the two antibodies are able to bind their respective epitopes simultaneously. It will be understood by persons skilled in the that there can be different degrees of overlap, and that distinct epitopes can be considered to be "non-overlapping" in spite of the presence of some degree of overlap, as long as the respective antibodies are able to substantially bind their epitopes. This is generally considered to be the case when the competition for antigen binding between two antibodies is less than about 50%.

Similarly, an antibody that "competes for binding" with an anti-HER3 antibody of the invention may be defined as one that exhibits competition for antigen binding of about 50% or more.

Antibodies binding to different epitopes on the same antigen can have varying effects on the activity of the antigen to which they bind, depending on the location of the epitope. An antibody binding to an epitope in an active site of the antigen may block the function of the antigen completely, whereas another antibody binding at a different epitope may have no or little effect on the activity of the antigen alone. Such antibodies may, however, still activate complement and thereby result in the elimination of the antigen, and may result in synergistic effects when combined with one or more antibodies binding at different epitopes on the same antigen. In the context of the present invention, the epitope is preferably a portion of the extracellular domain of HER3. Antigens of the present invention are preferably extracellular domain HER3 proteins, polypeptides or fragments thereof to which an antibody or antibody fragment immunospecifically binds. A HER3 associated antigen may also be an analog or derivative of the extracellular domain of HER3 polypeptide or fragment thereof to which an antibody or antibody fragment immunospecifically binds.

The term "immunoglobulin" is commonly used as a collective designation of the mixture of antibodies found in blood or serum, but may also be used to designate a mixture of antibodies derived from other sources.

The term "cognate $V_H$ and $V_L$ coding pair" describes an original pair of $V_H$ and $V_L$ coding sequences contained within or derived from the same antibody-producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or other polynucleotide containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

The term "head-to-head promoters" (also known as "bi-directional promoters") refers to a promoter pair being placed in close proximity so that transcription of two gene fragments driven by the promoters occurs in opposite directions.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The term "HER3" (also known as ErbB-3) stands for "Human Epidermal growth factor Receptor 3" as described above in the "Background of the invention" section. As used herein, it is intended to include variants, isoforms and species homologs of HER3. Preferably, binding of an antibody of the invention to HER3 inhibits the growth of cells expressing HER3 (i.e. typically tumor cells) by inhibiting formation of heteromeric complexes between HER3 and other ErbB family members, e.g. heterodimerization with HER2.

As used herein, the term "inhibits growth" (e.g., referring to cells) is intended to include any measurable decrease in the proliferation (increase in number of cells) or metabolism of a cell when contacted with an anti-HER3 antibody as compared to the growth of the same cells in the absence of an anti-HER3 antibody, e.g. inhibition of growth of a cell culture by at least about 10%, and preferably more, such as at least about 20% or 30%, more preferably at least about 40% or 50%, such as at least about 60%, 70%, 80%, 90%, 99% or even 100%. Growth inhibition can e.g. be determined in relevant cancer cell lines as described in the examples below.

As used herein, the terms "inhibits dimerization" or "inhibits dimer formation" refer to any measurable reduction in the ability of HER3 to form dimers with other receptors, in particular HER2, but also EGFR or HER4, as a result of binding of an anti-HER3 antibody compared to dimer formation in the absence of an anti-HER3 antibody.

The term "treatment" as used herein refers to administration of an anti-HER3 antibody or antibody composition of the invention in a sufficient amount to ease, reduce, ameliorate or eradicate (cure) symptoms or disease states. Administration of two or more anti-HER3 antibodies of the invention will generally be by way of simultaneous administration of the antibodies, preferably in the form of a composition containing all of the anti-HER3 antibodies to be used for treatment. However, it is also possible to administer two or more anti-HER3 antibodies of the invention separately. References herein to e.g. administration of a recombinant antibody composition comprising at least two anti-HER3 antibodies should therefore be understood as encompassing not only administration of a composition comprising the at least two antibodies as such, but also separate administration of the antibodies. Combinations of two or more anti-HER3 antibodies of the invention can thus be administered simultaneously, sequentially or separately.

The percent identity between two sequences, e.g. variable region sequences, refers to the number of identical positions shared by the sequences (calculated as # of identical positions/total # of positions×100), taking into account gaps that must be introduced for optimal alignment of the two sequences. The comparison of sequences and determination of percent identity between two sequences may be accomplished using readily available software. Suitable software programs are available from various sources, both for online use and for download, and for alignment of both protein and nucleotide sequences. One suitable program is ClustalW (Thompson et al. (1994) *Nucleic Acids Res.* 11; 22(22):4673-80), available from www.clustal.org, or alternatively e.g. from the European Bioinformatics Institute (www.ebi.ac.uk), which also provides various other protein and nucleotide informatics tools.

PARTICULAR EMBODIMENTS

One aspect of the invention relates to various novel anti-HER3 antibodies. In one embodiment, the invention thus relates to a recombinant anti-HER3 antibody comprising the heavy chain CDR3 sequence of any one of the antibodies referred to herein as antibodies 4785, 4889, 4935, 5038, 5082, 5101, 5106, 5143, 5144 and 5259.

In another embodiment, the invention relates to a recombinant anti-HER3 antibody comprising the heavy chain CDR3 sequence and the light chain CDR3 sequence of any one of antibodies 4785, 4889, 4935, 5038, 5082, 5101, 5106, 5143, 5144 and 5259.

In another embodiment, the invention relates to a recombinant anti-HER3 antibody comprising the heavy chain CDR1, CDR2 and CDR3 sequences and light chain CDR1, CDR2 and CDR3 sequences of any one of antibodies 4785, 4889, 4935, 5038, 5082, 5101, 5106, 5143, 5144 and 5259.

In a further embodiment, the invention relates to a recombinant anti-HER3 antibody comprising the heavy chain variable region sequence and the light chain variable region sequence of any one of antibodies 4785, 4889, 4935, 5038, 5082, 5101, 5106, 5143, 5144 and 5259, or comprising a humanized and/or affinity matured variant of said heavy chain and/or light chain variable region sequence, or comprising a heavy chain variable region sequence and a light chain variable region sequence each having at least 90% or at least 95% sequence identity with said heavy chain variable region and light chain variable region sequences, such as at least 96%, at least 97%, at least 98% or at least 99% sequence identity with said sequences, and which competes for binding with said antibody.

In a further embodiment, the invention relates to a recombinant anti-HER3 antibody that binds the same epitope as and which competes for binding with any of the antibodies defined above, as well as antibody compositions comprising one or more of such antibodies, preferably comprising at least two such antibodies, e.g. two or three such antibodies as described elsewhere herein.

Table 1 below shows the sequence ID numbers, as set forth in the appended sequence listing, for the DNA and amino acid sequences of the heavy chain variable regions (VH) and the light chains (LC) of antibodies 4785, 4889, 4935, 5038, 5082, 5101, 5106, 5143, 5144 and 5259 (where, as explained above, the light chain sequence includes both the light chain variable region (VL) sequence and the human kappa constant region sequence).

TABLE 1

Sequence ID numbers for the DNA and amino acid sequences of the heavy chain variable regions and the light chains of selected anti-HER3 antibodies

| Antibody No. | VH DNA seq. | VH protein seq. | LC DNA seq. | LC protein seq. |
|---|---|---|---|---|
| 4785 | 1 | 2 | 3 | 4 |
| 4889 | 5 | 6 | 7 | 8 |
| 4935 | 9 | 10 | 11 | 12 |
| 5038 | 13 | 14 | 15 | 16 |
| 5082 | 17 | 18 | 19 | 20 |
| 5101 | 21 | 22 | 23 | 24 |
| 5106 | 25 | 26 | 27 | 28 |
| 5143 | 29 | 30 | 31 | 32 |
| 5144 | 33 | 34 | 35 | 36 |
| 5259 | 37 | 38 | 39 | 40 |

In another aspect, the invention relates to a recombinant antibody composition comprising at least first and second recombinant anti-HER3 antibodies, wherein the first and second antibodies bind distinct epitopes of HER3, and wherein at least one of the first and second antibodies are selected from the group of antibodies outlined above, for example wherein both or all of the anti-HER3 antibodies in the composition are selected from the group of antibodies outlined above.

One embodiment of this aspect of the invention thus relates to a recombinant antibody composition comprising at least first and second recombinant anti-HER3 antibodies, wherein the first and second antibodies bind distinct epitopes of HER3, and wherein each of the first and second antibodies comprise the heavy chain CDR3 sequence of an antibody selected from the group consisting of antibodies 4785, 4889, 4935, 5038, 5082, 5101, 5106, 5143, 5144 and 5259.

Another embodiment of this aspect of the invention relates to a recombinant antibody composition comprising at least first and second recombinant anti-HER3 antibodies, wherein the first and second antibodies bind distinct epitopes of HER3, and wherein each of the first and second antibodies comprise the heavy chain and light chain CDR3 sequences of an antibody selected from the group consisting of antibodies 4785, 4889, 4935, 5038, 5082, 5101, 5106, 5143, 5144 and 5259.

A further embodiment of this aspect of the invention relates to a recombinant antibody composition comprising at least first and second recombinant anti-HER3 antibodies, wherein the first and second antibodies bind distinct epitopes of HER3, and wherein each of the first and second antibodies comprise the heavy chain CDR1, CDR2 and CDR3 sequences and light chain CDR1, CDR2 and CDR3 sequences of an antibody selected from the group consisting of antibodies 4785, 4889, 4935, 5038, 5082, 5101, 5106, 5143, 5144 and 5259.

A further embodiment of this aspect of the invention is a recombinant antibody composition comprising at least first and second recombinant anti-HER3 antibodies, wherein the first and second antibodies bind distinct epitopes of HER3, and wherein each of the first and second antibodies comprise the heavy chain variable region sequence or a humanized and/or affinity matured variant thereof and the light chain variable region sequence or a humanized and/or affinity matured variant thereof of an antibody selected from the group consisting of antibodies 4785, 4889, 4935, 5038, 5082, 5101, 5106, 5143, 5144 and 5259; or wherein each of the first and second antibodies comprise a heavy chain variable region sequence and a light chain variable region sequence each having at least 90% sequence identity, preferably at least 95% sequence identity, such as at least 96%, at least 97%, at least 98% or at least 99% sequence identity, with the heavy chain variable region and light chain variable region sequences, respectively, of an antibody selected from the group consisting of antibodies 4785, 4889, 4935, 5038, 5082, 5101, 5106, 5143, 5144 and 5259, and wherein the first and second antibodies compete for binding with the respective antibodies from which they are derived.

A particular embodiment is an antibody composition comprising at least first and second recombinant anti-HER3 antibodies that bind distinct epitopes of HER3; wherein
  a) the first recombinant antibody comprises a heavy chain variable region sequence and a light chain variable region sequence having at least 90% sequence identity, preferably at least 95% sequence identity, such as at least 96%, at least 97%, at least 98% or at least 99% sequence identity, with the heavy chain variable region and light chain variable region sequences, respectively, of any one reference antibody selected from antibodies 4785, 4889, 4935, 5038, 5082, 5101, 5106, 5143, 5144 and 5259, and wherein the first recombinant antibody binds the same epitope as and competes for binding with said reference antibody; and
  b) the second recombinant antibody comprises a heavy chain variable region sequence and a light chain variable region sequence having at least 90% sequence identity, preferably at least 95% sequence identity, such as at least 96%, at least 97%, at least 98% or at least 99% sequence identity, with the heavy chain variable region and light chain variable region sequences, respectively, of any one reference antibody selected from antibodies 4785, 4889, 4935, 5038, 5082, 5101, 5106, 5143, 5144 and 5259, wherein said reference antibody is different from the reference antibody of a), and wherein the second recombinant antibody binds the same epitope as and competes for binding with said reference antibody.

A still further embodiment of this aspect of the invention is a recombinant antibody composition comprising at least first and second recombinant anti-HER3 antibodies, wherein the first and second antibodies bind distinct epitopes of HER3, and wherein the first and second antibodies are selected from the group consisting of antibodies 4785, 4889, 4935, 5038, 5082, 5101, 5106, 5143, 5144 and 5259, or humanized and/or affinity matured variants thereof.

A still further embodiment of this aspect of the invention is a recombinant antibody composition comprising at least first and second recombinant anti-HER3 antibodies, wherein the first and second antibodies bind distinct epitopes of HER3, and wherein the first and second antibodies are selected from the group consisting of antibodies that bind to the same epitope as and compete for binding with antibodies 4785, 4889, 4935, 5038, 5082, 5101, 5106, 5143, 5144 and 5259.

A further embodiment of this aspect of the invention is an antibody composition comprising at least first and second recombinant anti-HER3 antibodies that bind distinct epitopes of HER3, wherein at least one of said antibodies is selected from the group consisting of:
  (a) an antibody comprising the heavy chain CDR3 sequence and the light chain CDR3 sequence of antibody 4785;
  (b) an antibody comprising the heavy chain CDR3 sequence and the light chain CDR3 sequence of antibody 4889;
  (c) an antibody comprising the heavy chain CDR3 sequence and the light chain CDR3 sequence of antibody 4935;

(d) an antibody comprising the heavy chain CDR3 sequence and the light chain CDR3 sequence of antibody 5038;

(e) an antibody comprising the heavy chain CDR3 sequence and the light chain CDR3 sequence of antibody 5082;

(f) an antibody comprising the heavy chain CDR3 sequence and the light chain CDR3 sequence of antibody 5101;

(g) an antibody comprising the heavy chain CDR3 sequence and the light chain CDR3 sequence of antibody 5106;

(h) an antibody comprising the heavy chain CDR3 sequence and the light chain CDR3 sequence of antibody 5143;

(i) an antibody comprising the heavy chain CDR3 sequence and the light chain CDR3 sequence of antibody 5144; and (j) an antibody comprising the heavy chain CDR3 sequence and the light chain CDR3 sequence of antibody 5259.

Preferably, both of said first and second recombinant anti-HER3 antibodies are selected from antibodies (a)-(j) set forth above. The composition may also comprise at least a third recombinant anti-HER3 antibody, preferably an antibody selected from antibodies (a)-(j) above. In another embodiment, the antibody composition may comprise at least first and second recombinant anti-HER3 antibodies that bind distinct epitopes of HER3, wherein each of said first and second antibodies binds the same epitope as and competes for binding with one of antibodies (a)-(j) set forth above.

A still further embodiment of this aspect of the invention is an antibody composition comprising at least first and second recombinant anti-HER3 antibodies that bind distinct epitopes of HER3, wherein at least one of said antibodies is selected from the group consisting of:

(A) an antibody comprising CDR1, CDR2 and CDR3 of the heavy chain variable region and CDR1, CDR2 and CDR3 of the light chain variable region of antibody 4785;

(B) an antibody comprising CDR1, CDR2 and CDR3 of the heavy chain variable region and CDR1, CDR2 and CDR3 of the light chain variable region of antibody 4889;

(C) an antibody comprising CDR1, CDR2 and CDR3 of the heavy chain variable region and CDR1, CDR2 and CDR3 of the light chain variable region of antibody 4935;

(D) an antibody comprising CDR1, CDR2 and CDR3 of the heavy chain variable region and CDR1, CDR2 and CDR3 of the light chain variable region of antibody 5038;

(E) an antibody comprising CDR1, CDR2 and CDR3 of the heavy chain variable region and CDR1, CDR2 and CDR3 of the light chain variable region of antibody 5082;

(F) an antibody comprising CDR1, CDR2 and CDR3 of the heavy chain variable region and CDR1, CDR2 and CDR3 of the light chain variable region of antibody 5101;

(G) an antibody comprising CDR1, CDR2 and CDR3 of the heavy chain variable region and CDR1, CDR2 and CDR3 of the light chain variable region of antibody 5106;

(H) an antibody comprising CDR1, CDR2 and CDR3 of the heavy chain variable region and CDR1, CDR2 and CDR3 of the light chain variable region of antibody 5143;

(I) an antibody comprising CDR1, CDR2 and CDR3 of the heavy chain variable region and CDR1, CDR2 and CDR3 of the light chain variable region of antibody 5144; and (J) an antibody comprising CDR1, CDR2 and CDR3 of the heavy chain variable region and CDR1, CDR2 and CDR3 of the light chain variable region of antibody 5259.

In this embodiment, both of said first and second recombinant anti-HER3 antibodies are preferably selected from antibodies (A)-(J) set forth above. The composition may also comprise at least a third recombinant anti-HER3 antibody, preferably an antibody selected from antibodies (A)-(J) above. In another embodiment, the antibody composition may comprise at least first and second recombinant anti-HER3 antibodies that bind distinct epitopes of HER3, wherein each of said first and second antibodies binds the same epitope as and competes for binding with one of antibodies (A)-(J) set forth above.

One particular embodiment of this aspect of the invention relates to a recombinant antibody composition comprising at least first and second recombinant anti-HER3 antibodies, wherein the first and second antibodies compete for binding with antibodies 5082 and 5106, respectively, and are:

antibodies 5082 and 5106, or humanized and/or affinity matured variants thereof;

an antibody comprising the heavy chain CDR3 sequence of antibody 5082, and an antibody comprising the heavy chain CDR3 sequence of antibody 5106;

an antibody comprising the heavy and light chain CDR3 sequences of antibody 5082, and an antibody comprising the heavy and light chain CDR3 sequences of antibody 5106;

an antibody comprising the heavy and light chain CDR1, CDR2 and CDR3 sequences of antibody 5082, and an antibody comprising the heavy and light chain CDR1, CDR2 and CDR3 sequences of antibody 5106;

an antibody comprising the heavy and light chain variable region sequences of antibody 5082, and an antibody comprising the heavy and light chain variable region sequences of antibody 5106; or an antibody comprising heavy and light chain variable region sequences each having at least 90% sequence identity, preferably at least 95%, 96%, 97%, 98% or 99% sequence identity with the heavy and light chain variable region sequences, respectively, of antibody 5082, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5106.

Another such embodiment relates to a recombinant antibody composition comprising at least first and second recombinant antibodies, wherein the first and second antibodies compete for binding with antibodies 5082 and 4785, respectively, and are:

antibodies 5082 and 4785, or humanized and/or affinity matured variants thereof;

an antibody comprising the heavy chain CDR3 sequence of antibody 5082, and an antibody comprising the heavy chain CDR3 sequence of antibody 4785;

an antibody comprising the heavy and light chain CDR3 sequences of antibody 5082, and an antibody comprising the heavy and light chain CDR3 sequences of antibody 4785;

an antibody comprising the heavy and light chain CDR1, CDR2 and CDR3 sequences of antibody 5082, and an antibody comprising the heavy and light chain CDR1, CDR2 and CDR3 sequences of antibody 4785;

an antibody comprising the heavy and light chain variable region sequences of antibody 5082, and an antibody comprising the heavy and light chain variable region sequences of antibody 4785; or an antibody comprising heavy and light chain variable region sequences each having at least 90% sequence identity, preferably at least 95%, 96%, 97%, 98% or 99% sequence identity with the heavy and light chain variable region sequences, respectively, of antibody 5082, and an antibody comprising heavy and light chain variable region sequences each having at least 90% sequence identity, preferably at least 95%, 96%, 97%, 98% or 99% sequence identity with the heavy and light chain variable region sequences, respectively, of antibody 4785.

Another such embodiment relates to a recombinant antibody composition comprising at least first and second recombinant antibodies, wherein the first and second antibodies compete for binding with antibodies 5082 and 5038, respectively, and are:

antibodies 5082 and 5038, or humanized and/or affinity matured variants thereof;

an antibody comprising the heavy chain CDR3 sequence of antibody 5082, and an antibody comprising the heavy chain CDR3 sequence of antibody 5038;

an antibody comprising the heavy and light chain CDR3 sequences of antibody 5082, and an antibody comprising the heavy and light chain CDR3 sequences of antibody 5038;

an antibody comprising the heavy and light chain CDR1, CDR2 and CDR3 sequences of antibody 5082, and an antibody comprising the heavy and light chain CDR1, CDR2 and CDR3 sequences of antibody 5038;

an antibody comprising the heavy and light chain variable region sequences of antibody 5082, and an antibody comprising the heavy and light chain variable region sequences of antibody 5038; or an antibody comprising heavy and light chain variable region sequences each having at least 90% sequence identity, preferably at least 95%, 96%, 97%, 98% or 99% sequence identity with the heavy and light chain variable region sequences, respectively, of antibody 5082, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5038.

Another such embodiment relates to a recombinant antibody composition comprising at least first and second recombinant antibodies, wherein the first and second antibodies compete for binding with antibodies 5082 and 5144, respectively, and are:

antibodies 5082 and 5144, or humanized and/or affinity matured variants thereof;

an antibody comprising the heavy chain CDR3 sequence of antibody 5082, and an antibody comprising the heavy chain CDR3 sequence of antibody 5144;

an antibody comprising the heavy and light chain CDR3 sequences of antibody 5082, and an antibody comprising the heavy and light chain CDR3 sequences of antibody 5144;

an antibody comprising the heavy and light chain CDR1, CDR2 and CDR3 sequences of antibody 5082, and an antibody comprising the heavy and light chain CDR1, CDR2 and CDR3 sequences of antibody 5144;

an antibody comprising the heavy and light chain variable region sequences of antibody 5082, and an antibody comprising the heavy and light chain variable region sequences of antibody 5144; or an antibody comprising heavy and light chain variable region sequences each having at least 90% sequence identity, preferably at least 95%, 96%, 97%, 98% or 99% sequence identity with the heavy and light chain variable region sequences, respectively, of antibody 5082, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5144.

Another such embodiment relates to a recombinant antibody composition comprising at least first and second recombinant antibodies, wherein the first and second antibodies compete for binding with antibodies 4889 and 5143, respectively, and are:

antibodies 4889 and 5143, or humanized and/or affinity matured variants thereof;

an antibody comprising the heavy chain CDR3 sequence of antibody 4889, and an antibody comprising the heavy chain CDR3 sequence of antibody 5143;

an antibody comprising the heavy and light chain CDR3 sequences of antibody 4889, and an antibody comprising the heavy and light chain CDR3 sequences of antibody 5143;

an antibody comprising the heavy and light chain CDR1, CDR2 and CDR3 sequences of antibody 4889, and an antibody comprising the heavy and light chain CDR1, CDR2 and CDR3 sequences of antibody 5143;

an antibody comprising the heavy and light chain variable region sequences of antibody 4889, and an antibody comprising the heavy and light chain variable region sequences of antibody 5143; or an antibody comprising heavy and light chain variable region sequences each having at least 90% sequence identity, preferably at least 95%, 96%, 97%, 98% or 99% sequence identity with the heavy and light chain variable region sequences, respectively, of antibody 4889, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5143.

Another such embodiment relates to a recombinant antibody composition comprising at least first and second recombinant antibodies, wherein the first and second antibodies compete for binding with antibodies 4785 and 5038, respectively, and are:

antibodies 4785 and 5038, or humanized and/or affinity matured variants thereof;

an antibody comprising the heavy chain CDR3 sequence of antibody 4785, and an antibody comprising the heavy chain CDR3 sequence of antibody 5038;

an antibody comprising the heavy and light chain CDR3 sequences of antibody 4785, and an antibody comprising the heavy and light chain CDR3 sequences of antibody 5038;

an antibody comprising the heavy and light chain CDR1, CDR2 and CDR3 sequences of antibody 4785, and an antibody comprising the heavy and light chain CDR1, CDR2 and CDR3 sequences of antibody 5038;

an antibody comprising the heavy and light chain variable region sequences of antibody 4785, and an antibody comprising the heavy and light chain variable region sequences of antibody 5038; or an antibody comprising heavy and light chain variable region sequences each having at least 90% sequence identity, preferably at least 95%, 96%, 97%, 98% or 99% sequence identity with the heavy and light chain variable region sequences, respectively, of antibody 4785, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5038.

Another such embodiment relates to a recombinant antibody composition comprising at least first and second recombinant antibodies, wherein the first and second antibodies compete for binding with antibodies 4785 and 5259, respectively, and are:

antibodies 4785 and 5259, or humanized and/or affinity matured variants thereof;

an antibody comprising the heavy chain CDR3 sequence of antibody 4785, and an antibody comprising the heavy chain CDR3 sequence of antibody 5259;

an antibody comprising the heavy and light chain CDR3 sequences of antibody 4785, and an antibody comprising the heavy and light chain CDR3 sequences of antibody 5259;

an antibody comprising the heavy and light chain CDR1, CDR2 and CDR3 sequences of antibody 4785, and an antibody comprising the heavy and light chain CDR1, CDR2 and CDR3 sequences of antibody 5259;

an antibody comprising the heavy and light chain variable region sequences of antibody 4785, and an antibody comprising the heavy and light chain variable region sequences of antibody 5259; or an antibody comprising heavy and light chain variable region sequences each having at least 90% sequence identity, preferably at least 95%, 96%, 97%, 98% or 99% sequence identity with the heavy and light chain variable region sequences, respectively, of antibody 4785, and an antibody comprising heavy and light chain variable region sequences each having at least 90% sequence identity, preferably at least 95%, 96%, 97%, 98% or 99% sequence identity with the heavy and light chain variable region sequences, respectively, of antibody 5259.

Another such embodiment relates to a recombinant antibody composition comprising at least first and second recombinant antibodies, wherein the first and second antibodies compete for binding with antibodies 5106 and 4889, respectively, and are:

antibodies 5106 and 4889, or humanized and/or affinity matured variants thereof;

an antibody comprising the heavy chain CDR3 sequence of antibody 5106, and an antibody comprising the heavy chain CDR3 sequence of antibody 4889;

an antibody comprising the heavy and light chain CDR3 sequences of antibody 5106, and an antibody comprising the heavy and light chain CDR3 sequences of antibody 4889;

an antibody comprising the heavy and light chain CDR1, CDR2 and CDR3 sequences of antibody 5106, and an antibody comprising the heavy and light chain CDR1, CDR2 and CDR3 sequences of antibody 4889;

an antibody comprising the heavy and light chain variable region sequences of antibody 5106, and an antibody comprising the heavy and light chain variable region sequences of antibody 4889; or an antibody comprising heavy and light chain variable region sequences each having at least 90% sequence identity, preferably at least 95%, 96%, 97%, 98% or 99% sequence identity with the heavy and light chain variable region sequences, respectively, of antibody 5106, and an antibody comprising heavy and light chain variable region sequences each having at least 90% sequence identity, preferably at least 95%, 96%, 97%, 98% or 99% sequence identity with the heavy and light chain variable region sequences, respectively, of antibody 4889.

Tables 2 and 3 below show the CDR1, CDR2 and CDR3 amino acid sequences of the heavy chain (Table 2) and the light chain (Table 3) of various anti-HER3 antibodies according to the invention. The amino acid sequences of the heavy chain variable region and the light chain, including the light chain variable region, of these antibodies, as well as the encoding DNA sequences (optimized for expression in CHO cells) are provided in the appended sequence listing. See Table 1 above for an overview of the SEQ ID numbers for these sequences.

TABLE 2

Heavy chain CDR1, CDR2 and CDR3 sequences of selected anti-HER3 antibodies

| Antibody Number | H CDR1 | H CDR2 | H CDR3 | SEQ ID NOs (CDR1/2/3) |
|---|---|---|---|---|
| 4785 | GYSFTSYY | IYPGSGHT | CARPPYYSNYADVW | 45-47 |
| 4889 | GYSITSAYY | VSYDGSN | CAREGDYGYSDYW | 48-50 |
| 4935 | GYTFTSYY | IYPGNVHT | CVRRYGYDGDWFAYW | 51-53 |
| 5038 | GYSITSGFY | ISYDGSN | CARGGGYYGNLFDYW | 54-56 |
| 5082 | GYSITSAYY | IGYDGRN | CSREGDYGYSDYW | 48, 57-58 |
| 5101 | GFTFSSYG | IRDGGGYT | CARGILDYW | 59-61 |
| 5106 | GFTFSSFA | ISDGGSHL | CARGILDYW | 62-63, 61 |
| 5143 | GYSFTSYY | IYPGSGHT | CARPPYYSNYADVW | 45-47 |
| 5144 | GFSLSRYS | IWGGGST | CVRKGITTTGFDYW | 64-66 |
| 5259 | GFSLSRYT | IWGGGST | CARKGITTTGFDYW | 67, 65, 68 |

TABLE 3

Light chain CDR1, CDR2 and CDR3 sequences of selected anti-HER3 antibodies

| Antibody number | L CDR1 | L CDR2 | L CDR3 | SEQ ID NOs (CDR1/3) |
|---|---|---|---|---|
| 4785 | QSLLNSG NQKNY | WAS | CQSDYSYPYTF | 69, 70 |
| 4889 | QDISNY | YTS | CQQSNTLPWTF | 71, 72 |
| 4935 | ESVDSYG NTF | RAS | CQQSNEDPWTF | 73, 74 |
| 5038 | QDISNY | HTS | CQQGITLPWTF | 71, 75 |
| 5082 | QDINNY | YTS | CQQSETLPWTF | 76, 77 |
| 5101 | QDISNY | YTS | CQQGNTLPYTF | 71, 78 |
| 5106 | QDINNY | YTS | CQQYSRIPYTF | 76, 79 |
| 5143 | QSLLNSG NQKNY | WAS | CQNDYSYPYTF | 69, 80 |
| 5144 | SSVSY | DTS | CQQLSSYPPTF | 81, 82 |
| 5259 | SSVSY | DTS | CQQLNSYPPTF | 81, 83 |

Another aspect of the invention relates to nucleic acid molecules comprising a nucleotide sequence that encodes an antibody of the invention, i.e. an antibody selected from the group consisting of antibodies 4785, 4889, 4935, 5038, 5082, 5101, 5106, 5143, 5144 and 5259, or a humanized and/or affinity matured variant thereof; or encoding a heavy and/or light chain variable region sequence of such an antibody, or a heavy and/or light chain sequence having at least 90% sequence identity, preferably at least 95% sequence identity, such as at least 96%, at least 97%, at least 98% or at least 99% sequence identity, with such a heavy and/or light chain variable region sequence.

In one embodiment of this aspect of the invention, the nucleic acid molecule comprises a nucleotide sequence selected from the group consisting of SEQ ID NOS 1, 3, 5, 7, 9, 11, 13, 15, 17, 19, 21, 23, 25, 27, 29, 31, 33, 35, 37 or 39, or sequences that encode the same amino acid sequence as any one of said nucleotide sequences.

A further aspect of the invention relates to an expression vector comprising a nucleic acid molecule as defined above. As noted above, expression vectors for use in the context of the present invention may be of any suitable type known in the art, e.g. a plasmid or a viral vector.

A still further aspect of the invention relates to a host cell comprising a nucleic acid molecule as defined above, wherein said host cell is capable of expressing an anti-HER3 antibody encoded by said nucleic acid molecule.

In a further aspect the binding specificities of any two individual antibodies disclosed herein may be combined in one bispecific binding molecule. Such a bispecific binding molecule preferably comprises the heavy and light chain CDR1, CDR2 and CDR3 sequences of the two selected antibodies. The bispecific binding molecule may be a dual variable domain antibody, i.e. wherein the two arms of the antibody comprise two different variable domains, or may be in the form of an antibody fragment such as a bispecific Fab fragment or a bispecific scFv.

Production of anti-HER3 antibodies and antibody compositions

An additional aspect of the invention relates to methods for producing an anti-HER3 antibody or a mixture of anti-HER3 antibodies of the invention. One embodiment of this aspect of the invention relates to a method for producing an anti-HER3 antibody as defined herein, comprising providing a host cell as defined above capable of expressing an anti-HER3 antibody, cultivating said host cell under conditions suitable for expression of the antibody, and isolating the resulting antibody.

In another embodiment, the invention relates to method for producing a mixture of recombinant anti-HER3 antibodies comprising at least first and second recombinant anti-HER3 antibodies as described herein, the method comprising providing at least a first host cell and a second host cell, wherein the first and second host cells each are capable of expressing a recombinant anti-HER3 antibody, cultivating the first and second host cells under conditions suitable for expression of the first and second antibodies, and isolating the resulting first and second antibodies.

An antibody or antibody composition of the present invention may be produced by methods generally known in the art for production of recombinant monoclonal or polyclonal antibodies.

Thus, in the case of production of a single antibody of the invention, any method known in the art for production of recombinant monoclonal antibodies may be used. For production of an antibody composition comprising two or more anti-HER3 antibodies of the invention, the individual antibodies may be produced separately, i.e. each antibody being produced in a separate bioreactor, or the individual antibodies may be produced together in single bioreactor. When the number of different antibodies in a composition is more than e.g. two or three, it will generally be preferably for reasons of cost efficiency to produce the antibodies together in a single bioreactor. On the other hand, when the composition only contains a small number of different antibodies, e.g. two, three or possibly four different antibodies, a decision to produce them separately in different bioreactors or together in a single bioreactor will have to be made based on the individual circumstances. If the antibody composition is produced in more than one bioreactor, the purified anti-HER3 antibody composition can be obtained by pooling the antibodies obtained from individually purified supernatants from each bioreactor. Various approaches for production of a polyclonal antibody composition in multiple bioreactors, where the cell lines or antibody preparations are combined at a later point upstream or prior to or during downstream processing, are described in WO 2009/129814 (incorporated by reference).

In the case of production of two or more individual antibodies in a single bioreactor, this may be performed e.g. as described in WO 2004/061104 or WO 2008/145133 (both of which are incorporated herein by reference). The method described in WO 2004/061104 is based on site-specific integration of the antibody coding sequence into the genome of the individual host cells, ensuring that the $V_H$ and $V_L$ protein chains are maintained in their original pairing during production. Furthermore, the site-specific integration minimizes position effects, and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the antibody composition from the polyclonal cell line.

WO 2008/145133 describes an alternative approach to production of two or more different antibodies in a single bioreactor. This method involves generation of a polyclonal cell line capable of expressing a polyclonal antibody or other polyclonal protein comprising two or more distinct members by a) providing a set of expression vectors, wherein each of said vectors comprises at least one copy of a distinct nucleic acid encoding a distinct member of the polyclonal protein, separately transfecting host cells with each of the expression vectors under conditions avoiding site-specific integration of the expression vectors into the genome of the cells, thereby obtaining two or more compositions of cells, each composition expressing one distinct member of the polyclonal protein, and c) mixing the at least two compositions of cells to obtain a polyclonal cell line. The methods of WO 2004/061104 and WO 2008/145133 both have the advantage of allowing all of the members constituting the recombinant polyclonal antibody to be produced in a single bioreactor and to be purified in a single process, thereby avoiding the need for separate production and purification processes for each antibody, while at the same time resulting in a surprisingly uniform production of the different antibodies. The method of WO 2008/145133 has the further advantage of providing an increased yield, since each production cell can carry multiple copies of the polynucleotide encoding a particular antibody.

The antibodies of the invention may be produced in various types of cells, including mammalian cells as well as non-mammalian eukaryotic or prokaryotic cells, such as plant cells, insect cells, yeast cells, fungi, E. coli etc. However, the antibodies are preferably produced in mammalian cells, for example CHO cells, COS cells, BHK cells, myeloma cells (e.g. Sp2/0 or NS0 cells), fibroblasts such as NIH 3T3, or immortalized human cells such as HeLa cells, HEK 293 cells or PER.C6 cells.

Methods for transfecting a nucleic acid sequence into a host cell are well-known in the art (see, e.g., Sambrook et al., Molecular Cloning: A Laboratory Manual, Cold Spring Harbor Laboratory Press, 3rd Edition, 2001). For site-specific integration e.g. as described in WO 2004/061104, a suitable host cell will comprise one or more recombinase recognition sites in its genome. In this case, a suitable expression vector comprises a recombination recognition site matching the recombinase recognition site(s) of the host cell. Further details regarding e.g. transfer of selected VH and VL coding pairs from a screening vector using the site-specific integration approach may be found in WO 2004/061104.

When an antibody composition of the invention comprising two or more anti-HER3 antibodies is to be produced in a single bioreactor, cell lines with similar proliferation rates and preferably similar antibody expression levels may be selected to generate a polyclonal cell line. The polyclonal cell line is then generated by mixing the individual cell lines in a predefined ratio. See WO 2009/129814, WO 2004/061104 and WO 2008/145133 (incorporated herein by reference) for further information and examples relating to generating polyclonal cell lines expressing a polyclonal antibodies as well as production of polyclonal antibodies using such cell lines.

One embodiment of the present invention is thus a polyclonal cell line capable of expressing two or more anti-HER3 antibodies of the present invention. A further embodiment is a polyclonal cell line wherein each individual cell is capable of expressing a single $V_H$ and $V_L$ pair, and the polyclonal cell line as a whole is capable of expressing a collection of $V_H$ and $V_L$ pairs, where each $V_H$ and $V_L$ pair encodes an anti-HER3 antibody.

A recombinant antibody composition of the present invention may be manufactured in a single bioreactor by culturing one ampoule from a polyclonal working cell bank (pWCB) in an appropriate medium for a period of time to allow for a sufficient level of antibody expression while maintaining substantial uniformity in the relative expression levels of the individual antibodies expressed by the polyclonal cell line. A production time of between approximately 15 and 50 days will normally be suitable. Culturing methods known in the art such as fed batch or perfusion culturing may be used. The culture medium is preferably a serum-free medium, more preferably a serum-free and protein free medium, e.g. a chemically defined medium. Such culture media are typically designed for growth of the particular cell type being used for production, and numerous suitable media formulations are commercially available.

The recombinant antibody composition is obtained from the culture medium and purified by conventional purification techniques. These may include, for example, affinity chromatography combined with subsequent purification steps such as ion-exchange chromatography, hydrophobic interaction chromatography and gel filtration, as these purification techniques have frequently been used for the purification of recombinant antibodies. When two or more antibodies are produced by a polyclonal cell line in a single bioreactor, the presence of all the individual members in the polyclonal antibody composition is typically assessed subsequent to purification, for example by ion-exchange chromatography. Characterization of a polyclonal antibody composition may be performed e.g. as described in WO 2006/007853, WO 2009/065414, WO 2011/042024 and WO 2011/042027 (incorporated herein by reference).

Therapeutic Compositions

Another aspect of the invention is a pharmaceutical composition comprising as an active ingredient at least one anti-HER3 antibody of the invention, or an anti-HER3 recombinant Fab or another anti-HER3 recombinant antibody fragment composition. Preferably, the active ingredient of such a pharmaceutical composition is an anti-HER3 recombinant antibody composition as described above comprising two or more anti-HER3 antibodies. Such compositions are intended for amelioration, prevention and/or treatment of cancer. The pharmaceutical composition may be administered to a human or to a domestic animal or pet, but will typically be administered to humans.

The ratio between the individual antibodies in a therapeutic composition of the invention, or, in the case of individual antibodies of the invention being administered simultaneously, sequentially or separately, the ratio between the antibodies to be administered, will often be such that the antibodies are administered in equal amounts, but this need not necessarily be the case. Thus, a composition of the invention comprising two anti-HER3 antibodies will often contain them in a 1:1 ratio, and a composition comprising three anti-HER3 antibodies will often contain them in a 1:1:1 ratio. Depending on the characteristics of the individual antibodies, however, it may be desirable to use non-equal amounts of the different antibodies. Suitable ratios for the different anti-HER3 antibodies in compositions of the invention may be determined as described in WO 2010/040356 (incorporated herein by reference), which describes methods for identifying and selecting the optimal stoichiometric ratio between chemical entities in a combinatorial drug product, e.g. a polyclonal antibody composition, to obtain a combinatorial drug with optimal potency and efficacy.

In addition to at least one antibody of the invention or fragment thereof, the pharmaceutical composition will further comprise at least one pharmaceutically acceptable diluent, carrier or excipient. These may for example include preservatives, stabilizers, surfactants/wetting agents, emulsifying agents, solubilizers, salts for regulating the osmotic pressure and/or buffers. Solutions or suspensions may further comprise viscosity-increasing substances, such as sodium carboxymethylcellulose, carboxymethylcellulose, dextran, polyvinylpyrrolidone or gelatin. A suitable pH value for the pharmaceutical composition will generally be in the range of about 5.5 to 8.5, such as about 6 to 8, e.g. about 7, maintained where appropriate by use of a buffer.

Conventional pharmaceutical practice may be employed to provide suitable formulations or compositions to administer to e.g. cancer patients. The administration will typically be therapeutic, meaning that it is administered after a cancer condition has been diagnosed. Any appropriate route of administration may be employed, for example parenteral, intravenous, intra-arterial, subcutaneous, intramuscular, intraperitoneal, intranasal, aerosol, suppository or oral administration. Pharmaceutical compositions of the invention will typically be administered in the form of liquid solutions or suspensions, more typically aqueous solutions or suspensions, in particular isotonic aqueous solutions or suspensions.

The pharmaceutical compositions of the invention are prepared in a manner known per se, for example, by means of conventional dissolving, lyophilizing, mixing, granulating or confectioning processes. The pharmaceutical compositions may be formulated according to conventional pharmaceutical practice (see, for example, Remington: The Science and Practice of Pharmacy (21st edition), ed. A. R. Gennaro, 2005, Lippincott Williams & Wilkins, Philadelphia, Pa., USA; and Encyclopedia of Pharmaceutical Technology, ed. J. Swarbrick, 3rd edition, 2006, Informa Healthcare, New York, N.Y., USA).

As an alternative to a liquid formulation, the compositions of the invention may be prepared in lyophilized form comprising the at least one antibody alone or together with a carrier, for example mannitol, in which case the composition is reconstituted with a liquid such as sterile water prior to use.

The pharmaceutical compositions comprise from approximately 1% to approximately 95%, preferably from approximately 20% to approximately 90%, active ingredient. Pharmaceutical compositions according to the invention may e.g. be produced in unit dose form, such as in the form of ampoules, vials, suppositories, tablets or capsules. The formulations can be administered to human individuals in therapeutically or prophylactically effective amounts (e.g., amounts which prevent, eliminate, or reduce a pathological condition) to provide therapy for a cancerous disease or other condition. The preferred dosage of therapeutic agent to be administered is likely to depend on such variables as the severity of the cancer, the overall health status of the particular patient, the formulation of the compound excipients, and its route of administration.

Therapeutic Uses of Antibodies and Compositions According to the Invention

The anti-HER3 antibodies and pharmaceutical compositions according to the present invention may be used for the treatment or amelioration of a disease in a mammal, in particular treatment of cancer in humans. One embodiment of the invention is a method of preventing, treating or ameliorating one or more symptoms associated with cancer in a human or other mammal, comprising administering an effective amount of an anti-HER3 recombinant antibody composition of the present invention to said mammal.

A particular embodiment relates to a method for treating a human patient with a disorder characterized by expression of HER3, in particular cancer, the method comprising administering to said patient a recombinant anti-HER3 antibody as defined herein or, preferably, a recombinant antibody composition comprising at least two anti-HER3 antibodies as defined herein.

An additional embodiment relates to a method for reducing heterodimer formation between HER3 and other ErbB family receptors in cells that express HER3, the method comprising contacting said cells with a recombinant anti-HER3 antibody as defined herein or, preferably, a recombinant antibody composition comprising at least two anti-HER3 antibodies as defined herein.

A further embodiment of the present invention is the use of an anti-HER3 recombinant antibody or antibody composition of the present invention for the preparation of a composition for the treatment, amelioration or prevention of one or more symptoms associated with cancer in a human or other mammal, e.g. for treatment of a human patient with a disorder characterized by expression of HER3.

Based upon a number of factors, including HER3 expression levels, the following tumor types in particular may be indicated for treatment with an antibody composition of the invention: breast, ovarian, gastric, colon, rectum, prostate, bladder, pancreas, head and neck, and non-small cell lung cancer. Antibody compositions of the invention are contemplated to be particularly applicable to treatment of cancers that express HER3, for example certain epithelial cancers such as many breast cancers, ovarian cancers and gastric (stomach) cancers.

In connection with each of these indications, two main clinical pathways are contemplated, namely 1) adjunctive therapy in connection with at least one additional therapeutic treatment or 2) as a monotherapy. These two options are briefly discussed below.

1) Adjunctive therapy: In adjunctive therapy, also known as combination therapy, patients will be treated with antibodies of the present invention in combination with at least one additional therapeutic treatment, typically a chemotherapeutic or antineoplastic agent and/or radiation therapy. Alternatively or additionally, the anti-HER3 antibodies and compositions of the invention may also be used in combination with a different anti-cancer antibody, e.g. an antibody targeting EGFR or VEGF. The primary cancer targets listed above may thus be treated by administration of an antibody or composition of the invention in addition to standard first line and second line therapy. Protocol designs will address effectiveness as assessed e.g. by reduction in tumor mass as well as the ability to reduce usual doses of standard chemotherapy. Such dosage reductions may allow additional and/or prolonged therapy by reducing dose-related toxicity of the chemotherapeutic agent.

By combining the antibody compositions of the invention with agents known to induce terminal differentiation of cancer cells, the effect may be improved further. Such compounds may, for example, be selected from the group consisting of retinoic acid, trans-retinoic acids, cis-retinoic acids, phenylbutyrate, nerve growth factor, dimethyl sulfoxide, active form vitamin D3, peroxisome proliferator-activated receptor gamma, 12-O-tetradecanoylphorbol 13-acetate, hexamethylene-bis-acetamide, transforming growth factor-beta, butyric acid, cyclic AMP, and vesnarinone. Preferably, the compound is selected from the group consisting of retinoic acid, phenylbutyrate, all-trans-retinoic acid, active form vitamin D.

Pharmaceutical articles comprising an antibody composition of the invention and at least one chemotherapeutic or antineoplastic compound may be used as a combination treatment for the simultaneous, separate or successive administration in cancer therapy. The chemotherapeutic compound may by any chemotherapeutic agent suitable for treatment of the particular cancer in question, for example an agent selected from the group consisting of alkylating agents, for example platinum derivatives such as cisplatin, carboplatin or oxaliplatin; plant alkoids, for example paclitaxel, docetaxel or irinotecan; antitumor antibiotics, for example doxorubicin (adriamycin); topoisomerase inhibitors such as topotecan; and antimetabolites, for example fluorouracil or other fluoropyrimidines.

It is also contemplated that antibodies of the invention may be used in adjunctive therapy in connection with tyrosine kinase inhibitors (TKIs). These are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several tyrosine kinase inhibitors that block EGFR family receptors are currently in clinical development. For a review of these TKIs see Spector et al. (2007) *Breast Cancer Res.* 9(2): 205. Pharmaceutical articles comprising an antibody composition of the invention and at least one TKI targeting HER3 may thus also be used as a combination treatment for the simultaneous, separate or successive administration in cancer therapy.

In other embodiments, the antibody compositions of the present invention may be used in combination with other antibody therapeutics. Examples of these include e.g. antibodies against EGFR (Erbitux® or Vectibix®) or VEGF (Avastin®), as well as other anti-RTK antibodies, for example one or more antibodies against one or more other RTK targets such as HER2 or MET. In yet other embodiments, the antibody compositions of the present invention may be used in combination with an agent known to stimulate cells of the immune system, such combination treatment leading to enhanced immune-mediated enhancement of the efficacy of the antibody compositions of the invention. Examples of such immune-stimulating agents include recombinant interleukins (e.g. IL-21 and IL-2).

2) Monotherapy: In connection with the use of the antibodies in accordance with the present invention in monotherapy of tumors, the antibodies may be administered to patients without concurrent use of a chemotherapeutic or antineoplastic agent, i.e. as a stand-alone therapy.

Immunoconjugates

Another option for therapeutic use of the antibodies and compositions of the invention is in the form of immunoconjugates, i.e. antibodies conjugated to one or more anti-cancer agents. In particular in the case of compositions comprising two or more individual antibodies of the invention that bind distinct HER3 epitopes, it is contemplated that this may generate a cross-linked antibody-receptor lattice on the cell surface, thereby potentially resulting in an increased level of receptor internalization as compared to the use of a single monoclonal antibody. Conjugation of one or more of the individual antibodies of such a composition to one or more anti-cancer agents therefore has the potential to specifically and effectively deliver the conjugated anti-cancer agents to the interior of tumor cells, thereby augmenting the effect of the anti-HER3 antibodies of the invention to provide an improved tumor cell-killing activity.

Various types of anti-cancer agents may be conjugated to the antibodies of the invention, including cytotoxic agents (including conventional chemotherapy agents and other small molecule anti-cancer drugs), cytokines (in which case the conjugate may be termed an "immunocytokine"), toxins (in which case the conjugate may be termed an "immunotoxin") and radionuclides, and a few immunoconjugates have already been approved for clinical use. These include Zevalin® (a murine anti-CD20 antibody conjugated to $^{90}$Y), Bexxar® (a murine anti-CD20 antibody conjugated to $^{131}$I) and Mylotarg® (a humanized anti-CD33 antibody conjugated to calicheamicin). Other immunoconjugates that have been tested in clinical trials include antibodies conjugated to e.g. doxorubicin or a maytansinoid compound. Immunotoxins that have been tested in clinical trials include several antibodies conjugated to a truncated *Pseudomonas* exotoxin A. An immunocytokine comprising a humanized EpCAM antibody conjugated to IL-2 has also been tested.

In the case of antibodies of the invention conjugated to cytotoxic agents, these may e.g. belong to any of the major classes of chemotherapy drugs, including alkylating agents (e.g. carboplatin, cisplatin, oxaliplatin), antimetabolites (e.g. methotrexate, capecitabine, gemcitabine), anthracyclines (e.g. bleomycin, doxorubicin, mitomycin-C) and plant alkaloids (e.g. taxanes such as docetaxel and paclitaxel, and vinca alkaloids such as vinblastine, vincristine and vinorelbine). Since the use of immunoconjugates specifically directs the anti-cancer agent to the tumors, and in particular to the interior of the tumor cells subsequent to internalization, immunoconjugates based on the anti-HER3 antibodies of the invention may advantageously be based on highly cytotoxic agents such as calicheamicin or maytansine derivatives, or on toxins such as bacterial toxins (e.g. *Pseudomonas* exotoxin A, diphtheria toxin) or plant toxins (e.g. ricin).

The conjugated anti-cancer agent in an immunoconjugate is generally linked to the antibody by means of a labile linker that is relatively stable in serum but which allows release of the agent when the immunoconjugate is internalized into the target cell. Suitable linkers include, for example, chemical linkers that are stable at neutral pH in serum but are subjected to acid hydrolysis in the mildly acidic conditions within the lysosomes subsequent to internalization, disulfide linkers that are cleaved by intracellular thiols, and peptide linkers that are stable in serum but which are subjected to enzymatic cleavage in intracellular compartments.

Various conjugation arrangements can be envisioned in compositions containing two or more antibodies of the invention. For example, with two antibodies it would be possible to conjugate the antibodies to two or more different anti-cancer drugs or to conjugate one antibody to a prodrug which is activated by an agent such as an enzyme conjugated to the other antibody.

The general concept of antibody-directed enzyme prodrug therapy (ADEPT) has been described for monoclonal antibodies, where a prodrug is activated by an enzyme targeted to the tumor by a mAB-enzyme conjugate, but the present invention may provide an opportunity for tailoring this approach to particular conditions. It may thus be possible to specifically increase tumor cell killing while sparing or reducing damage to normal tissues.

For further information on anti-cancer immunoconjugates, see Wu et al. (2005) *Nature Biotechnology* 23(9):1137-1146; Schrama et al. (2006) *Nature Reviews/Drug Discovery* 5:147-159; and Rohrer (2009) *chimica oggi/Chemistry Today* 27(5): 56-60.

Dose and Route of Administration

The antibodies and compositions of the invention will be administered in an effective amount for treatment of the condition in question, i.e. at dosages and for periods of time necessary to achieve a desired result. A therapeutically effective amount may vary according to factors such as the particular condition being treated, the age, sex and weight of the patient, and whether the anti-HER3 antibodies are being administered as a stand-alone treatment or in combination with one or more additional anti-cancer treatments.

An effective amount for tumor therapy may be measured by its ability to stabilize disease progression and/or ameliorate symptoms in a patient, and preferably to reverse disease progression, e.g. by reducing tumor size. The ability of an antibody or composition of the invention to inhibit cancer may be evaluated by in vitro assays, e.g. as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

While specific dosing for antibodies in accordance with the invention has not yet been determined, certain dosing considerations can be determined through comparison with a similar product (e.g. a monoclonal antibody directed against HER2 or EGFR) that has been approved for therapeutic use. It is thus contemplated that an appropriate dosage of an antibody composition of the invention will be similar to the recommended dosage for the anti-HER2 monoclonal antibody trastuzumab (Herceptin®) or the anti-EGFR monoclonal antibody panitumumab (Vectibix®). Depending on the particular condition, Herceptin® is administered (by way of infusion) for treatment of breast cancer at either an initial dose of 4 mg/kg and subsequent weekly doses of 2 mg/kg, or an initial dose of 8 mg/kg and subsequent doses of 6 mg/kg every three weeks, while Vectibix® is administered at a dose of 6 mg/kg every 14 days.

It is contemplated that a suitable dose of an antibody composition of the invention will be in the range of 0.1-100 mg/kg, such as about 0.5-50 mg/kg, e.g. about 1-20 mg/kg. The antibody composition may for example be administered in a dosage of at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg; and e.g. up to at most 50 mg/kg, such as up to at the most 30 mg/kg, e.g. up to at the most 20 mg/kg, such as up to at the most 15 mg/kg. Administration will normally be repeated at suitable intervals, e.g. once every week, once every two weeks, once every three weeks, or once every four weeks, and for as long as deemed appropriate by the responsible doctor, who may optionally increase or decrease the dosage as necessary.

Three distinct delivery approaches are contemplated for delivery of the antibodies of the invention. Conventional intravenous delivery will presumably be the standard delivery technique for the majority of tumors. However, in connection with tumors in the peritoneal cavity, such as tumors of the ovaries, biliary duct, other ducts, and the like, intraperitoneal administration may prove favorable for obtaining high dose of antibody at the tumor and to minimize antibody clearance. Similarly, certain solid tumors possess vasculature that is appropriate for regional perfusion. Regional perfusion may allow the obtainment of a high dose of the antibody at the site of a tumor and minimize short term clearance of the antibody.

As with any protein or antibody infusion-based therapeutic product, safety concerns are related primarily to (i) cytokine release syndrome, i.e. hypotension, fever, shaking, chills, (ii) the development of an immunogenic response to the protein (i.e. development of human antibodies by the patient to the recombinant antibody product), and (iii) toxicity to normal cells that express the HER3 receptor. Standard tests and follow-up procedures are utilized to monitor any such safety concerns.

All patent and non-patent references cited in the present application are hereby incorporated by reference in their entirety.

The invention will be further described in the following non-limiting examples.

EXAMPLES

Example 1

Cloning of Anti-HER3 Antibodies

Immunization

Three female mice, one BALB/cJ mouse, one C57BL/6 mouse and one C3H mouse (8-10 weeks old), were used for the immunizations. The mice were immunized with commercially available HER3 protein (R&D Systems cat. #348-RB). For the first four immunizations, HER3 protein was diluted in PBS and mixed 1:1 (v/v) with Freund's adjuvant. The fifth and final immunization was given without adjuvant with the HER3 protein in PBS.

Adjuvant is used to enhance and modulate the immune response. In the first immunization Complete Freund's adjuvant (CFA) was used, whereas Incomplete Freund's adjuvant (IFA) was used for the second, third and fourth immunizations. IFA is an oil-in-water emulsion composed of mineral oils, and CFA is IFA with added heat-killed, dried *Mycobacterium* species. Both adjuvants have a depot effect. The *mycobacterium* in CFA results in a strong activation of the immune system, which leads to long-term persistence of the immune response. Only stable emulsions were administered to mice.

Ten µg recombinant HER3 protein was used for each immunization. In total, the mice received five injections. All mice were injected subcutaneously (s.c.) with 200 µl antigen-adjuvant emulsion for the first four injections and intraperitoneally (i.p.) with 100 µl antigen in PBS for the fifth injection. A summary of the immunizations, adjuvants, injection routes etc. is found in Table 4.

The mice were sacrificed by cervical dislocation, and the spleens and inguinal lymph nodes were harvested. Single cell suspensions were prepared by macerating through a 70 µm cell strainer (Falcon, BD Biosciences, Cat. No. 352350). Cells from the three mice were pooled, resuspended in cold RPMI-1640 with 10% FBS and spun down.

TABLE 4

Immunization summary.

| Day | Immunization | Adjuvant | Antigen µg/dose | Antigen conc. µg/mL | Dose volume | Route of administration |
|---|---|---|---|---|---|---|
| 0 | 1st | CFA | 10 | 50 | 200 µl | s.c. |
| 21 | 2nd | IFA | 10 | 50 | 200 µl | s.c. |
| 42 | 3rd | IFA | 10 | 50 | 200 µl | s.c. |
| 69 | 4th | IFA | 10 | 50 | 200 µl | s.c. |

TABLE 4-continued

Immunization summary.

| Day | Immuni-zation | Adjuvant | Antigen µg/dose | Antigen conc. µg/mL | Dose volume | Route of adminis-tration |
|---|---|---|---|---|---|---|
| 86 | 5$^{th}$ | PBS | 10 | 100 | 100 µl | i.p. |
| 89 | Organ harvest | — | — | — | — | — |

FACS Sorting of Murine Plasma Cells

To remove red blood cells the pooled cell suspension was lysed in 0.17 M NH$_4$Cl. Following lysis the cells were washed twice in 2% FBS/PBS. Cells were re-suspended in 1 ml 2% FBS/PBS, incubated with Fc-block (anti-mouse CD16/CD32, BD Biosciences, Cat. No. 553141) and washed once. Following re-suspension in 2% FBS/PBS, the cells were stained with anti-mouse CD43-FITC (BD Biosciences, Cat. No. 553270), anti-mouse CD138-PE (BD Biosciences, Cat. No. 553714), anti-mouse IgM-Horizon (BD Biosciences, Cat. No. 560575), anti-mouse IgG1-APC (BD Biosciences, Cat. No. 550874), anti-mouse MHC II (I-A/I-Ed)-biotin (BD Biosciences, Cat. No. 553622) and anti-mouse B220/CD45R-PerCP (BD Biosciences, Cat. No. 553093) for 20 min in the dark. Cells were washed, incubated with Strepta-vidin-APC-Cy7 (BD Biosciences, Cat. No. 554063) for 20 min and washed. Cells were FACS sorted on a FACSAria™ cell sorter. Cells that were B220$^{low}$MHCII$^{int}$CD43$^+$CD138$^+$IgM$^-$ were single cell sorted into 384-well microtiter plates containing PCR reaction buffer. Plates were centrifuged, frozen and stored at −80° C.

Linkage of Cognate V$_H$ and V$_L$ Pairs

Linkage of V$_H$ and V$_L$ coding sequences was performed on the single cells gated as plasma cells, facilitating cognate pairing of the V$_H$ and V$_L$ coding sequences. The procedure utilized a two-step PCR procedure based on a one-step multiplex overlap-extension RT-PCR followed by a nested PCR. The primer mixes used in the present example only amplify kappa light chains. Primers capable of amplifying lambda light chains could, however, be added to the multiplex primer mix and nested PCR primer mix if desired. If lambda primers are added, the sorting procedure should be adapted such that lambda positive cells are not excluded. The principle for linkage of cognate V$_H$ and V$_L$ sequences is described in detail in WO 2005/042774 and in Meijer et al. (2006) *J Mol. Biol.* 358(3):764-72.

96-well PCR plates were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR and RNase inhibitor (RNasin, Promega). The primers used for the overlap extension RT-PCR as well as the primer concentrations were the same as those listed in Table 3 of WO 2008/104183. This was supplemented with OneStep RT-PCR5Enzyme Mix (25× dilution; Qiagen) and dNTP mix (200 µM each) to obtain the given final concentration in a 20 µl reaction volume. The plates were incubated for 30 min at 55° C. to allow for reverse transcription (RT) of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in a H20BIT Thermal Cycler with a Peel Seal Basket for 24 96-well plates (AB-gene) to facilitate a high throughput. The PCR plates were stored at −20° C. after cycling.

For the nested PCR step, 96-well PCR plates were prepared with the following mixture in each well (20 µl reactions) to obtain the given final concentration: 1× FastStart buffer (Roche), dNTP mix (200 µM each), nested primer mix, Phusion DNA Polymerase (0.08 U; Finnzymes) and FastStart High Fidelity Enzyme Blend (0.8 U; Roche). The primers used for the nested PCR as well as the primer concentrations were the same as those listed in Table 4 of WO 2008/104183. As template for the nested PCR, 1 µl was transferred from the multiplex overlap-extension PCR reactions. The nested PCR plates were subjected to the following thermocyling: 35×(30 sec at 95° C., 30 sec at 60° C., 90 sec at 72° C.), 10 min at 72° C. Randomly selected reactions were analyzed on a 1% agarose gel to verify the presence of an overlap-extension fragment of approximately 890 basepairs (bp). The plates were stored at −20° C. until further processing of the PCR fragments.

The repertoires of linked V$_H$ and V$_L$ coding pairs from the nested PCR were pooled, without mixing pairs from different donors, and were purified by preparative 1% agarose gel electrophoresis. The human kappa constant light chain encoding sequence was spliced by overlap extension to the V$_L$ coding region of the pooled PCR products of linked V$_H$ and V$_L$ coding pairs as described in WO 2008/104183. The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 µM each), hKCforw-v2 primer and Kappa3' primer (see Table 5 of WO 2008/104183 for primers and concentrations used), and plasmid template pLL138 (10 ng/µl) in a total volume of 50 µl. The reaction was subjected to the following thermocycling: 25×(30 sec at 95° C., 30 sec at 55° C., 45 sec at 72° C.), 10 min at 72° C. The resulting PCR fragment was purified by preparative 1% agarose gel electrophoresis.

The purified pooled PCR fragments from each repertoire were spliced to the amplified and purified PCR fragment of the human kappa constant encoding region (SEQ ID NO:42) by the following splicing by overlap extension PCR (50 µl total volume) containing: human kappa constant encoding region fragment (1.4 ng/µl), purified pooled PCR fragment (1.4 ng/µl), Phusion DNA Polymerase (0.5 U; Finnzymes) and FastStart High Fidelity Enzyme Blend (0.2 U; Roche), 1× FastStart buffer (Roche), dNTP mix (200 µM each), mhKCrev primer and mJH set primers (see Table 5 of WO 2008/104183 for primers and concentrations used). The reaction was subjected to the following thermocycling: 2 min at 95° C., 25×(30 sec at 95° C., 30 sec at 55° C., 1 min at 72° C.), 10 min at 72° C. The resulting PCR fragment (approx. 4518 bp) was purified by preparative 1% agarose gel electrophoresis.

Insertion of Cognate V$_H$ and V$_L$ Coding Pairs into a Screening Vector

In order to identify antibodies with binding specificity to HER3, the V$_H$ and V$_L$ coding sequences obtained were expressed as full-length antibodies. This involved insertion of the repertoire of V$_H$ and V$_L$ coding pairs into an expression vector and transfection into a host cell.

A two-step cloning procedure was employed for generation of a repertoire of expression vectors containing the linked V$_H$ and V$_L$ coding pairs. Statistically, if the repertoire of expression vectors contains ten times as many recombinant plasmids as the number of cognate paired V$_H$ and V$_L$ PCR products used for generation of the screening repertoire, there is a 99% likelihood that all unique gene pairs will be represented. Thus, if 400 overlap-extension V-gene fragments were obtained, a repertoire of at least 4000 clones would be generated for screening to have a 99% likelihood of obtaining all unique gene pairs.

Briefly, the purified PCR products of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, 00-VP-002 (described in WO 2008/104183), by standard ligation procedures. The ligation mix was electroporated into E. coli and added to 2×YT plates containing the appropriate antibiotic and incubated at 37° C. overnight. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in E. coli and the plasmid was purified using standard methods. The generated repertoire of screening vectors was transformed into E. coli by conventional procedures. Colonies obtained were consolidated into 384-well master plates and stored.

A two-step procedure was employed for amplification of mammalian expression plasmids. First, bacteria were lysed and DNA was denatured by incubation in sodium hydroxide. Subsequently, the TempliPhi amplification was performed (GE Amersham). This method utilizes bacteriophage φ29 DNA polymerase to exponentially amplify double-stranded circular DNA templates by rolling circle amplification. For antibody expression in mammalian cells, the 293Freestyle™ expression system (Invitrogen) was applied using standard transfection conditions as recommended by the manufacturer. The cells were supplemented with valproate to 50 mM prior to transfection and the next day Tryptone N1 was added to a final concentration of 1.5% (w/v) of the transfection volume. Supernatants containing antibodies were harvested six days post transfection. Expression levels were estimated with standard anti-IgG ELISA.

Screening for Binding to Recombinant HER3 Protein (ELISA)

Antibody specificity was determined by ELISA using recombinant HER3-protein as antigen.

Briefly, Nunc Maxisorb plates (cat.#464718) were coated with 1 µg/ml HER3 protein (R&D Systems cat.#348-RB), diluted in PBS at 4° C. overnight. Prior to blocking in 50 µl 2% milk-PBS+0.05% Tween 20 the plates were washed once with PBS-T. The plates were washed once with PBS-T and 20 µl of 2% milk-PBS-T, and 10 µl supernatants from FreeStyle293 transfectants were added and incubated for 1 hour at room temperature, after which the plates were washed once with PBS-T, 20 µl per well. Secondary antibody (HRP-Goat-anti-human kappa light chain, Serotec, cat.# STAR 100P) diluted 1:25000 in 2% milk-PBS-T was added to detect the antibodies bound to the wells and incubated for 1 hour at room temperature. The plates were washed once in PBS-T before addition of 25 µl substrate (Kem-En-Tec Diagnostics, cat.#4518) that was incubated for 5 min. 25 µl 1M sulphuric acid was added after the incubation to stop the reaction. Specific signal was detected on an ELISA reader at 450 nm. From the ELISA data 480 positive antibody clones were identified and selected for sequence analysis and validation of binding to HER3.

Sequence Analysis and Clone Selection

The clones identified as binding to HER3 by ELISA were retrieved from the original master plates (384-well format) and streaked on agar plates to generate single colonies, which were picked to LB-medium cultures and incubated at 37° C. overnight with vigorous shaking. Plasmid DNA was isolated from the clones using Qiaprep 96 turbo mini-prep kit (Qiagen, cat. #27193) and submitted for DNA sequencing of the V-genes. The sequences were aligned and all the unique clones were selected. Multiple alignments of obtained sequences revealed the uniqueness of each particular clone and allowed for identification of unique antibodies. Following sequence analysis of the sequenced clones, 33 clusters of related sequences with two to over 40 members as well as over 20 clonotypes that were only represented once were identified. Each cluster of related sequences has probably been derived through somatic hypermutations of a common precursor clone. Overall, one to two clones from each cluster were chosen for validation of sequence and specificity. Based on the cluster analysis, 119 clones were selected for small-scale expression and further characterization. Sequences of selected antibody variable regions are shown in the accompanying sequence listing. As explained above, the light chain sequences shown in the sequence listing all include the same human kappa constant region, which starts with amino acids—TVAAP- and ends at the C-terminal—NRGEC. In order to validate the antibody encoding clones, DNA plasmid was prepared and transfection of FreeStyle CHO-S cells (Invitrogen) at 2 ml scale was performed for expression. The supernatants were harvested 6 days after transfection. Expression levels were estimated with standard anti-IgG ELISA, and the specificity was determined by HER3 specific ELISA as described above in "Screening for binding to recombinant HER3 protein" and by high throughput screening confocal microscopy of antibody binding to HER3 over-expressing cells (see below).

Screening for Binding to HER3 Overexpressing Cells (OPERA)

The 119 clones were screened for binding to the HER3-overexpressing breast cancer cell line (MCF-7) using confocal microscopy. 10,000 MCF-7 cells were seeded into each well of 384-well cell carrier plates (Perkin Elmer, cat.#6007439) and allowed to attach overnight. The media was again discarded and the cells were washed and fixed with 2% formaldehyde solution (Aldrich cat.#533998). After washing, 40 µl of antibody supernatant was transferred to each well and plates were incubated for 2 hours, after which the media in the wells was discarded and 30 µl new media containing 2 µg/ml of Alexa-488 labelled goat anti-human IgG (H+L, Invitrogen cat.# A11013), 2 µg/ml CellMask Blue (Invitrogen cat.# H34558) and 1 µM Hoechst 33342 (Invitrogen cat.# H3570) was added to each well and plates were incubated for another 30 minutes. The level of fluorescence was then measured using an OPERA high throughput confocal microscope (Perkin Elmer).

From the binding data obtained by ELISA and OPERA validation screens, 64 clones were selected for medium scale expression.

Example 2

Functional Characterization of Selected Anti-HER3 Antibodies 67 unique antibodies were selected for functional testing using a viability assay. Cellular damage will inevitably result in loss of the ability of the cell to maintain and provide energy for metabolic cell function and growth. Metabolic activity assays are based on this premise, usually measuring mitochondrial activity. The cell proliferation reagent WST-1 (Roche Cat. No. 11 644 807 001) is a ready-to-use substrate which measures the metabolic activity of viable cells. In this example the WST-1 assay was used to measure the number of metabolically active cells after treatment of cancer cells with 2 µg/ml of different anti-HER3 antibodies for 96 hours.

The cancer cell lines MDA-MB-175 (ATCC cat.# HTB-25), A431NS (ATCC cat.# CRL-2592), MCF-7 (ATCC cat.# HTB-22) and MDA-MB-453 (ATCC cat.# HTB-130) were seeded into 96-well plates at a concentration of 1000 cells/well in media containing 2 µg/ml of anti-HER3 antibody. The plates were incubated for 4 days in a humidified incubator at 37° C. 20 µl of WST-1 reagent was then added per well and the plates were incubated for one hour at 37° C. Plates were then transferred to a orbital plate shaker and left for another hour. The absorbance was measured at 450 nm and 620 nm (reference wavelength) on an ELISA reader. The difference in the levels of metabolically active cells (MAC) was calculated as percent of the control supernatants as follows:

$$\% \, MAC = \left(1 - \frac{(ODexp. - ODmedia)}{(ODuntreat. - ODmedia)}\right) \times 100$$

It is assumed that the metabolic activity correlates with the number of viable cells, a lower % MAC corresponding to a higher level of cell growth inhibition by the antibodies.

The results of this analysis for selected antibodies are shown in Table 5 below, where data is provided for the individual cancer cell lines as well as the median level of inhibition across the four cell lines. It is evident from these results that HER3 antibodies with a range of functional activities have been identified and that the antibodies in the repertoire exhibit an inhibitory effect on all or most of the tested cancer cell lines.

TABLE 5

Percent metabolically active cells (MAC) in the presence of anti-HER3 antibodies

| Antibody No. | MDA-MB-175 | MCF-7 + 1 nM Heregulin | MDA-453 | A431NS | Median |
|---|---|---|---|---|---|
| 4785 | 60 | 80 | 53 | 70 | 65 |
| 4889 | 50 | 76 | 52 | 80 | 64 |
| 4935 | 74 | 95 | 67 | 86 | 80 |
| 5038 | 78 | 76 | 65 | 83 | 77 |
| 5082 | 43 | 60 | 66 | 67 | 63 |
| 5101 | 65 | 88 | 80 | 82 | 81 |
| 5106 | 57 | 87 | 78 | 87 | 82 |
| 5143 | 73 | 87 | 69 | 78 | 75 |
| 5144 | 79 | 89 | 73 | 79 | 79 |
| 5259 | 72 | 90 | 81 | 77 | 79 |

Dose-response curves were generated for the ten antibodies in Table 5 using the cell line MDA-MB-175, which is the most sensitive to HER3 inhibition; see FIGS. 1-10, which show metabolic activity of MDA-MB-175 cells treated with different concentrations of the indicated antibodies for 96 hours. All tested antibodies block proliferation of MDA-MB-175 cells, but on the basis of the in vivo data shown in FIGS. 1-10 the antibodies 5101 and 5106 appear to be the most efficacious.

Example 3

Inhibition of HER3 Phosphorylation by Anti-HER3 Antibodies

Figure 11:
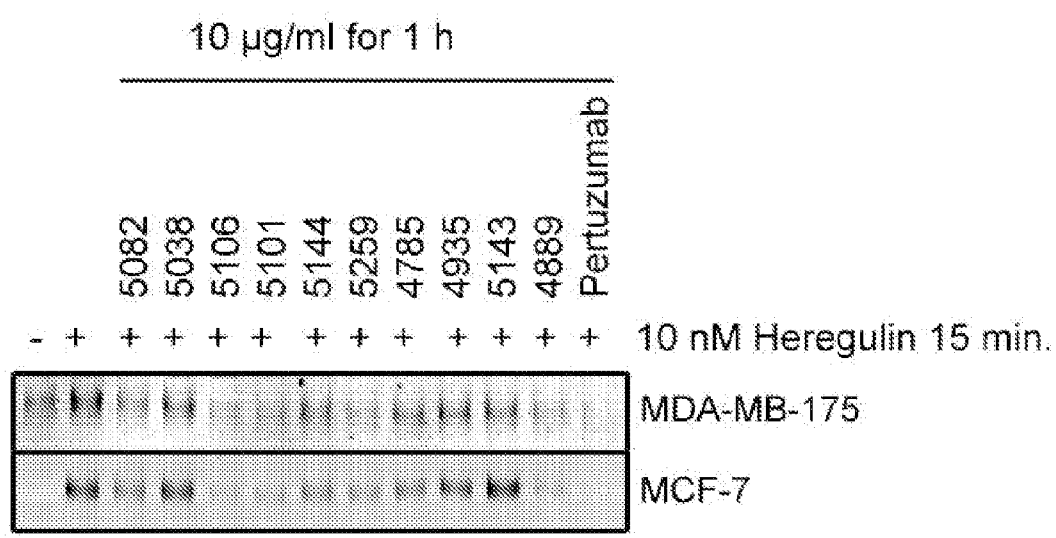
FIG. 11 shows the results of western blot analyses of phospho-HER3 levels in the cell lines MDA-MB-175 and MCF7 after 1 hour of pre-treatment with the indicated antibodies, followed by stimulation with 10 nM heregulin beta.

This example demonstrates that anti-HER3 antibodies are able to inhibit ligand-induced phosphorylation of HER3.
Methods
In order to investigate the level of HER3 phosphorylation in cell lines treated with anti-HER3 antibodies, western blot analyses were performed on whole cell lysates of MDA-MB-175 and MCF7 cells that were pre-treated with the antibodies for 1 hour and then stimulated with 10 nM of heregulin beta. Cells were grown in T-75 culture flasks and at 80% confluency the culture media were removed, and the cells were washed in 1×PBS and treated with 10 µg/ml of the antibodies diluted in 5 ml medium containing 0.5% FBS. Cells were treated for one hour, after which whole cell lysates were prepared using standard RIPA buffer. The total protein concentration was determined in each sample and 10 µg protein was analyzed by western blotting using primary antibody against phosphorylated HER3 (pHER3).
Results
The results of western blot analyses of phospho-HER3 levels in the cell lines MDA-MB-175 and MCF7 after 1 hour of pre-treatment with the indicated antibodies, followed by stimulation with 10 nM heregulin beta, are shown in FIG. 11. The different anti-HER3 antibodies inhibited ligand-induced HER3 phosphorylation to various degrees, with the best antibodies in this assay being 5101, 5106, 5259 and 4889. Antibodies 5038 and 5143 had only limited effect on the levels of phosphorylated HER3 in these cell lines.

Example 4

Functional Characterization of Mixtures of Two Anti-HER3 Antibodies

This example describes in vitro testing of all possible mixtures of two antibodies among ten selected anti-HER3 antibodies of the invention with confirmed binding to human HER3. The antibody mixtures were evaluated for their ability to inhibit the growth of four different cancer cell lines: MDA-MB-175, MCF7 (+1 nM Heregulin beta), H1437 (+1 nM Heregulin beta) and A431NS (1 µg/ml of anti-EGFR mixture 992+1024). The anti-EGFR mixture 992+1024 is contains equal amounts of the two anti-EGFR antibodies referred to as 992 and 1024 as described in WO 2008/104183.
Methods
Antibodies 4785, 4889, 4935, 5038, 5082, 5101, 5106, 5143, 5144 and 5259, each of which had confirmed binding to the human HER3 receptor, were tested in all possible mixtures of two antibodies in order to identify antibody mixtures with optimal efficacy. The methods used, e.g. for preparing the different antibody combinations in the 384-well plates, were those generally described in WO 2010/040356. Further details are provided below.
Mixtures of Two Antibodies
The ten antibodies were diluted to a concentration of 25 µg/ml in 1×PBS, and 100 µl of antibody solution was added to the wells of 384-well feeder plates for use in preparing mixtures of two antibodies for testing.

For each of the four cell lines tested, two separate 384-well plates were used, with 46 µl of media containing cells being added to the wells. A Biomek 3000 laboratory automation workstation (Beckman Coulter) was used to add 2 µl of each of two different antibodies from the feeder plates to the wells of the 384-well plates containing media+cells, such that all combinations of two different antibodies were represented. In addition, the plates included media control wells (50 μl 1×PBS media; no cells), untreated control wells (50 μl 1×PBS media+cells; no antibody), and wells containing (in addition to 46 μl of media+cells) 4 μl of media with only one of the ten antibodies of the invention as an additional control.

The plates with wells containing mixtures of two antibodies, as well as media and untreated control wells or a single antibody of the invention, were incubated for 4 days in a humidified incubator at 37° C., after which 5 μl of the cell proliferation reagent WST-1 diluted 1:1 in 1×PBS was added to all relevant wells on the plates. The plates were then incubated for 1 hour at 37° C. and subsequently transferred to orbital shakers and incubated for another hour. The absorbance was measured at 450 nm and 620 nm (reference wavelength) on an ELISA reader. The amount of metabolically active cells (MAC) was calculated as described in Example 2.

Dose-response curves were generated for selected mixtures (highlighted in bold in Table 6 below) using the cell lines MDA-MB-175 and MCF-7. Prior to performing the WST-1 assay, the appropriate antibodies and antibody mixes were diluted to a final total antibody concentration of 100 μg/ml in appropriate media supplemented with 2% of FBS and 1% Penicillin/Streptomycin (P/S), yielding a final total antibody concentration of 50 μg/ml in the well containing the highest antibody concentration. A two-fold serial dilution of the antibodies was then performed. Relevant numbers of cells were then added to the experimental wells in a 384-well plate. The plates were incubated for 4 days in a humidified incubator at 37° C. The amount of metabolically active cells (MAC) was calculated as the percent of the untreated control as described in Example 2.

Results

The individual antibodies and mixtures of two antibodies were ranked according to their median effect on cell growth, calculated as % MAC. The results are shown below in Table 6.

The results show that the level of growth inhibition by the various mixtures varies considerably between the different cell lines, while the difference in the median % MAC is less pronounced. The monoclonal antibody 5082 was found to have the highest level of median growth inhibition (lowest % MAC), while several antibody mixtures are superior at inhibiting the cell line MDA-MB-175. It should be noted that although the antibodies and antibody mixtures in Table 6 are ranked based on the median % MAC for the four cell lines, it is contemplated that individual antibody mixtures may be of interest based on an effect demonstrated in any one or more cell lines, and that a high level of inhibition (low % MAC) in just a single cell line may translate into a highly useful antibody combination in vivo against certain types of cancers.

Dose-response curves were generated for mixtures of two antibodies that bind non-overlapping epitopes of HER3 and unique epitope bin combinations (highlighted in bold). The results show that all the mixtures inhibit all four cell lines although with different potency.

TABLE 6

Level of cancer cell growth inhibition by mixtures of two anti-HER3 antibodies in the four cancer cell lines MDA-MB-175, MCF7, H1437 and A431NS. The level of inhibition is shown as % metabolically active cells (% MAC).

|  | MDA-MB-175 | | MCF7 + 1 nM Heregulin beta | | H1437 + 1 nM Heregulin beta | | A431NS + 1 μg/ml Sym004* | | Median |
|---|---|---|---|---|---|---|---|---|---|
|  | % MAC | SD | % MAC | SD | % MAC | SD | % MAC | SD | % MAC |
| 5082 | 42.7 | 4.6 | 55.2 | 3.5 | 69.4 | 5.2 | 74.5 | 5.1 | 62.3 |
| 5082 + 5106 | 37.1 | 5.9 | 55.2 | 0.9 | 77.1 | 3.9 | 82.9 | 6.1 | 66.1 |
| 5082 + 4889 | 47.5 | 7.3 | 65.8 | 4.4 | 72.3 | 4.7 | 77.7 | 6.7 | 69.0 |
| 5082 + 5101 | 43.7 | 11.3 | 61.6 | 7.7 | 76.8 | 9.8 | 84.4 | 8.3 | 69.2 |
| 5082 + 5259 | 52.7 | 3.2 | 59.3 | 10.4 | 79.1 | 4.5 | 90.0 | 8.4 | 69.2 |
| 5082 + 4935 | 45.9 | 5.1 | 58.7 | 7.8 | 79.8 | 7.2 | 90.0 | 8.8 | 69.2 |
| 5082 + 4785 | 45.5 | 10.9 | 61.9 | 8.6 | 77.1 | 8.5 | 87.7 | 10.3 | 69.5 |
| 5082 + 5143 | 51.5 | 4.3 | 65.4 | 10.3 | 75.1 | 4.2 | 84.2 | 5.0 | 70.2 |
| 5082 + 5144 | 49.3 | 5.1 | 60.8 | 9.8 | 80.0 | 4.2 | 86.1 | 6.6 | 70.4 |
| 5082 + 5038 | 32.2 | 7.7 | 62.7 | 11.2 | 79.0 | 5.6 | 90.2 | 8.8 | 70.9 |
| 5038 + 4889 | 39.9 | 6.9 | 69.2 | 8.6 | 77.2 | 10.2 | 90.4 | 13.1 | 73.2 |
| 4785 + 4889 | 37.0 | 1.0 | 65.2 | 2.4 | 81.8 | 5.1 | 96.5 | 14.4 | 73.5 |
| 4935 + 4889 | 47.2 | 9.9 | 73.3 | 6.4 | 82.7 | 7.3 | 86.6 | 11.8 | 78.0 |
| 4889 + 5143 | 44.5 | 2.3 | 76.1 | 1.9 | 82.3 | 2.4 | 89.9 | 8.1 | 79.2 |
| 5038 + 5143 | 67.3 | 6.5 | 75.3 | 2.7 | 84.0 | 6.4 | 90.1 | 9.5 | 79.6 |
| 4889 + 5259 | 53.6 | 4.9 | 78.2 | 2.7 | 81.2 | 4.3 | 87.0 | 8.3 | 79.7 |
| 4785 + 5038 | 47.9 | 6.0 | 74.2 | 10.8 | 86.7 | 4.8 | 100.4 | 2.3 | 80.5 |
| 4785 + 5259 | 63.1 | 10.6 | 77.1 | 9.6 | 83.9 | 11.3 | 98.9 | 4.2 | 80.5 |
| 5106 + 4889 | 47.1 | 3.0 | 78.4 | 3.5 | 83.7 | 4.6 | 90.0 | 8.0 | 81.1 |
| 5101 + 4889 | 51.3 | 5.2 | 82.3 | 5.7 | 84.7 | 6.0 | 82.3 | 14.1 | 82.3 |
| 5038 + 5259 | 61.8 | 5.1 | 77.7 | 7.5 | 86.9 | 2.9 | 104.0 | 5.2 | 82.3 |
| 4785 + 5106 | 52.3 | 6.7 | 80.9 | 11.1 | 84.0 | 3.2 | 92.5 | 7.1 | 82.4 |
| 4889 | 54.0 | 18.1 | 90.8 | 7.4 | 83.3 | 4.2 | 82.7 | 5.5 | 83.0 |
| 5143 + 5259 | 74.2 | 9.5 | 79.6 | 3.8 | 87.7 | 4.7 | 96.9 | 3.3 | 83.6 |
| 5101 | 54.6 | 6.6 | 83.7 | 6.6 | 100.7 | 2.5 | 84.6 | 8.5 | 84.1 |
| 4785 | 60.7 | 11.1 | 81.2 | 7.8 | 88.3 | 11.1 | 91.4 | 6.5 | 84.8 |
| 5259 | 69.2 | 10.8 | 79.4 | 6.5 | 90.3 | 4.2 | 96.0 | 7.4 | 84.8 |
| 5038 | 80.3 | 19.1 | 86.3 | 9.6 | 84.1 | 8.9 | 93.4 | 2.8 | 85.2 |
| 5144 + 4889 | 58.1 | 5.4 | 87.0 | 5.4 | 86.2 | 5.4 | 89.7 | 11.8 | 86.6 |
| 5038 + 4935 | 63.9 | 4.6 | 87.7 | 5.2 | 85.8 | 8.6 | 103.4 | 7.3 | 86.8 |
| 5038 + 5101 | 63.8 | 8.8 | 87.9 | 2.9 | 86.0 | 4.4 | 89.5 | 8.7 | 86.9 |
| 4785 + 5143 | 72.1 | 11.6 | 92.3 | 4.5 | 82.8 | 5.1 | 92.5 | 5.6 | 87.6 |

TABLE 6-continued

Level of cancer cell growth inhibition by mixtures of two anti-HER3 antibodies
in the four cancer cell lines MDA-MB-175, MCF7, H1437 and A431NS. The
level of inhibition is shown as % metabolically active cells (% MAC).

|  | MDA-MB-175 | | MCF7 + 1 nM Heregulin beta | | H1437 + 1 nM Heregulin beta | | A431NS + 1 µg/ml Sym004* | | Median |
| --- | --- | --- | --- | --- | --- | --- | --- | --- | --- |
|  | % MAC | SD | % MAC | SD | % MAC | SD | % MAC | SD | % MAC |
| 5038 + 5106 | 65.3 | 4.0 | 90.7 | 8.2 | 84.9 | 5.2 | 94.6 | 7.6 | 87.8 |
| 5101 + 5106 | 59.3 | 4.2 | 84.6 | 4.6 | 102.8 | 5.5 | 91.2 | 6.9 | 87.9 |
| 5143 | 69.0 | 13.9 | 92.7 | 7.7 | 84.0 | 3.8 | 93.8 | 3.3 | 88.4 |
| 5101 + 5259 | 61.6 | 12.1 | 85.0 | 5.1 | 99.5 | 8.8 | 92.2 | 4.0 | 88.6 |
| 4935 + 5259 | 74.9 | 10.5 | 88.4 | 6.7 | 89.2 | 0.7 | 102.0 | 2.9 | 88.8 |
| 5038 + 5144 | 73.6 | 9.7 | 85.1 | 7.1 | 93.3 | 5.2 | 97.0 | 6.5 | 89.2 |
| 4785 + 5101 | 64.7 | 13.8 | 87.8 | 7.9 | 91.1 | 5.1 | 92.3 | 7.3 | 89.5 |
| 4785 + 5144 | 69.5 | 6.9 | 87.1 | 2.0 | 93.8 | 7.2 | 97.8 | 3.9 | 90.5 |
| 5106 | 47.6 | 10.7 | 84.3 | 14.0 | 97.8 | 4.9 | 98.1 | 3.4 | 91.0 |
| 5106 + 5143 | 70.8 | 5.2 | 91.0 | 5.6 | 91.7 | 6.4 | 94.5 | 3.7 | 91.4 |
| 5101 + 5143 | 66.2 | 10.0 | 93.0 | 7.6 | 93.1 | 6.3 | 89.9 | 5.4 | 91.4 |
| 4785 + 4935 | 72.2 | 6.8 | 90.6 | 3.8 | 93.2 | 6.8 | 102.7 | 5.5 | 91.9 |
| 5106 + 5259 | 63.1 | 4.0 | 87.9 | 2.4 | 98.6 | 4.4 | 99.2 | 3.4 | 93.2 |
| 4935 + 5106 | 65.6 | 5.6 | 95.3 | 14.7 | 92.1 | 6.3 | 99.7 | 11.1 | 93.7 |
| 5144 + 5143 | 80.0 | 11.1 | 91.8 | 5.0 | 96.2 | 10.5 | 98.9 | 7.5 | 94.0 |
| 4935 | 78.1 | 15.0 | 98.6 | 12.8 | 91.1 | 6.7 | 99.6 | 15.0 | 94.8 |
| 4935 + 5143 | 87.3 | 6.4 | 101.6 | 11.3 | 91.6 | 9.7 | 99.6 | 9.4 | 95.6 |
| 5144 + 5106 | 62.2 | 10.4 | 92.0 | 3.9 | 100.1 | 7.6 | 101.3 | 5.4 | 96.0 |
| 4935 + 5101 | 72.8 | 14.8 | 96.3 | 5.7 | 96.2 | 7.1 | 100.6 | 11.3 | 96.3 |
| 5144 | 72.6 | 16.4 | 94.8 | 11.5 | 99.2 | 8.9 | 99.0 | 10.9 | 96.9 |
| 5144 + 5101 | 62.6 | 9.9 | 98.6 | 1.7 | 105.6 | 2.3 | 97.8 | 5.1 | 98.2 |
| 5144 + 5259 | 79.0 | 2.0 | 98.0 | 7.1 | 98.8 | 3.5 | 102.4 | 5.4 | 98.4 |
| 4935 + 5144 | 81.4 | 4.8 | 104.6 | 16.3 | 99.5 | 5.4 | 99.5 | 8.7 | 99.5 |

*Sym004 is a mixture of two recombinant anti-EGFR antibodies directed against non-overlapping EGFR epitopes; see WO 2008/104183 and Pedersen et al. (2010) Cancer Res. 70(2): 588-597.

Figure 12:
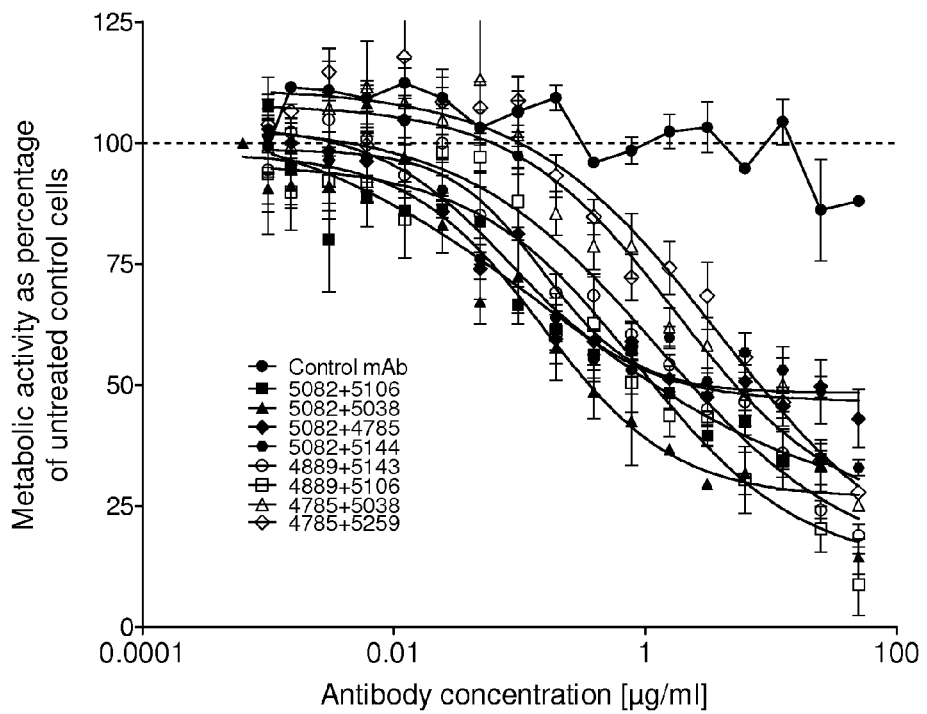
FIGS. 12-15 show the metabolic activity of selected mixtures of two anti-HER3 antibodies in four cancer cell lines.
Figure 13:
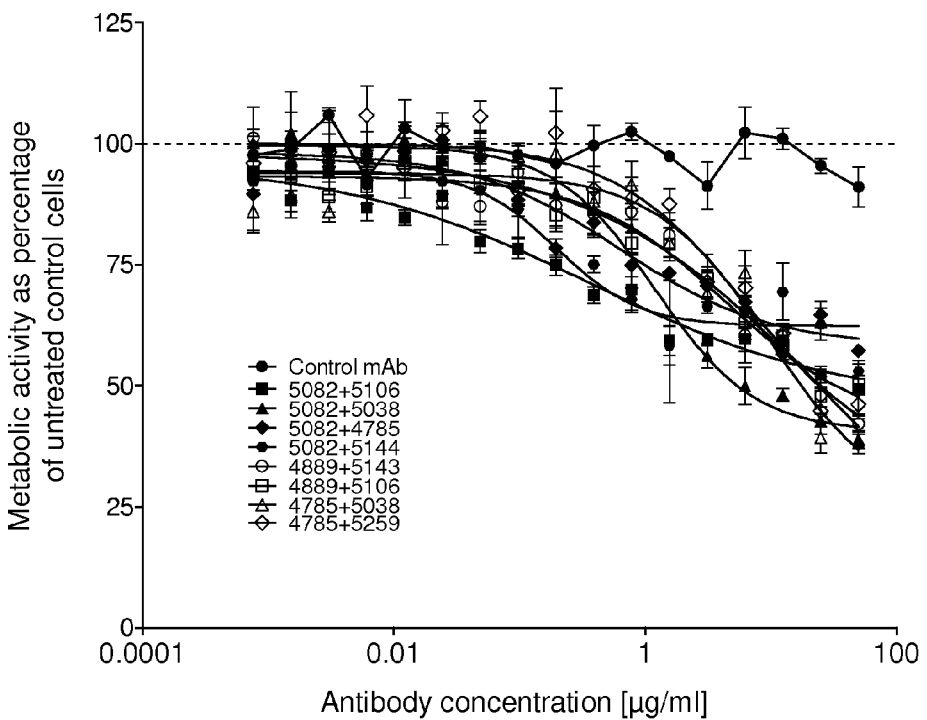
Figure 14:
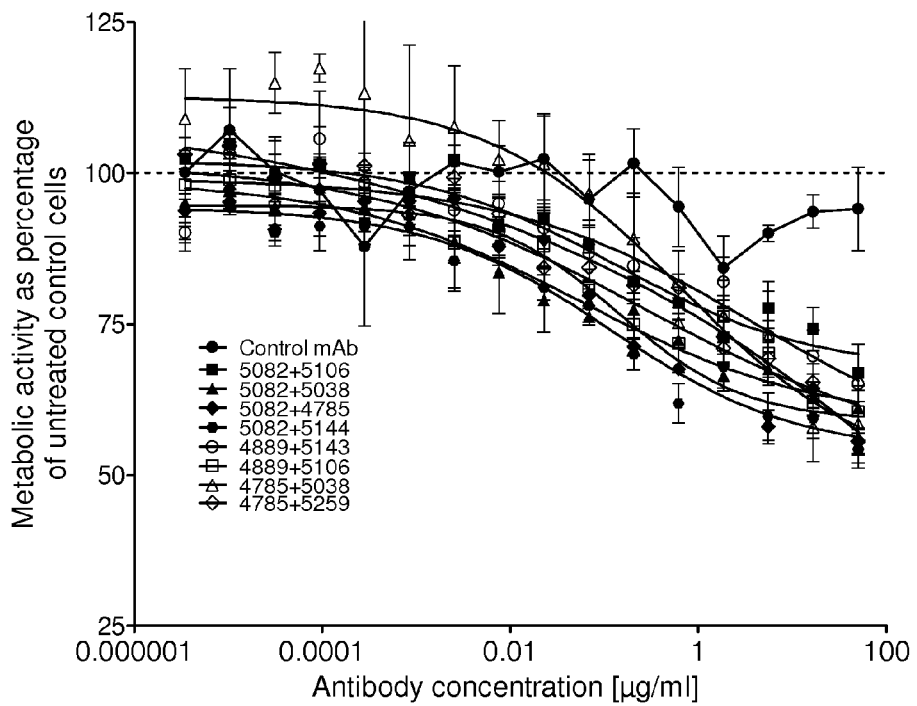
Figure 15:
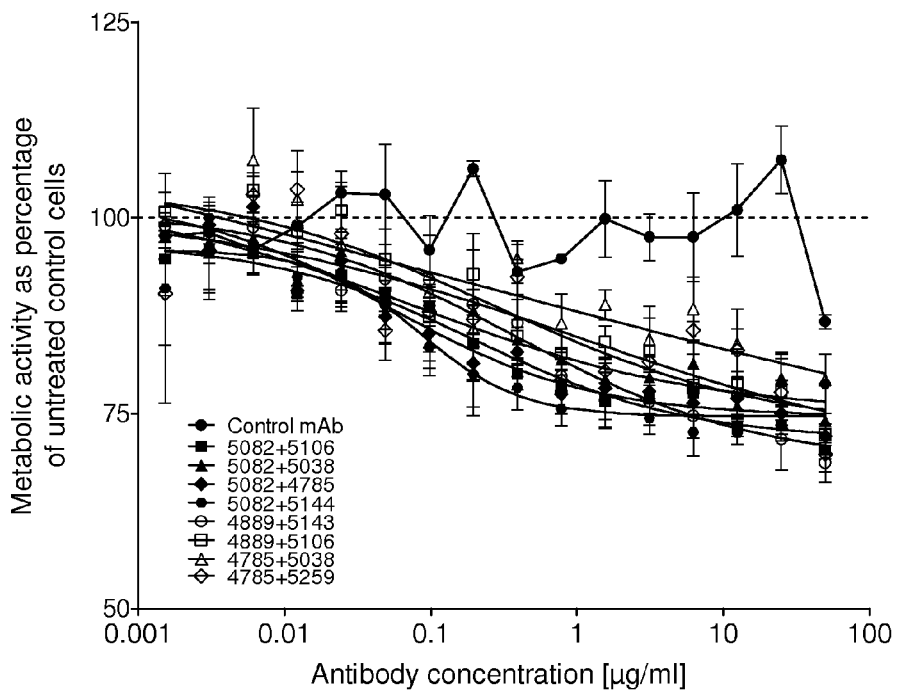

FIGS. 12-15 show the metabolic activity of selected mixtures of anti-HER3 antibodies (the mixtures highlighted in bold in the table above) in the four different cell lines. FIG. 12 shows the metabolic activity in the MDA-MB-175 cell line, FIG. 13 shows activity in the A431NS cell line in the presence of 1 µg/ml Sym004, FIG. 14 shows the activity in the MCF7 cell line in the presence of nM Heregulin beta, and FIG. 15 shows the activity in the H1437 cell line in the presence of 1 nM Heregulin beta.

Example 5

Functional Characterization of Mixtures of Three Anti-HER3 Antibodies

Figure 16:
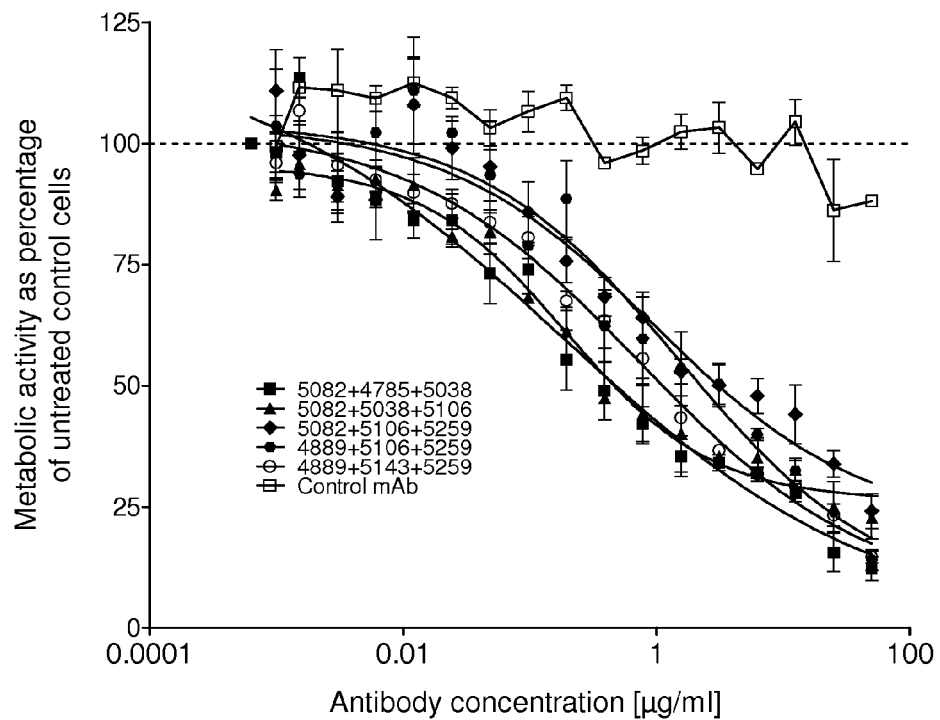
FIGS. 16-19 show the metabolic activity of selected mixtures of three anti-HER3 antibodies in four cancer cell lines.
Figure 17:
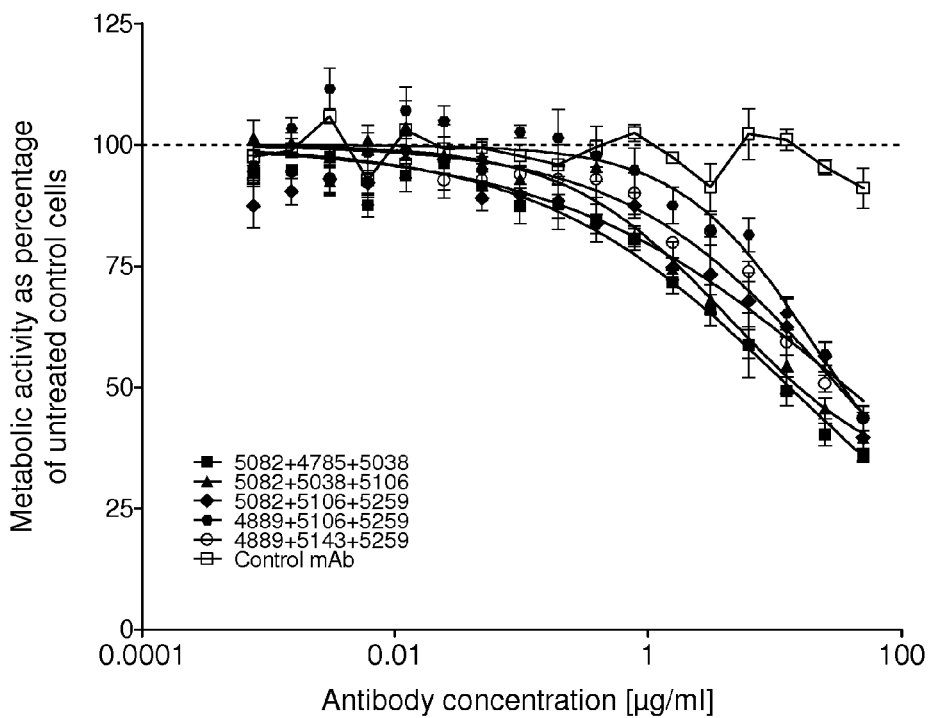
Figure 18:
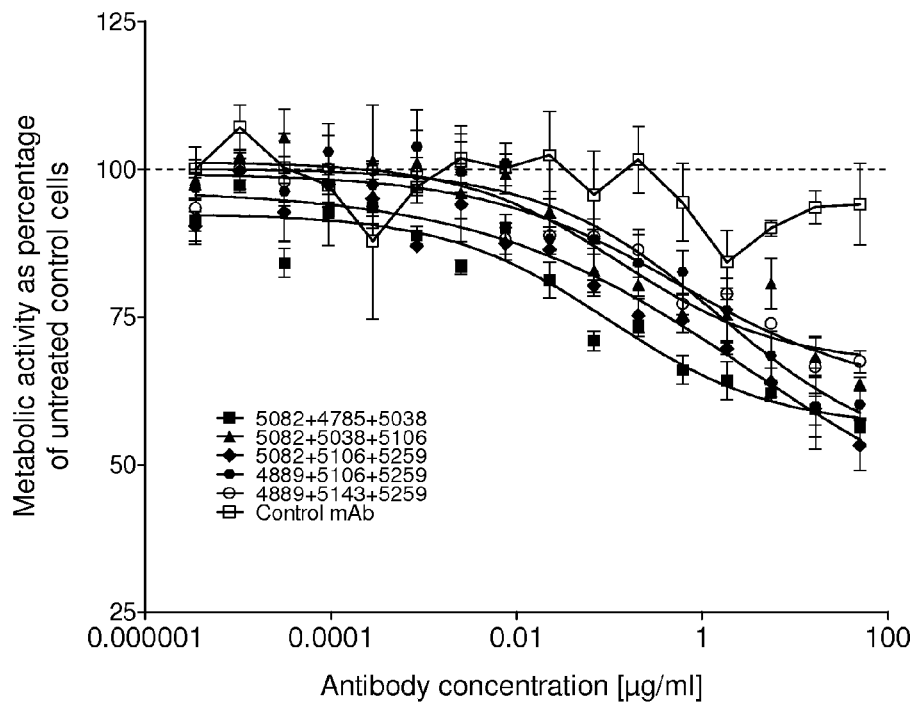
Figure 19:
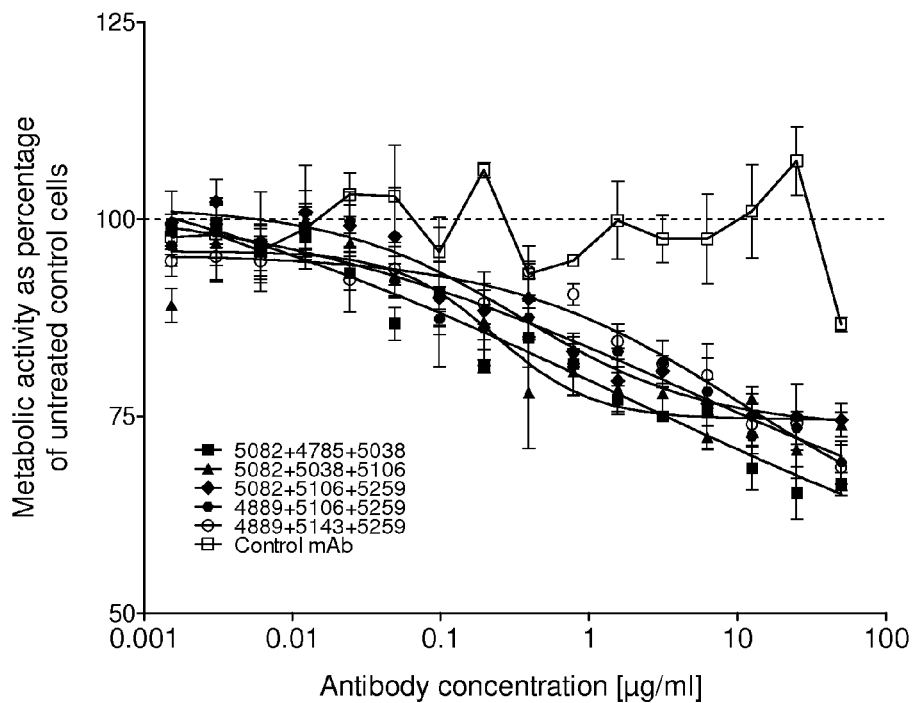

This example describes in vitro testing of mixtures of three antibodies with non-overlapping epitopes and unique bin combinations among selected anti-HER3 antibodies of the invention with confirmed binding to human HER3. The antibody mixtures were evaluated for their ability to inhibit the growth of four different cancer cell lines: MDA-MB-175, MCF7 (+1 nM Heregulin beta), H1437 ((+1 nM Heregulin beta) and A431NS (1 µg/ml of anti-EGFR mixture 992+1024).
Methods
Antibodies 4785, 4889, 5038, 5082, 5106, 5143 and 5259, each of which had confirmed binding to the human HER3 receptor, were tested in mixtures of three antibodies in order to identify antibody mixtures with optimal efficacy. The selected antibodies and antibody mixtures were tested for ability to inhibit the growth and proliferation of the cancer cell lines MDA-MB-175, MCF7 (+1 nM Heregulin beta), H1437 (+1 nM Heregulin beta) and A431NS (1 µg/ml of anti-EGFR mixture 992+1024) using the WST-1 viability assay as described in Example 4.
Results
All the tested mixtures of three antibodies were found to inhibit all four cell lines, although with different potency.
FIGS. 16-19 show the metabolic activity of different mixtures of three anti-HER3 antibodies in the four cancer cell lines. FIG. 16 shows the metabolic activity in the MDA-MB-175 cell line, FIG. 17 shows activity in the A431NS cell line in the presence of 1 µg/ml Sym004, FIG. 18 shows the activity in the MCF7 cell line in the presence of nM Heregulin beta, and FIG. 19 shows the activity in the H1437 cell line in the presence of 1 nM Heregulin beta.

Example 6

Synergistic Inhibition of Cancer Growth by Anti-HER32 Mixtures

This example demonstrates that certain anti-HER3 antibody mixtures synergistically inhibit growth of cancer cells.
Methods
Antibodies 5038, 5082 and 5144, each of which had confirmed binding to the human HER3 receptor, were tested as mixtures of two antibodies, 5038+5082 and 5082+5144, in each case comparing the mixture of two antibodies to the two individual antibodies in the mixture, in order to investigate synergistic inhibition of cell growth. The selected antibodies and antibody mixtures were tested for their ability to inhibit the growth and proliferation of the cancer cell line MDA-MB-175 using the WST-1 viability assay as described in Example 4.

43

Figure 20:
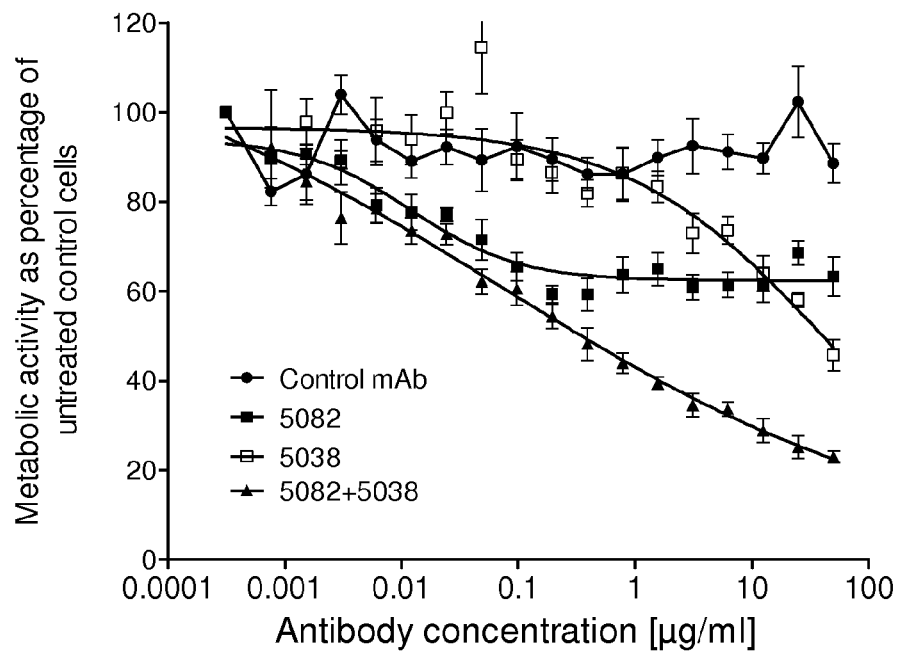
FIGS. 20 and 21 show the growth inhibition activity of two different mixtures of two anti-HER3 antibodies compared to the individual antibodies in the two mixtures in the cancer cell line MDA-MB-175.
Figure 21:
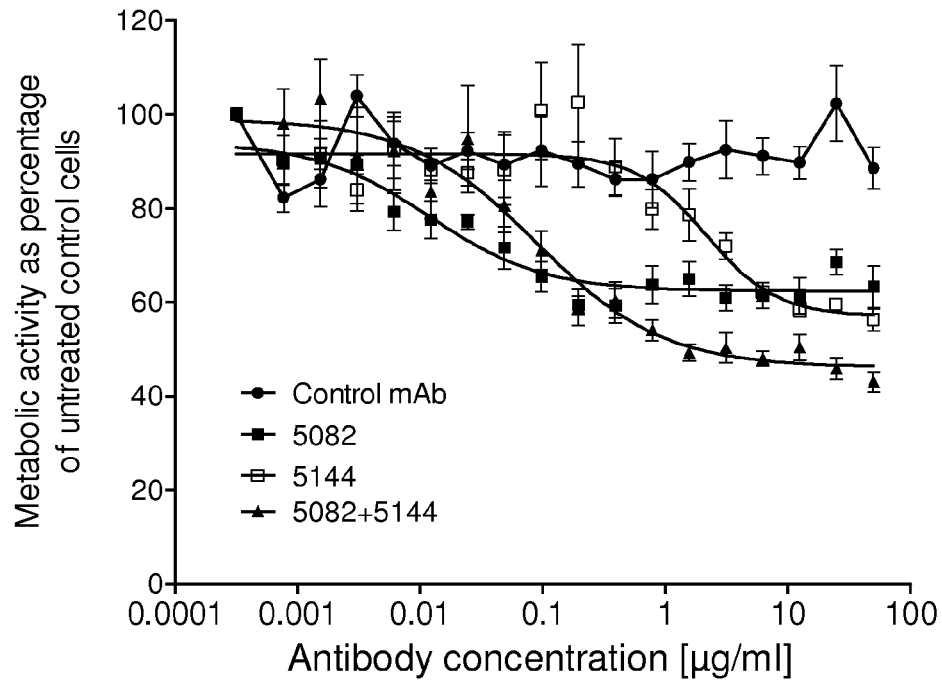

Results
The results show that a mixture of antibodies 5038+5082 or 5082+5144 synergistically inhibit growth of the cancer cell line MDA-MB-175 (FIGS. 20 and 21).

Example 7

Comparison of Anti-HER3 Antibody Mixture and Reference Monoclonal Antibodies

Figure 22:
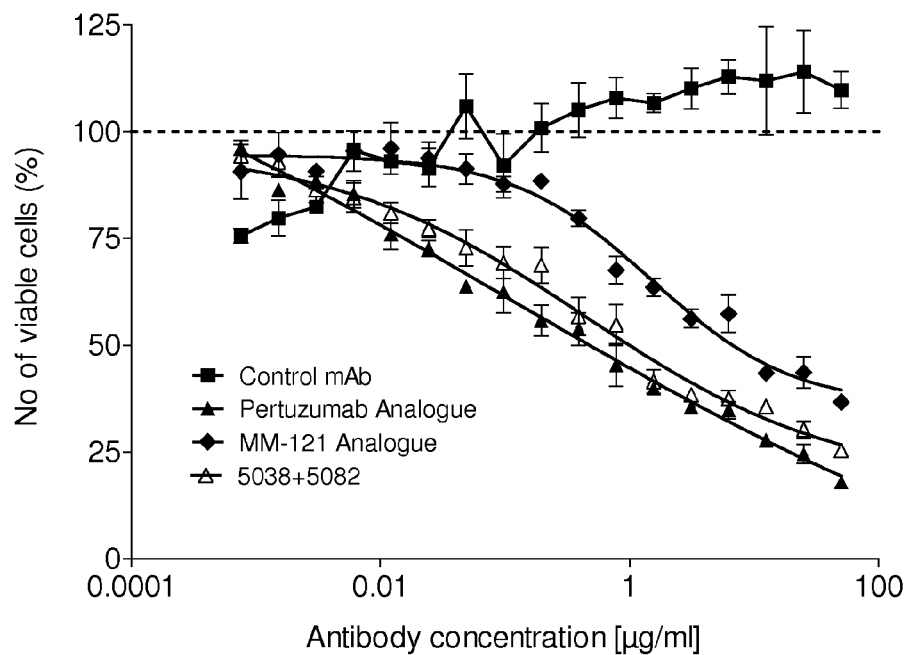
FIGS. 22 and 23 show the growth inhibition activity of a mixture of two anti-HER3 antibodies of the invention compared to the reference antibodies MM-121 (anti-HER3) and pertuzumab (anti-HER2) in the two cancer cell lines MDA-MB-175 and MCF7.
Figure 23:
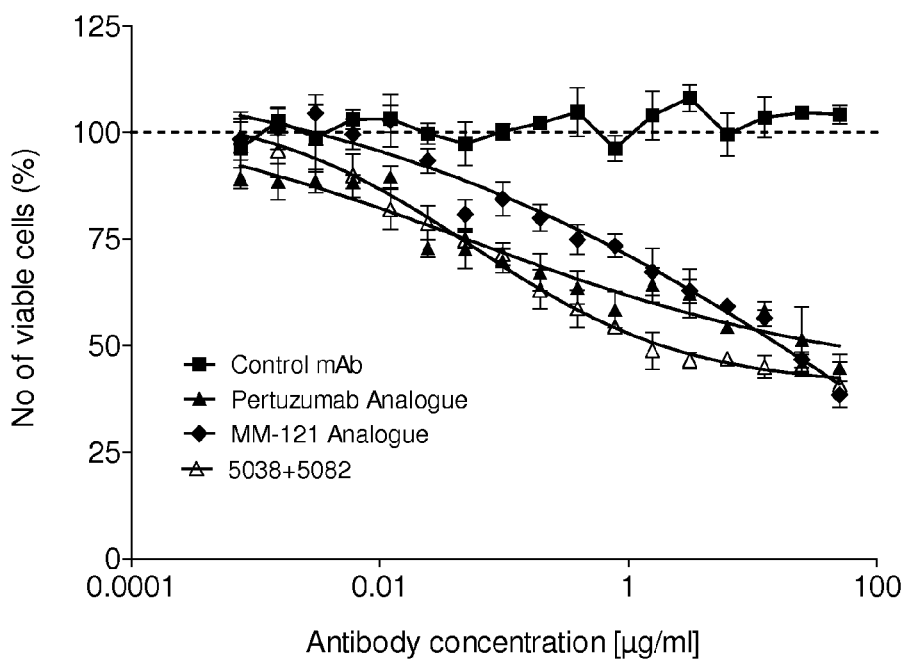

This example describes an in vitro comparison of an anti-HER3 antibody mixture (5038+5082) and analogues of the reference antibodies pertuzumab and MM-121 in the cell lines MDA-MB-175 and MCF-7. Pertuzumab is an anti-HER2 antibody that binds to the dimerization arm of HER2 and blocks HER2/HER3 heterodimerization. The pertuzumab analogue has the light chain and heavy chain amino acid sequences of pertuzumab as disclosed in WO 2006/033700 and US 2006/0121044 A1. MM-121 is an anti-HER3 antibody that blocks heregulin binding to and hence activation of HER3 (see WO 2010/019952 and Schoeberl et al., *Cancer Res*. 70(6):2485-94, March 2010).
Methods
Dose-response curves were generated as described in Example 4. Analogues of the reference anti-HER3 monoclonal antibody MM-121 (Merrimack; sequence disclosed in WO 2008/100624) and the reference anti-HER2 antibody pertuzumab (also known as Omnitarg™, 2C4 and R-1273; sequence disclosed in US 2006/121044 A1) were generated by synthesizing the whole lambda light chain (MM-121) or kappa light chain (pertuzumab) of the respective antibodies without signal peptide, adding flanking NheI and NotI restriction sites, and cloning into an expression vector for transient expression in HEK 293 cells. The heavy chain VH regions of the respective antibodies were synthesized without signal peptide, after which AscI and XhoI sites were added, and the resulting sequences were cloned into the same expression vectors used for light chain expression, which also contained sequences encoding the three constant IgG heavy chain domains CH1, CH2 and CH3. The vectors included a pair of CMV promoters in head-to-head orientation for expression of the two chains of each antibody.
Results
The results show that the antibody mixture 5038+5082 is superior to the reference antibody MM-121 at inhibiting the growth of the two cancer cell lines MDA-MB-175 and MCF7. No apparent superiority of 5038+5082 over pertuzumab was found using these cell lines. The metabolic activity in MDA-MB-175 cells is shown in FIG. 22, and the metabolic activity in MCF7 cells in the presence of 1 nm Heregulin beta is shown in FIG. 23.

Example 8

Anti-HER3 Antibody Mixture Induces HER3 Degradation

Figure 24:
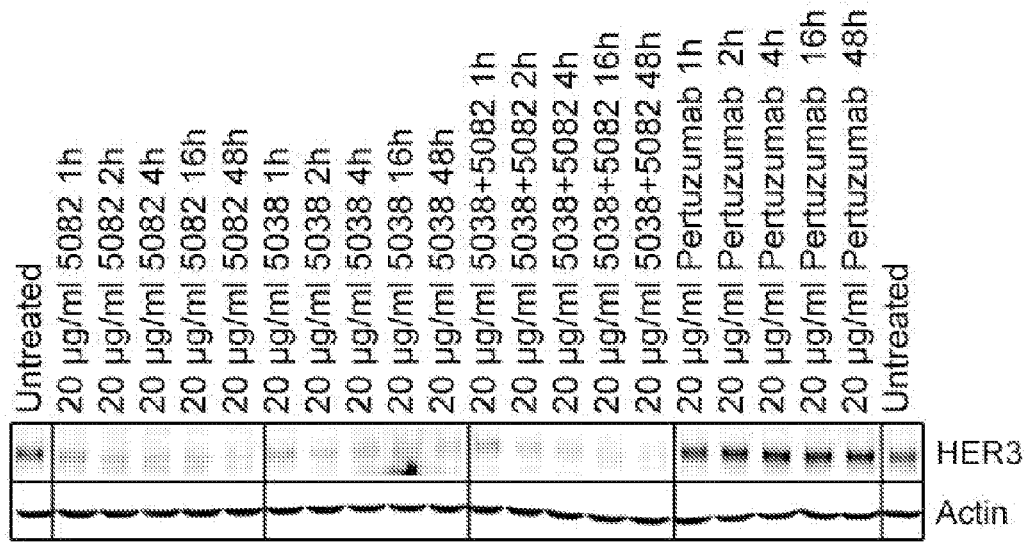
FIG. 24 is a western blot showing HER3 levels at various times in whole cell lysates of OVCAR-8 cells treated with the individual anti-HER3 antibodies 5082 or 5038 or a mixture of the two antibodies.

This example demonstrates that a mixture of two anti-HER3 antibodies is able to induce more efficacious HER3 degradation compared to individual anti-HER3 antibodies. A pertuzumab analogue was also tested in this study.
Methods
In order to investigate the levels of HER3 in cell lines treated with anti-HER3 antibodies, western blot analyses were performed on whole cell lysates of OVCAR-8 cells treated with antibodies for various times. Cells were grown in T-75 culture flasks and at 80% confluency the culture media was removed, the cells washed in 1×PBS and treated with 20 µg/ml of the antibodies diluted in 5 ml medium containing 0.5% FBS. Cells were treated for 1, 2, 4, 16 or 48 hours after which whole cell lysates were prepared using standard RIPA buffer. The total protein concentration was determined in each sample and 10 µg protein analyzed by western blotting using primary antibody against HER3.
Results
Results from the investigation of HER3 levels (FIG. 24) demonstrated that both the individual antibodies and the mixture induced rapid HER3 degradation. However, the anti-HER3 mixture induced a higher level of HER3 degradation compared to the individual antibodies. The pertuzumab analogue was not able to induce HER3 degradation, which was expected given that it binds to HER2 and not to HER3.

Example 9

Anti-HER3 Antibody Mixture Inhibits HER3 Signaling

Figure 25:
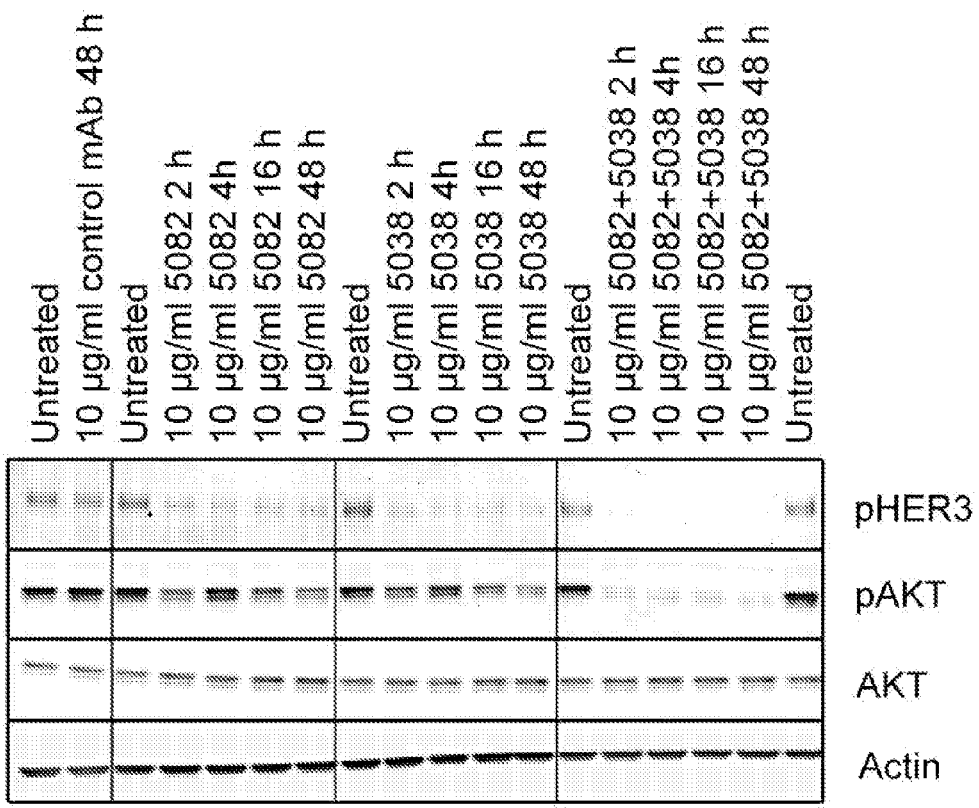
FIG. 25 is a western blot performed on whole cell lysates of MDA-MB-175 cells, showing inhibition of phosphorylation of HER3 and AKT at various times by the individual anti-HER3 antibodies 5082 or 5038 or a mixture of the two antibodies.

This example demonstrates that a mixture of two anti-HER3 antibodies is able to induce more efficacious suppression of HER3 phosphorylation and downstream signaling than individual antibodies.
Methods
In order to investigate the levels of HER3 phosphorylation and downstream signaling, cell lines were treated with anti-HER3 antibodies for various times, and western blot analyses were performed on whole cell lysates. MDA-MB-175 cells were grown in T-75 culture flasks and at 80% confluency the culture media was removed, after which the cells were washed in 1×PBS and treated with 10 µg/ml of the antibodies diluted in 5 ml medium containing 0.5% FBS. Cells were treated for 2, 4, 16 or 48 hours after which whole cell lysates were prepared using standard RIPA buffer. The total protein concentration was determined in each sample and 10 µg of protein was analyzed by western blotting using primary antibodies against pHER3, pAKT(Ser465), AKT and Actin respectively.
Results
Results from the investigation of HER3 signaling (FIG. 25) demonstrated that both the individual antibodies and the mixture induced rapid inhibition of HER3 and AKT phosphorylation. However, the anti-HER3 mixture was superior to the individual antibodies at inhibiting HER3 and AKT phosphorylation.

Example 10

In Vivo Efficacy of Anti-HER3 Mixtures

To evaluate the in vivo efficacy of the anti-HER3 monoclonal antibodies 5038 and 5082 and the mixture of 5038+5082 the compounds were tested in the A549 lung cancer xenograft model.
Methods
$2\times10^6$ A549 cells were inoculated subcutaneously into the left flank of eight to ten week old female athymic nude mice. Tumors were measured twice weekly with calipers and tumor volume in $mm^3$ was calculated according to the formula: $(width)^2 \times length \times 0.5$. At an average tumor size of 115 $mm^3$ the mice were randomized and treatment was initiated. The mice were treated with twice weekly intraperitoneal injections of 50 mg/kg 5038, 5082 or 5038+5082 for five weeks (10 injections in total) followed by an observation period. The experiment included the anti-EGFR monoclonal antibody cetuximab (as an isotype control) and a vehicle control that were each dosed and administered following the same schedule as for the anti-HER3 antibodies.

Results

Figure 26:
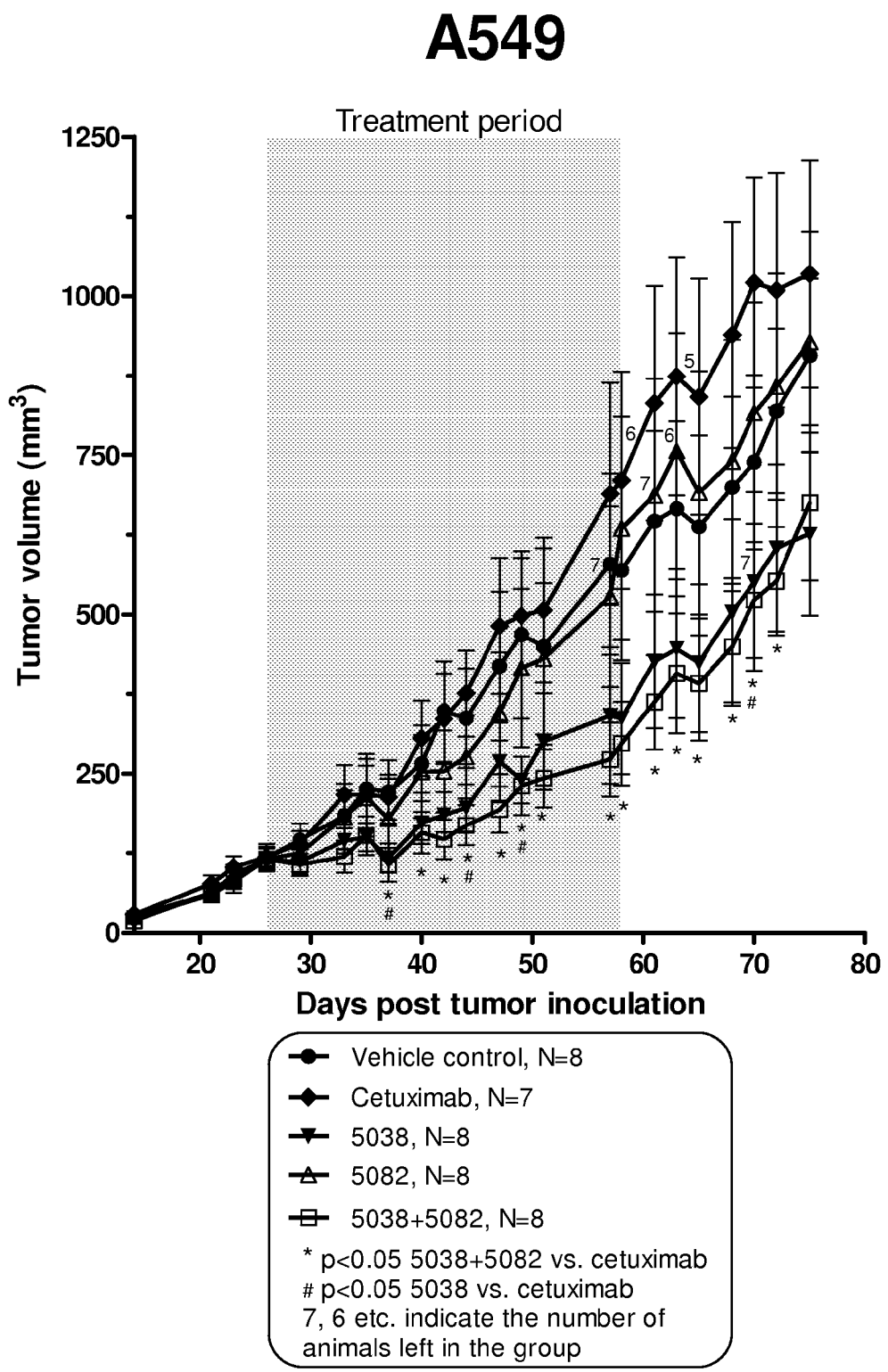
FIG. 26 shows the in vivo efficacy of the individual anti-HER3 antibodies 5038 and 5082 and the mixture of 5038+5082 in the A549 lung cancer xenograft model.
Figure 27:
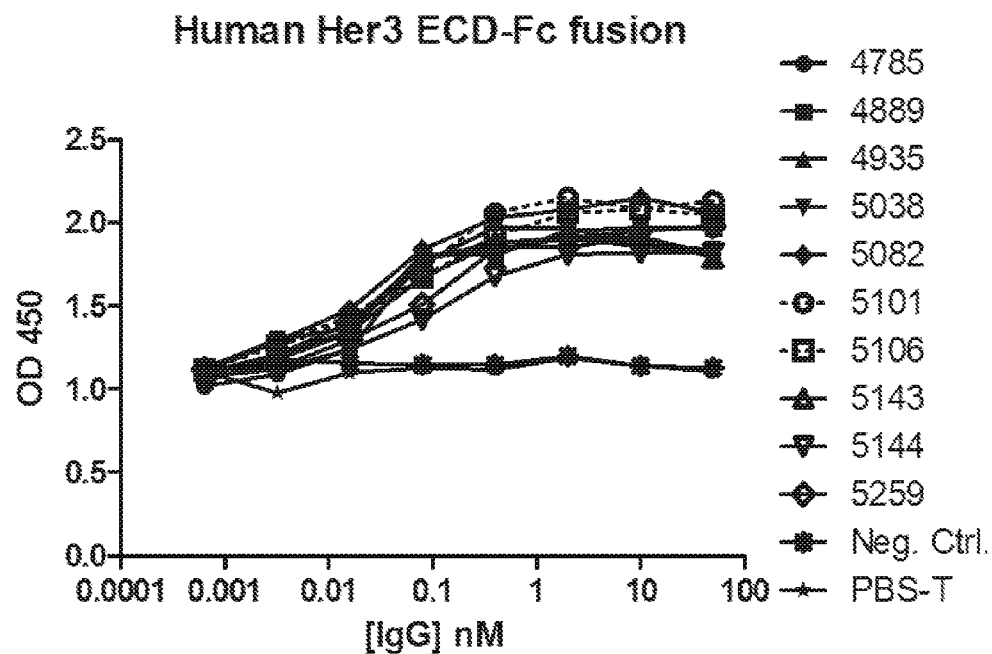
FIGS. 27-32 show the results of a domain mapping of anti-HER3 antibodies by titration of the antibodies and negative controls against coated HER3 antigens.
Figure 28:
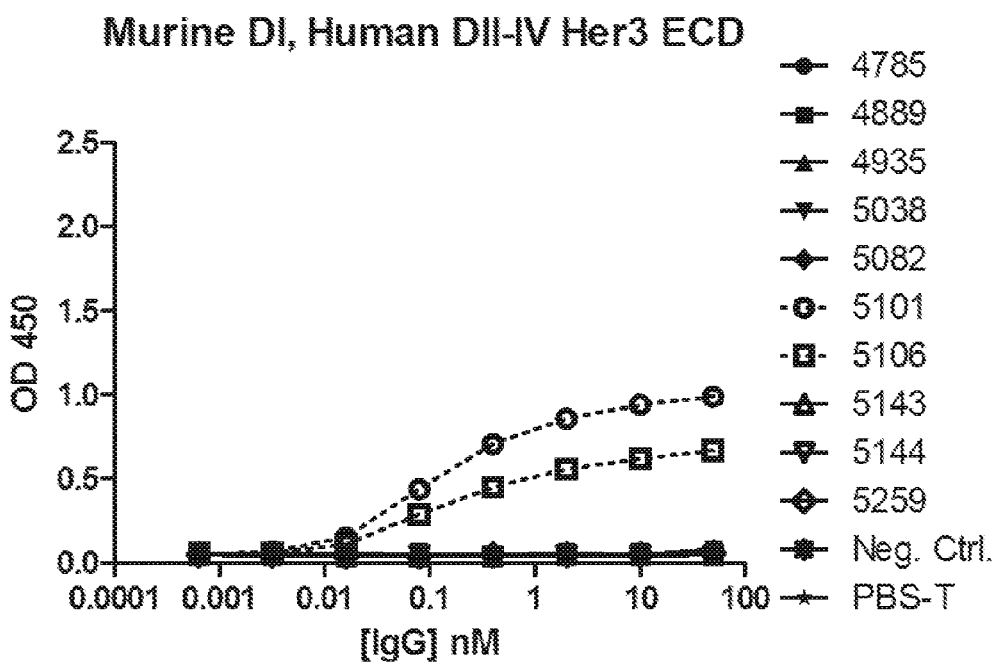
Figure 29:
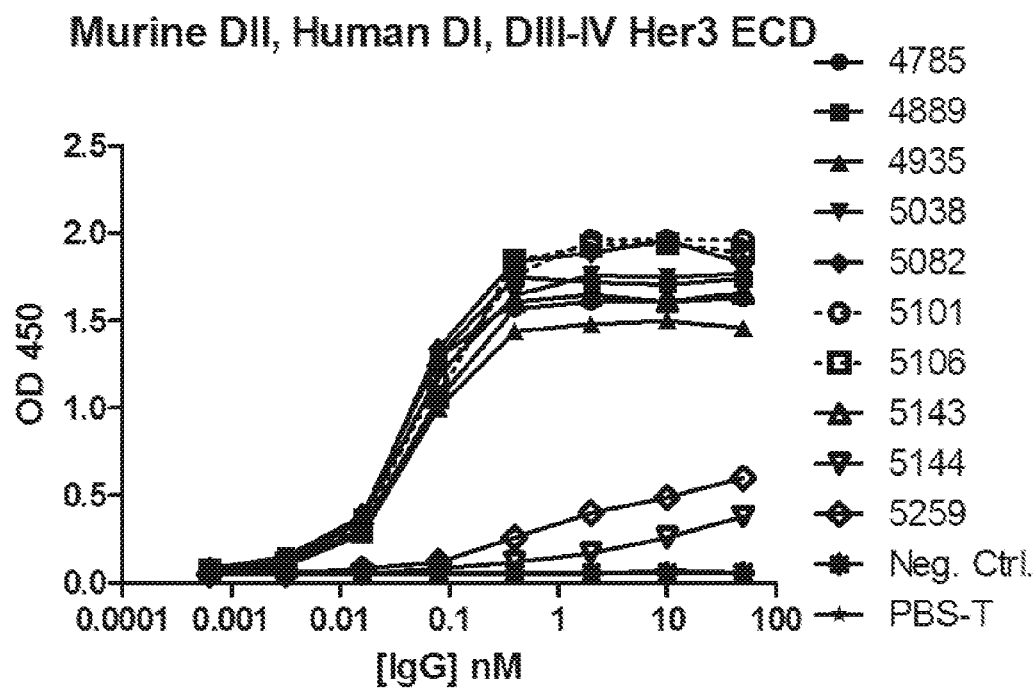
Figure 30:
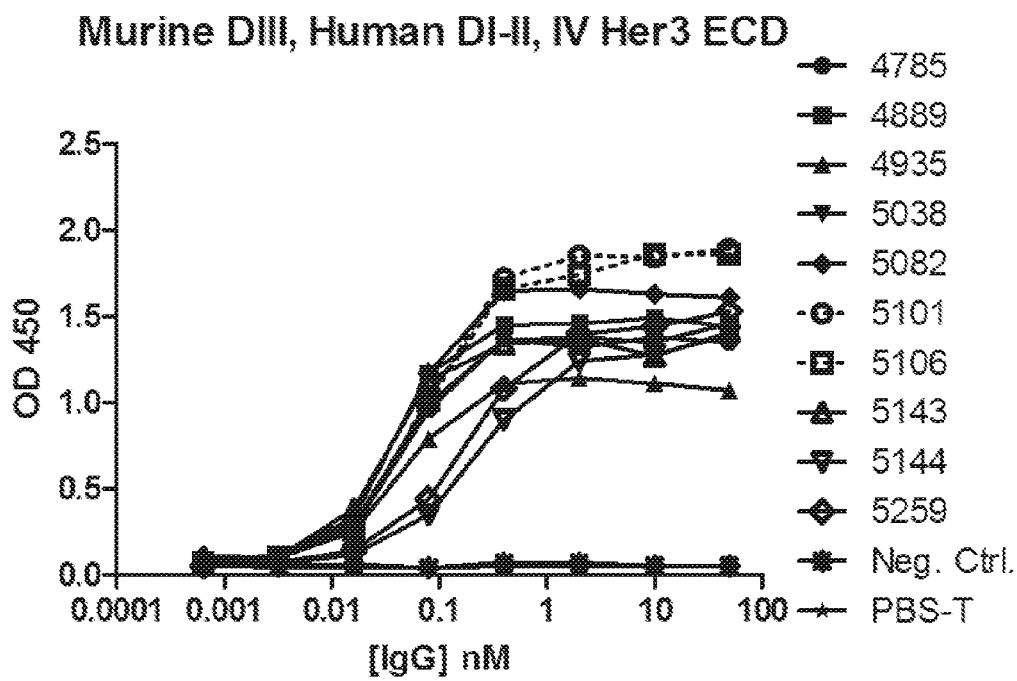
Figure 31:
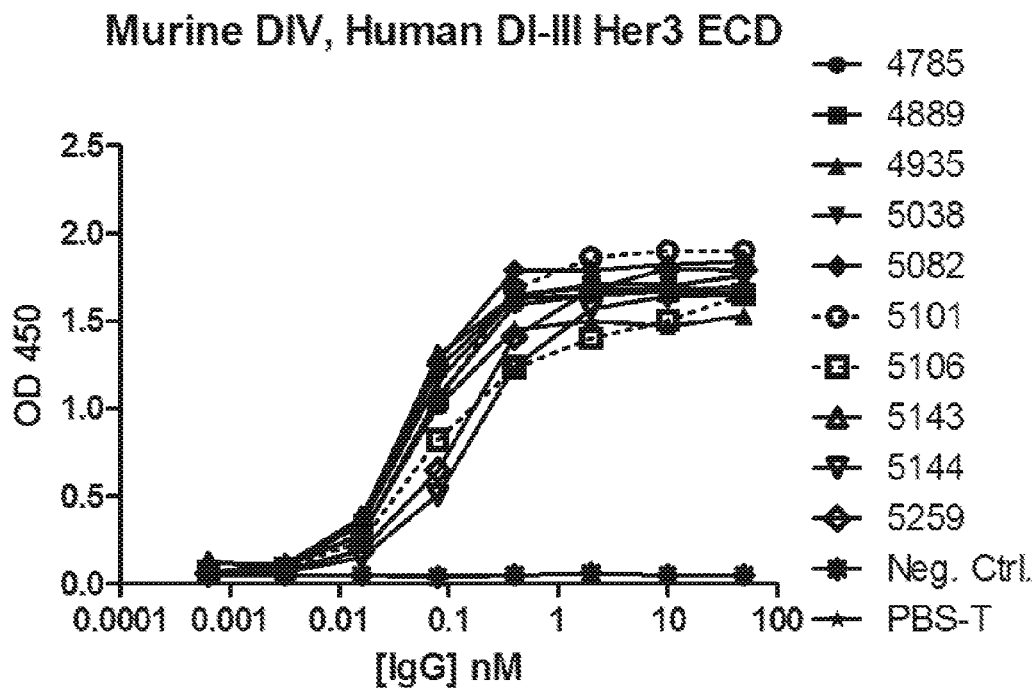
Figure 32:
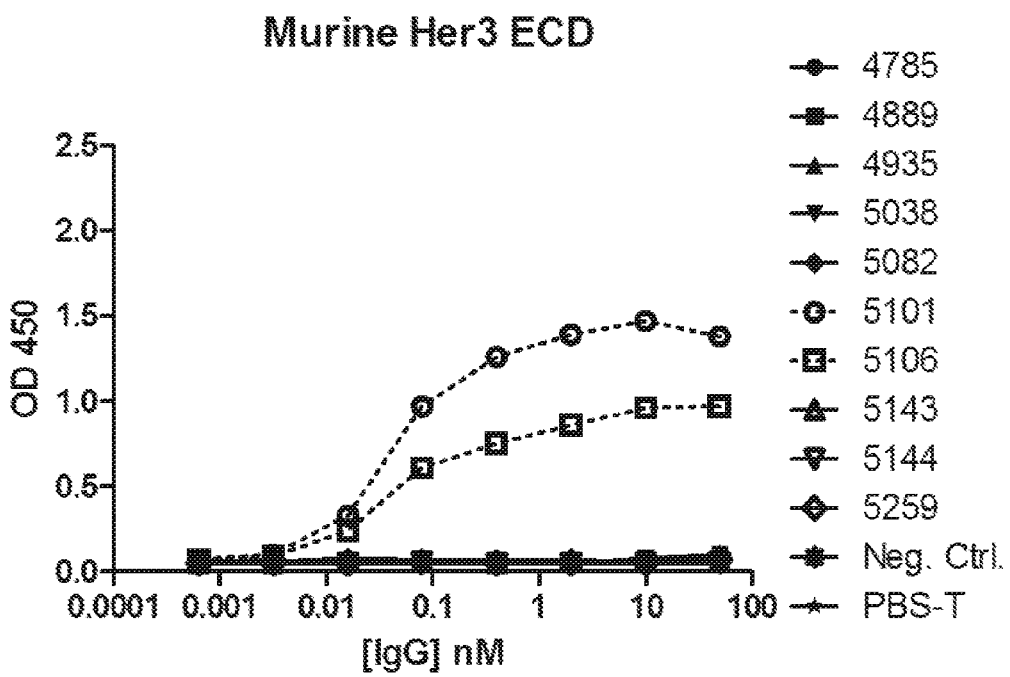

The results of this study are shown in FIG. 26, where it is seen that in mice treated with 5038 or the combination of 5038+5082 tumor growth was controlled in response to treatment from day 26 (treatment start) until day 37. After this point, the tumors in the two groups started growing, although growth was slower compared to tumors in the cetuximab or vehicle control groups. While the results after this point are not statistically significant, there is a clear tendency that tumors in the 5038 and 5038+5082 treated groups grow slower compared to tumors in the control group as well as groups receiving cetuximab or 5082. Mice treated with 5082 alone or with cetuximab did not respond to treatment and showed tumor growth kinetics similar to the vehicle control group.

In summary, the results suggest that 5038 and the combination of 5038+5082 were better at controlling the growth of the A549 tumor xenografts compared to treatment with 5082 alone, cetuximab or the vehicle control.

Example 11

Mapping of Anti-HER3 Antibodies to Individual HER3 Domains

This example demonstrates that the generated panel of anti-HER3 antibodies with functional activity is directed against HER3 extracellular domain (ECD) domain I or domain II as shown by the binding profile to human/mouse chimeric receptor constructs.

Methods

Because the anti-HER3 antibody panel was raised in mice, antibodies are not expected to recognize epitopes present on murine HER3 due to the concept of "self tolerance". Consequently, chimeric receptor constructs in which the human sequences coding for individual domains are replaced by murine sequences can be employed for epitope mapping purposes, since the antibodies are not expected to bind the murines sequence inserted in the human HER3 construct. Human and murine HER3 mRNA sequences (accession number M29366 and NM_010153.1 respectively) were downloaded from NCBI, and extracellular domains I-IV were assigned as described by Kani et al. (*J. Biol. Chem.* (2005) 280:8238-8247). Chimeric human/murine domain exchange variants, in which each of the four human extracellular HER3 domains were replaced by the respective murine DNA sequence, were provided with an N-terminal histidine tag, gene synthesized and transiently expressed in Hek 293 cells. A fully human and a murine ECD construct were used as positive and negative controls, respectively. Supernatants from the transiently expressed receptor constructs were purified by histidine tag affinity chromatography using nickel NTA columns, and purified proteins were coated in ELISA plates at 1 µg/ml in carbonate buffer overnight. The next day wells were blocked with 1% BSA/PBS-T and titrations of antibodies diluted in blocking buffer were added. Finally, wells were washed, and the ELISA was developed by addition of mouse anti-human IgG Fc conjugated to HRP followed by wash and addition of TMB substrate.

Results

Antibodies 5101 and 5106 were found to have broken tolerance in the course of immunization and reacted against murine HER3 (FIGS. 27-32). But because 5101 and 5106 have lower ELISA optical density (OD) values on the murine DI—human DII-IV HER3 construct (i.e. a construct with murine domain I and human domains II-IV) than on other chimeric constructs in which domain I has a human sequence, it can be concluded that these two antibodies bind epitopes located within domain I (DI) of human HER3. Antibodies 5144 and 5259 did not recognize murine DI and bound weakly to murine DII exchange variants. These two antibodies are consequently directed against epitopes overlapping with domain I and II on human HER3. The rest of the antibodies did not recognize the murine DI exchange variant but did bind the other variants and are therefore directed against epitopes on domain I of Human HER3.

The domain mapping of anti-HER3 antibodies is shown in FIGS. 27-32, which is a titration of anti-HER3 antibodies and negative controls against coated HER3 antigens. Bound antibody was detected with an anti-human Fc antibody. High background is observed against human HER3 Fc, due to cross reactivity between the anti-Fc conjugate and the HER3 Fc fusion protein. However, the negative controls clearly demonstrate the difference between the specific and nonspecific binding. Table 7 below provides an overview of the HER3 domains targeted by the different anti-HER3 antibodies.

TABLE 7

Domains targeted by different anti-HER3 antibodies

| mAb | HER3 Domain |
| --- | --- |
| 4785 | DI |
| 4889 | DI |
| 4935 | DI |
| 5038 | DI |
| 5082 | DI |
| 5101* | DI |
| 5106* | DI |
| 5143 | DI |
| 5144 | DI/DII |
| 5259 | DI/DII |

*Antibodies cross-reacting between human and mouse HER3 ECD

Example 12

Epitope Binning of Anti-HER3 Antibodies by Surface Plasmon Resonance

This example demonstrates how pairs of anti-HER3 antibodies with functional activity target at least five non-overlapping epitope bins on domain I or II of HER3 ECD.

Methods

Antibody cross-competition analysis was performed by testing antibody pairs with Surface Plasmon Resonance (SPR) analysis on a Biacore 2000 instrument (GE Healthcare, Denmark). A CM5 sensor chip (GE Healthcare, Denmark) was conjugated with 10,000 Resonance units (RU) of an anti-tetra histidine antibody (Qiagen, Germany) according to the manufacturer's instructions. Histidine-tagged HER3-Fc fusion protein (R&D Systems) was diluted in HBS buffer and captured on an anti-histidine surface at a flow rate of 5 µl/minute. Antibody combinations were evaluated in competitive binding experiments at a saturating concentration of 40 µg/ml by recording the maximum response levels with and without competition. The chip surface was regenerated by injection of 10 mM Glycine-HCl, pH 2.

Results

The 10 anti-HER3 antibodies tested were found to cluster to 5 different non-overlapping epitope bins (FIGS. 33+34).

Epitope bin I contained the three antibodies 4785, 4935 and 5143. Epitope bin II contained antibodies 5082 and 4889, of which mAb 5082 also was found to cross-compete with mAb 5143 from epitope bin 1. Epitope bin III was unique and contained only mAb 5038. Epitope bin IV contained mAbs 5101 and 5106, which also cross-reacted with mouse HER3 protein (Example 11). Finally, epitope bin V contained antibodies 5144 and 5259, which were found to bind similar epitopes present on both DI and DII (Example 11).

FIG. 33 shows a table with the results of epitope binning by antibody cross-competition analysis. The analysis was performed by first saturating HER3 antigen with the antibodies listed at the top, followed by injection the antibodies listed on the left. The numbers in the cells refer to percent competition, calculated as:

(1−(maximal response with competition/maximal response without competition)×100

Figure 34:
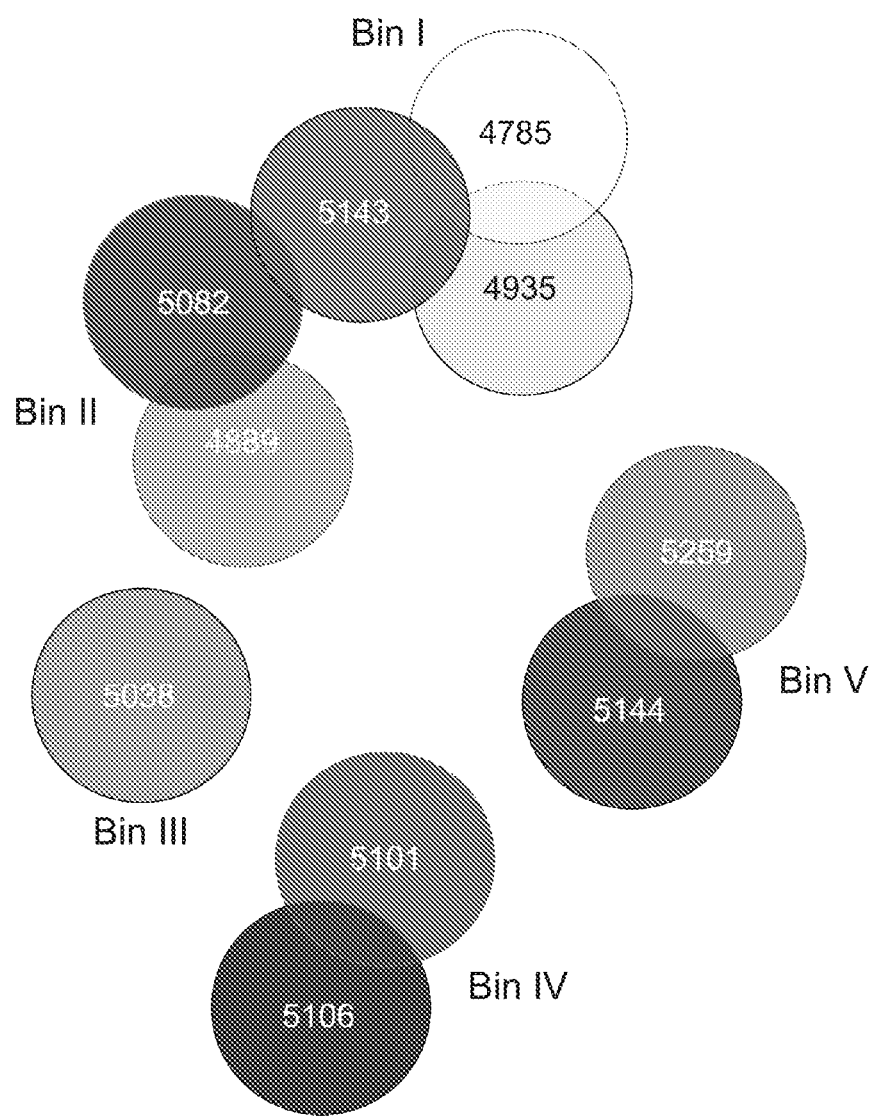
FIG. 34 is a graphic illustration of the relationship between assigned epitope bins for anti-HER3 antibodies, where overlapping circles represent antibodies with overlapping epitopes.

The boxed cells represent antibody pairs that inhibit each other by at least 50%. Antibodies are assigned into epitope bins according to the competition profile; see FIG. 34, which provides a graphic illustration of the relationship between assigned epitope bins, where overlapping circles represent antibodies with overlapping epitopes.

Example 13

In Vivo Efficacy of Anti-HER3 Mixtures

To evaluate the in vivo efficacy of the anti-HER3 monoclonal antibodies 5038 and 5082 and the mixture of 5038+5082 we tested the compounds in the BxPC3 pancreatic cancer xenograft model.

Methods $5 \times 10^6$ BxPC3 cells were inoculated subcutaneously into the left flank of eight to ten week old female athymic nude mice. Tumors were measured twice weekly with calipers and tumor volume in $mm^3$ was calculated according to the formula: $(width)^2 \times length \times 0.5$. At an average tumor size of 165 $mm^3$ the mice were randomized and treatment was initiated. The mice were treated with twice weekly intraperitoneal injections of 50 mg/kg 5038, 5082 or a mixture of 5038+5082 for 3 weeks (6 injections in total) followed by an observation period. The experiment included a vehicle control, which was dosed and administered following the same schedule as described for the anti-HER3 antibodies above.

Results

Figure 35:
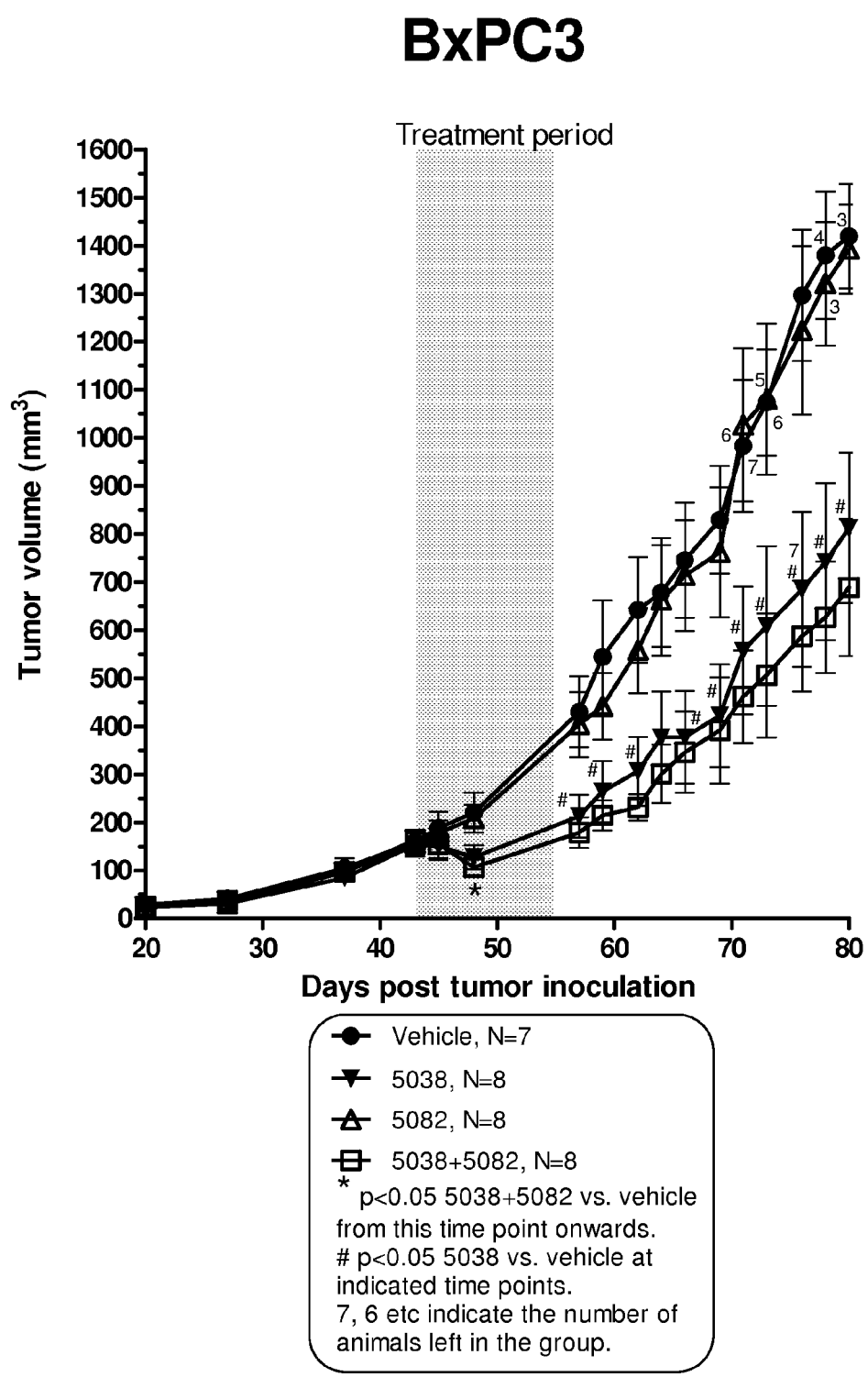
FIG. 35 shows the in vivo efficacy of the anti-HER3 monoclonal antibodies 5038 and 5082 and the mixture of 5038+5082 in the BxPC3 pancreatic cancer xenograft model, expressed as tumor volume.

In mice treated with 5038 or the combination of 5038+5082 the tumor growth were inhibited significantly better compared to mice in the vehicle control group (FIG. 35). In mice treated with 5038+5082 a significant difference compared to the vehicle control group was observed as early as five days after the first treatment and lasted throughout the study period. Mice treated with 5038 were significantly better at controlling tumor growth compared to vehicle control treated animals from day 57 and, with the exception of one day (day 64), this was observed throughout the study period.

Figure 36:
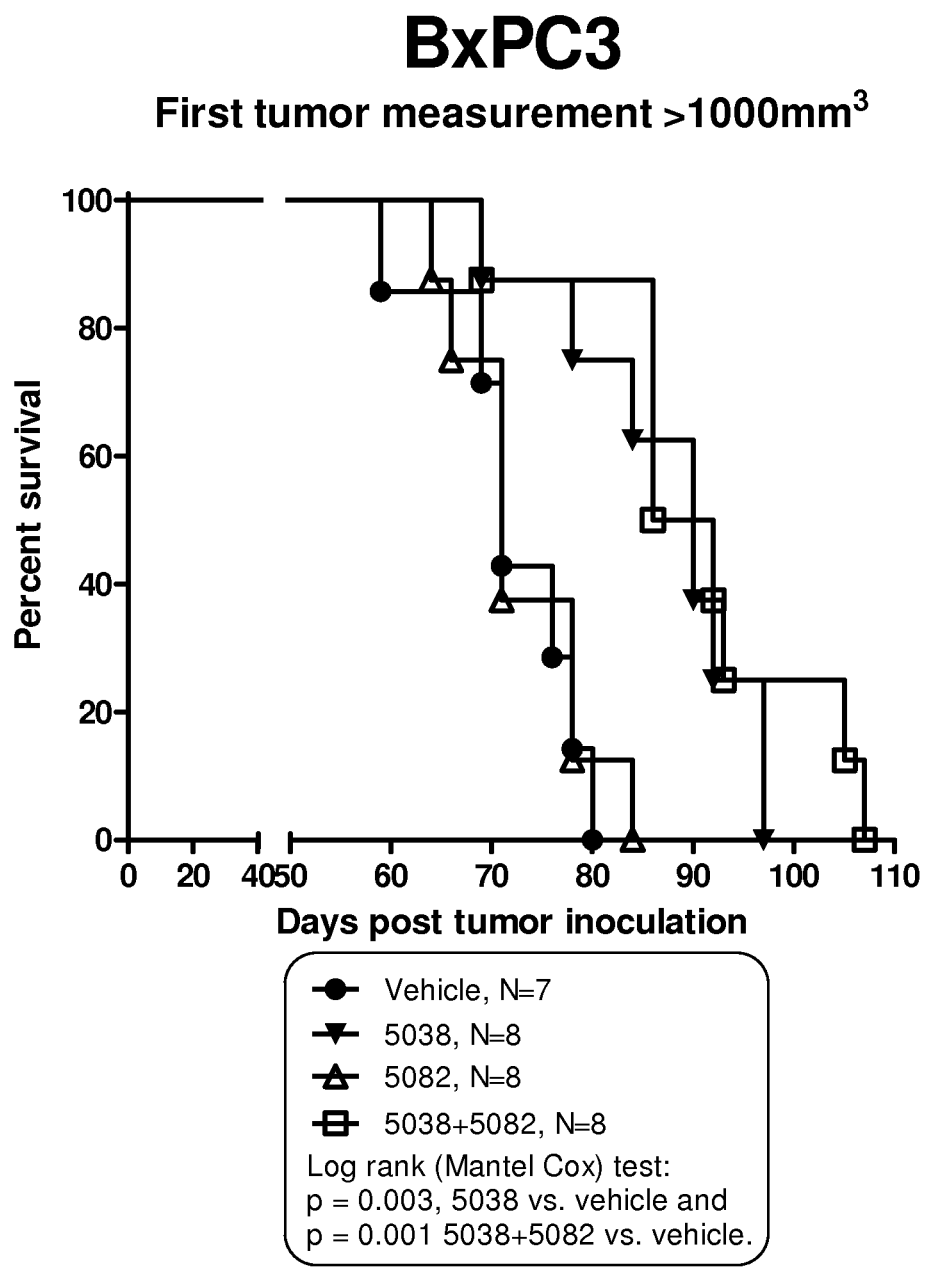
FIG. 36 shows the in vivo efficacy of the anti-HER3 monoclonal antibodies 5038 and 5082 and the mixture of 5038+5082 in the BxPC3 pancreatic cancer xenograft model, expressed as percent survival.

The effective inhibition of tumor growth by 5038 and the combination of 5038+5082 could also be observed by looking at survival. Both of these treatments were significantly better compared to the vehicle control group as calculated by a Log rank (Mantel Cox) test with a p-value of 0.003 for 5038 and 0.001 for 5038+5082 (FIG. 36).

In summary, 5038 and the combination of 5038+5082 were significantly better at inhibiting tumor growth and improve survival of animals with BxPC3 tumor xenografts compared to vehicle control.

The invention claimed is:

1. An antibody composition comprising at least a first anti-human HER3 antibody molecule and a second anti-human HER3 antibody molecule distinct from the first molecule, or humanized variants of said first and second antibody molecules, wherein:
    the first anti-human HER3 antibody molecule comprises the heavy chain CDR1-3 in SEQ ID NO: 18 and the light chain CDR1-3 in SEQ ID NO: 20; and
    the second anti-human HER3 antibody molecule comprises the heavy chain CDR1-3 in SEQ ID NO: 14 and the light chain CDR1-3 in SEQ ID NO: 16.

2. The antibody composition of claim 1, wherein
    the first anti-human HER3 antibody molecule comprises the heavy chain variable domain (VH) amino acid sequence in SEQ ID NO: 18 or a humanized variant thereof and the light chain variable domain (VL) amino acid sequence in SEQ ID NO: 20 or a humanized variant thereof; and
    the second anti-human an HER3 antibody molecule comprises the VH amino acid sequence in SEQ ID NO: 14 or a humanized variant thereof and the VL amino acid sequence in SEQ ID NO: 16 or a humanized variant thereof.

3. An antibody composition comprising:
    an anti-human HER3 antibody molecule comprising the amino acid sequences of SEQ ID NOs: 18 and 20 or humanized variants thereof, and
    an anti-human HER3 antibody molecule comprising the amino acid sequences of SEQ ID NOs: 14 and 16 or humanized variants thereof.

4. The antibody composition of claim 1 or 3, wherein at least one anti-human HER3 antibody molecule in said composition is an immunoconjugate comprising an anti-human HER3 antibody conjugated to an anti-cancer agent.

5. The antibody composition of claim 4, where the anti-cancer agent is selected from the group consisting of cytotoxic agents, cytokines, toxins and radionuclides.

6. A polyclonal cell line that expresses the antibody composition according to claim 1 or 3, wherein said polyclonal cell line comprises host cells each expressing an anti-human HER3 antibody of the composition.

7. A method for producing the anti-human HER3 antibody composition according to claim 1 or 3, comprising providing host cells each capable of expressing an anti-human HER3 antibody molecule of the composition, cultivating said host cells under conditions suitable for expression of the antibody molecules, and isolating the resulting antibody molecules.

8. The method of claim 7, wherein the host cells are cultured in a single bioreactor.

9. A pharmaceutical composition comprising the anti-human HER3 antibody composition according to claim 1 or 3 and a pharmaceutically acceptable excipient.

10. A method for treating cancer in a patient characterized by overexpression of HER3, comprising administering to the patient the antibody composition according to claim 1 or 3.

11. A method for treating a patient with a disorder characterized by overexpression of HER3, comprising administering to the patient the antibody composition according to claim 1 or 3.

12. The method of claim 10 or 11, wherein the patient is human.

13. A method for reducing heterodimer formation between HER3 and another ErbB family receptor in cells that express HER3, comprising contacting said cells with the antibody composition according to claim 1 or 3.

14. A method for inducing internalization of HER3 on the surface of cells that express HER3, comprising contacting said cells with the antibody composition according to claim 1 or 3.

* * * * *

SEQUENCE LISTING

<160> NUMBER OF SEQ ID NOS: 83

<210> SEQ ID NO 1
<211> LENGTH: 354
<212> TYPE: DNA
<213> ORGANISM: Mus musculus
<220> FEATURE:
<221> NAME/KEY: misc_feature
<223> OTHER INFORMATION: Ab 4785 VH DNA

<400> SEQUENCE: 1

```
gaggtccaac tgcaacagtc tggaccagaa ctggtgatgc ctggggcttc agtgaagata      60
tcctgcaagg cttctggcta cagcttcaca agctactatg tacactgggt gaagcagagg     120
cctggacagg gacttgagtg gattggatgg atttatcctg gaagtggtca tactaagtac     180
aatgagaagt tcaaggacaa ggccacactg acggcagaca tcctccag cactgcctac       240 atgcaactca gcagcctaac atctgaggac tctgcggtct attactgtgc aagaccccc      300 tactatagta actacgccga tgtctggggc acaggaccac cggtcaccgt ctcg           354
```

<210> SEQ ID NO 2
<211> LENGTH: 118
<212> TYPE: PRT
<213> ORGANISM: Mus musculus
<220> FEATURE:
<221> NAME/KEY: MISC_FEATURE
<223> OTHER INFORMATION: Ab 4785 VH

<400> SEQUENCE: 2

Glu Val Gln Leu Gln Gln Ser Gly Pro Glu Leu Val Met Pro Gly Ala
1               5                   10                  15

Ser Val Lys Ile Ser Cys Lys Ala Ser Gly Tyr Ser Phe Thr Ser Tyr
                20                  25                  30

Tyr Val His Trp Val Lys Gln Arg Pro Gly Gln Gly Leu Glu Trp Ile
            35                  40                  45

Gly Trp Ile Tyr Pro Gly Ser Gly His Thr Lys Tyr Asn Glu Lys Phe
    50                  55                  60

Lys Asp Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Pro Pro Tyr Tyr Ser Asn Tyr Ala Asp Val Trp Gly Thr Gly
            100                 105                 110

Thr Thr Val Thr Val Ser
        115

<210> SEQ ID NO 3
<211> LENGTH: 667
<212> TYPE: DNA
<213> ORGANISM: Mus musculus
<220> FEATURE:
<221> NAME/KEY: misc_feature
<223> OTHER INFORMATION: Ab 4785 LC DNA

<400> SEQUENCE: 3
gacattgtga tgactcagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccacaagg     180
gaatctgggg tccctgatcg cttcacaggc agtggatctg gaacagattt cactctcacc     240
atcagcagtg tgcaggctga agacctggca gtttattact gtcagagtga ttatagttat     300
ccgtacacgt tcggagggggg gaccaagctg gaaataaaac gaactgtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaagt ctacgcctgc      600 gaagtcaccc atcagggcct gagctcgccc gtcacaaaga gcttcaacag gggagagtgt     660
taataag                                                              667

<210> SEQ ID NO 4
<211> LENGTH: 220
<212> TYPE: PRT
<213> ORGANISM: Mus musculus
<220> FEATURE:
<221> NAME/KEY: MISC_FEATURE
<223> OTHER INFORMATION: Ab 4785 LC

<400> SEQUENCE: 4

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
                35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Asp Tyr Ser Tyr Pro Tyr Thr Phe Gly Gly Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 5
<211> LENGTH: 351
<212> TYPE: DNA
<213> ORGANISM: Mus musculus
<220> FEATURE:
<221> NAME/KEY: misc_feature
<223> OTHER INFORMATION: Ab 4889 VH DNA

<400> SEQUENCE: 5
gaagtgcagc ttgtggagtc aggacctggc ctcgtgaaac cttctcagtc tctgtctctc      60
acctgctctg tcactggcta ctccatcacc agtgcttatt actggaactg gatccggcag     120
tttccaggaa acaaactgga atggatgggc tacgtaagct acgatggtag caatacctac     180
aacccatctc tcaaaaatcg aatctccatc actcgtgaca catctaagaa ccagtttttc     240
ctgaagttga tttctctgac tactgaggac accgccacat attactgtgc aagagagggg     300
gactatggtt attctgacta ttggggccaa ggcaccactc tcacagtctc g              351

<210> SEQ ID NO 6
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 4889 VH

<400> SEQUENCE: 6

Glu Val Gln Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
                20                  25                  30

Tyr Tyr Trp Asn Trp Ile Arg Gln Phe Pro Gly Asn Lys Leu Glu Trp
                35                  40                  45

```
Met Gly Tyr Val Ser Tyr Asp Gly Ser Asn Thr Tyr Asn Pro Ser Leu
 50                  55                  60
Lys Asn Arg Ile Ser Ile Thr Arg Asp Thr Ser Lys Asn Gln Phe Phe
 65                  70                  75                  80
Leu Lys Leu Ile Ser Leu Thr Thr Glu Asp Thr Ala Thr Tyr Tyr Cys
                     85                  90                  95
Ala Arg Glu Gly Asp Tyr Gly Tyr Ser Asp Tyr Trp Gly Gln Gly Thr
                100                 105                 110
Thr Leu Thr Val Ser
            115

<210> SEQ ID NO 7
<211> LENGTH: 649
<212> TYPE: DNA
<213> ORGANISM: Mus musculus
<220> FEATURE:
<221> NAME/KEY: misc_feature
<223> OTHER INFORMATION: Ab 4889 LC DNA

<400> SEQUENCE: 7
gatattgtga tgacgcagtc tacatcctcc ctgtctgcct ctctgggaga cagagtcacc      60
gtcagttgca gggcaagtca ggacattagc aattatttaa actggtatca gcagaaacca     120
gatggaacta ttaaactcct gatctactac acatcaagat acattcagg agtcccatca      180 aggttcagtg gcagtgggtc tggaacagat tattctctca ccattagcaa cctggaccaa     240
gaagatattg ccacttactt ttgccaacag agtaatacgc ttccgtggac gttcggtgga     300
ggcaccaagc tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg      540 ctgagcaaag cagactacga gaaacacaaa gtctacgcct gcgaagtcac ccatcagggc     600
ctgagctcgc ccgtcacaaa gagcttcaac aggggagagt gttaataag                 649

<210> SEQ ID NO 8
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 4889 LC

<400> SEQUENCE: 8

Asp Ile Val Met Thr Gln Ser Thr Ser Ser Leu Ser Ala Ser Leu Gly
 1               5                  10                  15

Asp Arg Val Thr Val Ser Cys Arg Ala Ser Gln Asp Ile Ser Asn Tyr
                20                  25                  30

Leu Asn Trp Tyr Gln Gln Lys Pro Asp Gly Thr Ile Lys Leu Leu Ile
            35                  40                  45

Tyr Tyr Thr Ser Arg Leu His Ser Gly Val Pro Ser Arg Phe Ser Gly
         50                  55                  60

Ser Gly Ser Gly Thr Asp Tyr Ser Leu Thr Ile Ser Asn Leu Asp Gln
 65                  70                  75                  80

Glu Asp Ile Ala Thr Tyr Phe Cys Gln Gln Ser Asn Thr Leu Pro Trp
                 85                  90                  95

Thr Phe Gly Gly Gly Thr Lys Leu Glu Ile Lys Arg Thr Val Ala Ala
```

```
                    100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 9
<211> LENGTH: 357
<212> TYPE: DNA
<213> ORGANISM: Mus musculus
<220> FEATURE:
<221> NAME/KEY: misc_feature
<223> OTHER INFORMATION: Ab 4935 VH DNA

<400> SEQUENCE: 9
cagatccagt tggtgcagtc tggacctgag ctggtgaagc ctggggcttc agtgaggata      60
tcctgcaagg cttctggcta caccttcaca agctactata tacactgggt gaagcagagg     120
cctggacagg gacttgagtg gattggatgg atttatcctg gaaatgttca tactaagtac     180
actgagaagt tcaagggcaa agccacactg actgcagaca aatcctccag cacagcctac     240
atgcacctca gcagcctgac ctctgaggac tctgcggtct atttctgtgt aagacgatat     300
ggttacgacg gggactggtt tgcttactgg ggccaaggga ctctggtcac tgtctcg       357

<210> SEQ ID NO 10
<211> LENGTH: 119
<212> TYPE: PRT
<213> ORGANISM: Mus musculus
<220> FEATURE:
<221> NAME/KEY: MISC_FEATURE
<223> OTHER INFORMATION: Ab 4935 VH

<400> SEQUENCE: 10

Gln Ile Gln Leu Val Gln Ser Gly Pro Glu Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val His Thr Lys Tyr Thr Glu Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Phe Cys
                85                  90                  95

Val Arg Arg Tyr Gly Tyr Asp Gly Asp Trp Phe Ala Tyr Trp Gly Gln
            100                 105                 110

Gly Thr Leu Val Thr Val Ser
```

<210> SEQ ID NO 11
<211> LENGTH: 661
<212> TYPE: DNA
<213> ORGANISM: Mus musculus
<220> FEATURE:
<221> NAME/KEY: misc_feature
<223> OTHER INFORMATION: Ab 4935 LC DNA

<400> SEQUENCE: 11

```
gatatccaga tgacccaatc tccagcttct ttggctgtgt ctctagggca gagggccacc      60
atatcctgca gagccagtga aagtgttgat agttatggca atacttttat gcactggtac     120
cagcagaaac caggacagcc acccaaactc ctcatctatc gtgcatccaa cctagaatct     180
gggatccctg ccaggttcag tgcagtggg tctaggacag acttcaccct caccattaat      240
cctgtggagg ctgatgatgt tgcaacctat tactgtcagc aaagtaatga ggatccgtgg     300
acgttcggtg gaggcaccaa gctggaaatc aaacgaactg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgttaataa      660
g                                                                      661
```

<210> SEQ ID NO 12
<211> LENGTH: 218
<212> TYPE: PRT
<213> ORGANISM: Mus musculus
<220> FEATURE:
<221> NAME/KEY: MISC_FEATURE
<223> OTHER INFORMATION: Ab 4935 LC

<400> SEQUENCE: 12

```
Asp Ile Gln Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                    165                 170                 175
Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 13
<211> LENGTH: 357
<212> TYPE: DNA
<213> ORGANISM: Mus musculus
<220> FEATURE:
<221> NAME/KEY: misc_feature
<223> OTHER INFORMATION: Ab 5038 VH DNA

<400> SEQUENCE: 13
gaggtgaagc tggttgagtc aggacctggc ctcgtgaaac cttctcagtc tctgtctctc      60
acctgctctg tcactggcta ctccatcacc agtggttttt actggacctg gatccggcag     120
tttccaggca acaaattgga atggatgggc ttcataagct acgatggtag caataactac     180
aacccatctc tcaaaaatcg aatctccatc actcgtgaca catctaagaa ccagttttc      240 ctgaagttga attctgtgac tactgaggac acagccacat attactgtgc aagaggcgga     300
ggctactatg gtaacctctt tgactactgg ggccaaggca ccactctcac agtctcg       357

<210> SEQ ID NO 14
<211> LENGTH: 119
<212> TYPE: PRT
<213> ORGANISM: Mus musculus
<220> FEATURE:
<221> NAME/KEY: MISC_FEATURE
<223> OTHER INFORMATION: Ab 5038 VH

<400> SEQUENCE: 14

Glu Val Lys Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Phe Tyr Trp Thr Trp Ile Arg Gln Phe Pro Gly Asn Lys Leu Glu Trp
        35                  40                  45

Met Gly Phe Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Gly Gly Gly Tyr Tyr Gly Asn Leu Phe Asp Tyr Trp Gly Gln
            100                 105                 110

Gly Thr Thr Leu Thr Val Ser
        115

<210> SEQ ID NO 15
<211> LENGTH: 649
<212> TYPE: DNA
<213> ORGANISM: Mus musculus
<220> FEATURE:
<221> NAME/KEY: misc_feature
<223> OTHER INFORMATION: Ab 5038 LC DNA

<400> SEQUENCE: 15
```

-continued

```
gatattgtga tgactcaaac tacatcctcc ctgtccgcct ctctgggaga cagagtcacc    60
atcagttgca ggccaagtca ggacattagc aattatgtaa actggtttca gcagaaacca   120
ggtggaactg ttaagctcct gatcttccac acatcaagat tacactcagg agtcccatca   180
aggttcagtg gcagtgggtc tggaacagat tattctctca ccattagcac cctggaacag   240
gaagatattg ccatttactt ttgccaacag ggtattacgc ttccgtggac gttcggtggc   300
ggcaccaagc tggaaataaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttaataag             649
```

<210> SEQ ID NO 16
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 5038 LC

<400> SEQUENCE: 16

```
Asp Ile Val Met Thr Gln Thr Thr Ser Ser Leu Ser Ala Ser Leu Gly
 1               5                  10                  15

Asp Arg Val Thr Ile Ser Cys Arg Pro Ser Gln Asp Ile Ser Asn Tyr
             20                  25                  30

Val Asn Trp Phe Gln Gln Lys Pro Gly Gly Thr Val Lys Leu Leu Ile
         35                  40                  45

Phe His Thr Ser Arg Leu His Ser Gly Val Pro Ser Arg Phe Ser Gly
     50                  55                  60

Ser Gly Ser Gly Thr Asp Tyr Ser Leu Thr Ile Ser Thr Leu Glu Gln
 65                  70                  75                  80

Glu Asp Ile Ala Ile Tyr Phe Cys Gln Gln Gly Ile Thr Leu Pro Trp
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 351

```
<212> TYPE: DNA
<213> ORGANISM: Mus musculus
<220> FEATURE:
<221> NAME/KEY: misc_feature
<223> OTHER INFORMATION: Ab 5082 VH DNA

<400> SEQUENCE: 17
gaggtgcagc tgaaggagtc aggacctggc ctcgtgaaac cttctcagtc tctgtctctc     60
acctgctctg tcaccggcta ctccatcacc agtgcttatt actggaactg gatccggcag    120
tttccaggaa acaaagtgga atggatgggc tacataggct acgatggtcg taatacctac    180
aacccatctc tcaaaaatcg aatctccatc actcgtgaca catctaagaa ccagtttttc    240
ctgaaattga attctctgac tactgaggac acagccacat attattgttc aagagagggg    300
gactacggtt actctgacta ctggggccaa ggcaccactc tcacagtctc g             351

<210> SEQ ID NO 18
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 5082 VH

<400> SEQUENCE: 18
```

Glu Val Gln Leu Lys Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Val Glu Trp
        35                  40                  45

Met Gly Tyr Ile Gly Tyr Asp Gly Arg Asn Thr Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Leu Thr Thr Glu Asp Thr Ala Thr Tyr Tyr Cys
                85                  90                  95

Ser Arg Glu Gly Asp Tyr Gly Tyr Ser Asp Tyr Trp Gly Gln Gly Thr
            100                 105                 110

Thr Leu Thr Val Ser
        115

```
<210> SEQ ID NO 19
<211> LENGTH: 649
<212> TYPE: DNA
<213> ORGANISM: Mus musculus
<220> FEATURE:
<221> NAME/KEY: misc_feature
<223> OTHER INFORMATION: Ab 5082 LC DNA

<400> SEQUENCE: 19
gatattgtga tgacgcaagc tacatcctcc ctgtctgcct ctctgggaga cagagtcacc     60
gtcagttgca gggcaagtca ggacattaac aattatttaa attggtatca gcagaagcca    120
gatggaactg ttaaactcct gatctactac acatcaagat acagtcagg agtcccatca     180 aggttcagtg gcagtgggtc tggaatagat tattctctca ccattagcaa cctggagcag    240
gaagattttg tcacttactt ttgccaacag agtgaaacgc ttccgtggac gttcggtgga    300
ggcaccaagc tggagctgaa acgaactgtg gctgcaccat ctgtcttcat cttcccgcca    360
tctgatgagc agttgaaatc tggaactgcc tctgttgtgt gcctgctgaa taacttctat    420
```

```
cccagagagg ccaaagtaca gtggaaggtg gataacgccc tccaatcggg taactcccag      480
gagagtgtca cagagcagga cagcaaggac agcacctaca gcctcagcag cacccctgacg     540 ctgagcaaag cagactacga gaaacacaaa gtctacgcct gcgaagtcac ccatcagggc      600
ctgagctcgc ccgtcacaaa gagcttcaac aggggagagt gttaataag                 649
```

```
<210> SEQ ID NO 20
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 5082 LC

<400> SEQUENCE: 20
```

Asp Ile Val Met Thr Gln Ala Thr Ser Ser Leu Ser Ala Ser Leu Gly
1               5                   10                  15

Asp Arg Val Thr Val Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Ile Asp Tyr Ser Leu Thr Ile Ser Asn Leu Glu Gln
65                  70                  75                  80

Glu Asp Phe Val Thr Tyr Phe Cys Gln Gln Ser Glu Thr Leu Pro Trp
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 21
<211> LENGTH: 339
<212> TYPE: DNA
<213> ORGANISM: Mus musculus
<220> FEATURE:
<221> NAME/KEY: misc_feature
<223> OTHER INFORMATION: Ab 5101 VH DNA

<400> SEQUENCE: 21
gaagtgaagc ttgttgagtc tggggagggc ctagtgaagc ctggagggtc cctgaaactc      60
tcctgtgcag cctctggatt cactttcagt agctatggca tgtcttgggt tcgccagact     120
ccggaaaaga ggctggagtg ggtcgcaacc attcgtgatg gtggaggtta cacctactat     180
```

```
tcagacaatg taaagggccg attcaccatc tccagggaca atgcccagaa caatctgtat    240
ttgcaaatga gccatctgaa gtctgaggac acagccatgt attactgtgc aagaggtata    300
ttggactact ggggtcaagg aacctcagtc accgtctcg                          339
```

```
<210> SEQ ID NO 22
<211> LENGTH: 113
<212> TYPE: PRT
<213> ORGANISM: Mus musculus
<220> FEATURE:
<221> NAME/KEY: MISC_FEATURE
<223> OTHER INFORMATION: Ab 5101 VH

<400> SEQUENCE: 22
```

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Arg Asp Gly Gly Tyr Thr Tyr Tyr Ser Asp Asn Val
    50                  55                  60

Lys Gly Arg Phe Thr Ile Ser Arg Asp Asn Ala Gln Asn Asn Leu Tyr
65                  70                  75                  80

Leu Gln Met Ser His Leu Lys Ser Glu Asp Thr Ala Met Tyr Tyr Cys
                85                  90                  95

Ala Arg Gly Ile Leu Asp Tyr Trp Gly Gln Gly Thr Ser Val Thr Val
            100                 105                 110

Ser
```

```
<210> SEQ ID NO 23
<211> LENGTH: 649
<212> TYPE: DNA
<213> ORGANISM: Mus musculus
<220> FEATURE:
<221> NAME/KEY: misc_feature
<223> OTHER INFORMATION: Ab 5101 LC DNA

<400> SEQUENCE: 23
```

```
caaattgttc tgacccagtc tccatcctcc ctgtctgcct ctctgggaga cagagtcacc    60
atcagttgca gggcaagtca ggacattagc aattatttaa actggtttca gcagagacca    120
gatggaactg ttaaactcct gatctactac acatcaagat acactcagg agtcccatca    180 aggttcagtg gcagtgggtc tggaacagat tattctctca ccattagcaa cctggagcaa    240
gaagatattg ccacttactt ttgccaacag gtaatacgc ttccgtacac gttcggaggg    300
gggaccaagc tggagctgaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac agggagagt gttaataag              649
```

```
<210> SEQ ID NO 24
<211> LENGTH: 214
<212> TYPE: PRT
<213> ORGANISM: Mus musculus
<220> FEATURE:
```

<221> NAME/KEY: MISC_FEATURE
<223> OTHER INFORMATION: Ab 5101 LC

<400> SEQUENCE: 24

Gln Ile Val Leu Thr Gln Ser Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Phe Gln Gln Arg Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 339
<212> TYPE: DNA
<213> ORGANISM: Mus musculus
<220> FEATURE:
<221> NAME/KEY: misc_feature
<223> OTHER INFORMATION: Ab 5106 VH DNA

<400> SEQUENCE: 25
gaagtgaagc tggttgagtc tgggggagac ttagtgaagc tggagagtc cctgaaactc      60 tcctgtgcag cctctggatt cactttcagt agctttgcca tgtcttgggt tcgccagact    120
ccggaaaaga ggctggaatg ggtcgcaacc attagtgatg gtggtagtca tctttactat    180
ccggacaatg taaagggccg attcaccatc tccagagaca atgccaagaa taacctgtac    240
ctgcagatga gccatctgaa gtctgaggac acagccatgt attactgtgc aagaggtatt    300
ttggactact ggggtcaagg aacctcagtc accgtctcg                          339

<210> SEQ ID NO 26
<211> LENGTH: 113
<212> TYPE: PRT
<213> ORGANISM: Mus musculus
<220> FEATURE:
<221> NAME/KEY: MISC_FEATURE
<223> OTHER INFORMATION: Ab 5106 VH -continued

<400> SEQUENCE: 26

Glu Val Lys Leu Val Glu Ser Gly Gly Asp Leu Val Lys Pro Gly Glu
1               5                   10                  15

Ser Leu Lys Leu Ser Cys Ala Ala Ser Gly Phe Thr Phe Ser Ser Phe
            20                  25                  30

Ala Met Ser Trp Val Arg Gln Thr Pro Glu Lys Arg Leu Glu Trp Val
        35                  40                  45

Ala Thr Ile Ser Asp Gly Gly Ser His Leu Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Gly Ile Leu Asp Tyr Trp Gly Gln Gly Thr Ser Val Thr Val
            100                 105                 110

Ser

<210> SEQ ID NO 27
<211> LENGTH: 649
<212> TYPE: DNA
<213> ORGANISM: Mus musculus
<220> FEATURE:
<221> NAME/KEY: misc_feature
<223> OTHER INFORMATION: Ab 5106 LC DNA

<400> SEQUENCE: 27
gatattgtga tgactcaagc tacatcctcc ctgtctgcct ctctgggaga cagagtcacc      60
atcagttgca gtgcaagtca ggacattaac aattatttaa actggtatca gcagaaacca     120
gatggaacta ttaaactcct gatctattac acatcaagtt tacactcagg agtcccatca     180
aggttcagtg gcagtgggtc tgggacagat tattctctca ccatcagcaa cctggaacct     240
gaagatattg ccacttacta ttgtcagcag tatagtagga ttccgtacac gttcggaggg     300
gggaccaagc tggaaataaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttaataag                 649

<210> SEQ ID NO 28
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab 5106 LC

<400> SEQUENCE: 28

Asp Ile Val Met Thr Gln Ala Thr Ser Ser Leu Ser Ala Ser Leu Gly
1               5                   10                  15

Asp Arg Val Thr Ile Ser Cys Ser Ala Ser Gln Asp Ile Asn Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly

```
            50                  55                  60
Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Arg Ile Pro Tyr
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 29
<211> LENGTH: 354
<212> TYPE: DNA
<213> ORGANISM: Mus musculus
<220> FEATURE:
<221> NAME/KEY: misc_feature
<223> OTHER INFORMATION: Ab 5143 VH DNA

<400> SEQUENCE: 29

```
caggtccaac tgcaacagtc tggacctgaa ctggtgaagc ctggggcttc agtgaagata    60
tcctgcaagg cttctggcta cagcttcaca agctactata cattgggt gaagcagagg    120 cctggacagg gacttgagtg gattggatgg atttatcctg gaagtggtca tactaagtac    180
aatgagaagt tcaagggcaa ggccacactg acggcagaca tcctccag cactgcctac    240 atgcagctca gcagcctaac atctgaggac tctgcggtct attactgtgc aagacctccc    300
tactatagta actacgccga tgtctggggc acagggacca cggtcaccgt ctcg         354
```

<210> SEQ ID NO 30
<211> LENGTH: 118
<212> TYPE: PRT
<213> ORGANISM: Mus musculus
<220> FEATURE:
<221> NAME/KEY: MISC_FEATURE
<223> OTHER INFORMATION: Ab 5143 VH

<400> SEQUENCE: 30

```
Gln Val Gln Leu Gln Gln Ser Gly Pro Glu Leu Val Lys Pro Gly Ala
  1               5                  10                  15

Ser Val Lys Ile Ser Cys Lys Ala Ser Gly Tyr Ser Phe Thr Ser Tyr
             20                  25                  30

Tyr Ile His Trp Val Lys Gln Arg Pro Gly Gln Gly Leu Glu Trp Ile
         35                  40                  45

Gly Trp Ile Tyr Pro Gly Ser Gly His Thr Lys Tyr Asn Glu Lys Phe
     50                  55                  60

Lys Gly Lys Ala Thr Leu Thr Ala Asp Thr Ser Ser Ser Thr Ala Tyr
```

```
                65                  70                  75                  80
Met Gln Leu Ser Ser Leu Thr Ser Glu Asp Ser Ala Val Tyr Tyr Cys
                    85                  90                  95

Ala Arg Pro Pro Tyr Tyr Ser Asn Tyr Ala Asp Val Trp Gly Thr Gly
                100                 105                 110

Thr Thr Val Thr Val Ser
            115

<210> SEQ ID NO 31
<211> LENGTH: 667
<212> TYPE: DNA
<213> ORGANISM: Mus musculus
<220> FEATURE:
<221> NAME/KEY: misc_feature
<223> OTHER INFORMATION: Ab 5143 LC DNA

<400> SEQUENCE: 31
gacattgtga tgacacagtc tccatcctcc ctgactgtga cagcaggaga gaaggtcact      60
atgagctgca agtccagtca gagtctgtta aacagtggaa atcaaaagaa ctacatgacc     120
tggtatcagc agaaaccagg gcagtctcct aaactgttga tctactgggc atccactagg    180
gaatctgggg tccctgatcg cttcacgggc agtggatctg gaacagattt cactctcacc    240
atcagcagtg tgcaggctga agacctggca gtttattact gtcagaatga ttatagttat    300
ccgtacacgt tcggaggggg gaccaagctg gagctgaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
taataag                                                               667

<210> SEQ ID NO 32
<211> LENGTH: 220
<212> TYPE: PRT
<213> ORGANISM: Mus musculus
<220> FEATURE:
<221> NAME/KEY: MISC_FEATURE
<223> OTHER INFORMATION: Ab 5143 LC

<400> SEQUENCE: 32

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Met Thr Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Tyr Thr Phe Gly Gly Gly Thr Lys Leu Glu Leu
                100                 105                 110

Lys Arg Thr Val Ala Ala Pro Ser Val Phe Ile Phe Pro Pro Ser Asp
```

```
            115                 120                 125
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 33
<211> LENGTH: 351
<212> TYPE: DNA
<213> ORGANISM: Mus musculus
<220> FEATURE:
<221> NAME/KEY: misc_feature
<223> OTHER INFORMATION: Ab 5144 VH DNA

<400> SEQUENCE: 33

```
caggtgcagc ttaaggagtc aggacctggc ctggtggcac cctcacagag cctgtccatc    60
acatgcactg tctctgggtt ctcattatcc agatatagtg tacactgggt tcgccagcct   120
ccaggaaagg gtctggagtg gctgggaatg atatggggtg gtggaagcac agactataat   180
tcagctctca aatccagact gaacatcaac aaggacaact ccaagagcca gttttttttt   240
aaaatgaaca gtctgcaaac tgatgacaca gccatgtact actgtgtcag aaaagggatt   300
acgacgacgg ggtttgacta ctggggccaa ggcaccactc tcacagtctc g            351
```

<210> SEQ ID NO 34
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 5144 VH

<400> SEQUENCE: 34

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Asn Ile Asn Lys Asp Asn Ser Lys Ser Gln Val Phe Phe
65                  70                  75                  80

Lys Met Asn Ser Leu Gln Thr Asp Asp Thr Ala Met Tyr Tyr Cys Val
                85                  90                  95

Arg Lys Gly Ile Thr Thr Thr Gly Phe Asp Tyr Trp Gly Gln Gly Thr
            100                 105                 110

Thr Leu Thr Val Ser
        115
```

```
<210> SEQ ID NO 35
<211> LENGTH: 646
<212> TYPE: DNA
<213> ORGANISM: Mus musculus
<220> FEATURE:
<221> NAME/KEY: misc_feature
<223> OTHER INFORMATION: Ab 5144 LC DNA

<400> SEQUENCE: 35
cacattgtgc tgacccagtc tccagcaatc atgtctgcat ctccagggga gaaggtcacc      60
atgacctgca gtgccagctc aagtgtaagt tacatgtact ggtaccaaca gaagccacga     120
tcctccccca gactcctgat ttatgacaca tccaacctgg cttctggagt ccctgttcgc     180
ttcagtggca gtgggtctgg gacctcttac tctctcacaa tcagccgaat ggaggctgac     240
gatgctgcca cttattactg ccagcagttg agtagttacc cacccacgtt cggaggggg      300 accaagctgg agctgaaacg aactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt aataag              646

<210> SEQ ID NO 36
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab 5144 LC

<400> SEQUENCE: 36

His Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Arg Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Asp
65                  70                  75                  80

Asp Ala Ala Thr Tyr Tyr Cys Gln Gln Leu Ser Ser Tyr Pro Pro Thr
                85                  90                  95

Phe Gly Gly Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

Cys Glu Val Thr His Gln Gly Leu Ser Ser Pro Val Thr Lys Ser Phe
            195                 200                 205

Asn Arg Gly Glu Cys
    210

<210> SEQ ID NO 37
<211> LENGTH: 351
<212> TYPE: DNA
<213> ORGANISM: Mus musculus
<220> FEATURE:
<221> NAME/KEY: misc_feature
<223> OTHER INFORMATION: Ab 5259 VH DNA

<400> SEQUENCE: 37
gaggtgcagc ttgtggagtc aggacctggc ctggtggcac cctcacagag cctgtccatc      60
acatgcactg tctctgggtt ctcattatcc agatatacta tccactgggt tcgccagcct     120
ccaggaaagg gtctggagtg gctgggaatg atatggggtg gtggaagcac agactataat     180
tcagctctca aatccagact gagcatcagc aaggacaact ccaagagcca acttttctta     240
aaaatgaaca gtctgcagac tgatgacaca gccatttact actgtgccag aaaagggatt     300
acgacgacgg ggtttgacta ctggggccaa ggcaccactc tcacagtctc g              351

<210> SEQ ID NO 38
<211> LENGTH: 117
<212> TYPE: PRT
<213> ORGANISM: Mus musculus
<220> FEATURE:
<221> NAME/KEY: MISC_FEATURE
<223> OTHER INFORMATION: Ab 5259 VH

<400> SEQUENCE: 38

Glu Val Gln Leu Val Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Thr Ile His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Leu Phe Leu
65                  70                  75                  80

Lys Met Asn Ser Leu Gln Thr Asp Asp Thr Ala Ile Tyr Tyr Cys Ala
                85                  90                  95

Arg Lys Gly Ile Thr Thr Thr Gly Phe Asp Tyr Trp Gly Gln Gly Thr
            100                 105                 110

Thr Leu Thr Val Ser
        115

<210> SEQ ID NO 39
<211> LENGTH: 646
<212> TYPE: DNA
<213> ORGANISM: Mus musculus
<220> FEATURE:
<221> NAME/KEY: misc_feature
<223> OTHER INFORMATION: Ab 5259 LC DNA

<400> SEQUENCE: 39
aacattgtgc tgacacagtc tccagcaatc atgtctgcat ctccagggga gaaggtcacc      60
atgacctgca gtgccagctc aagtgtaagt tacatgttct ggtaccagca gaagccagga     120

```
tcctcccca gactcctgat ttatgacaca tccaacctgg cttctggagt ccctgttcgc       180
ttcagtggca gtgggtctgg gacctcttac tctctcacaa tcagccgaat ggaggctgaa       240
gatgctgcca cttattactg ccagcagttg aatagttatc acccacgttt cggagggggg       300
accaagctgg aaataaaacg aactgtggct gcaccatctg tcttcatctt cccgccatct       360
gatgagcagt tgaaatctgg aactgcctct gttgtgtgcc tgctgaataa cttctatccc       420
agagaggcca agtacagtg gaaggtggat aacgccctcc aatcgggtaa ctcccaggag        480
agtgtcacag agcaggacag caaggacagc acctacagcc tcagcagcac cctgacgctg       540
agcaaagcag actacgagaa acacaaagtc tacgcctgcg aagtcaccca tcagggcctg       600
agctcgcccg tcacaaagag cttcaacagg ggagagtgtt aataag                     646
```

<210> SEQ ID NO 40
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab 5259 LC

<400> SEQUENCE: 40

```
Asn Ile Val Leu Thr Gln Ser Pro Ala Ile Met Ser Ala Ser Pro Gly
1               5                   10                  15
Glu Lys Val Thr Met Thr Cys Ser Ala Ser Ser Val Ser Tyr Met
            20                  25                  30
Phe Trp Tyr Gln Gln Lys Pro Gly Ser Ser Pro Arg Leu Leu Ile Tyr
        35                  40                  45
Asp Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Leu Asn Ser Tyr Pro Pro Thr
                85                  90                  95
Phe Gly Gly Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 41
<211> LENGTH: 320
<212> TYPE: DNA
<213> ORGANISM: Homo sapiens
<220> FEATURE:
<221> NAME/KEY: misc_feature
<223> OTHER INFORMATION: Human Ig kappa DNA

```
<220> FEATURE:
<221> NAME/KEY: exon
<222> LOCATION: (3)..(320)

<400> SEQUENCE: 41 ga act gtg gct gca cca tct gtc ttc atc ttc ccg cca tct gat gag        47
   Thr Val Ala Ala Pro Ser Val Phe Ile Phe Pro Pro Ser Asp Glu
   1               5                  10                  15 cag ttg aaa tct gga act gcc tct gtt gtg tgc ctg ctg aat aac ttc       95
Gln Leu Lys Ser Gly Thr Ala Ser Val Val Cys Leu Leu Asn Asn Phe
                20                  25                  30 tat ccc aga gag gcc aaa gta cag tgg aag gtg gat aac gcc ctc caa      143
Tyr Pro Arg Glu Ala Lys Val Gln Trp Lys Val Asp Asn Ala Leu Gln
            35                  40                  45 tcg ggt aac tcc cag gag agt gtc aca gag cag gac agc aag gac agc      191
Ser Gly Asn Ser Gln Glu Ser Val Thr Glu Gln Asp Ser Lys Asp Ser
        50                  55                  60 acc tac agc ctc agc agc acc ctg acg ctg agc aaa gca gac tac gag      239
Thr Tyr Ser Leu Ser Ser Thr Leu Thr Leu Ser Lys Ala Asp Tyr Glu
    65                  70                  75 aaa cac aaa gtc tac gcc tgc gaa gtc acc cat cag ggc ctg agc tcg      287
Lys His Lys Val Tyr Ala Cys Glu Val Thr His Gln Gly Leu Ser Ser
80                  85                  90                  95 ccc gtc aca aag agc ttc aac agg gga gag tgt                          320
Pro Val Thr Lys Ser Phe Asn Arg Gly Glu Cys
                100                 105

<210> SEQ ID NO 42
<211> LENGTH: 106
<212> TYPE: PRT
<213> ORGANISM: Homo sapiens
<220> FEATURE:
<221> NAME/KEY: Human Ig kappa constant region
<222> LOCATION: (1)..(106)

<400> SEQUENCE: 42

Thr Val Ala Ala Pro Ser Val Phe Ile Phe Pro Pro Ser Asp Glu Gln
1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 43
<211> LENGTH: 1602
<212> TYPE: DNA
<213> ORGANISM: Homo sapiens
<220> FEATURE:
<221> NAME/KEY: misc_feature
<223> OTHER INFORMATION: Human IGHG1 constant domain genomic sequence
<220> FEATURE:
<221> NAME/KEY: exon
<222> LOCATION: (1)..(298)
<220> FEATURE:
<221> NAME/KEY: exon
```

<222> LOCATION: (690)..(734)
<220> FEATURE:
<221> NAME/KEY: exon
<222> LOCATION: (853)..(1182)
<220> FEATURE:
<221> NAME/KEY: exon
<222> LOCATION: (1280)..(1602)

<400> SEQUENCE: 43

```
agt gcc tcc acc aag ggc cca tcg gtc ttc ccc ctg gca ccc tcc tcc        48
Ser Ala Ser Thr Lys Gly Pro Ser Val Phe Pro Leu Ala Pro Ser Ser
1               5                   10                  15 aag agc acc tct ggg ggc aca gcg gcc ctg ggc tgc ctg gtc aag gac        96
Lys Ser Thr Ser Gly Gly Thr Ala Ala Leu Gly Cys Leu Val Lys Asp
            20                  25                  30 tac ttc ccc gaa ccg gtg acg gtg tcg tgg aac tca ggc gcc ctg acc       144
Tyr Phe Pro Glu Pro Val Thr Val Ser Trp Asn Ser Gly Ala Leu Thr
        35                  40                  45 agc ggc gtg cac acc ttc ccg gct gtc cta cag tcc tca gga ctc tac       192
Ser Gly Val His Thr Phe Pro Ala Val Leu Gln Ser Ser Gly Leu Tyr
    50                  55                  60 tcc ctc agc agc gtg gtg acc gtg ccc tcc agc agc ttg ggc acc cag       240
Ser Leu Ser Ser Val Val Thr Val Pro Ser Ser Ser Leu Gly Thr Gln
65                  70                  75                  80 acc tac atc tgc aac gtg aat cac aag ccc agc aac acc aag gtg gac       288
Thr Tyr Ile Cys Asn Val Asn His Lys Pro Ser Asn Thr Lys Val Asp
                85                  90                  95 aag aga gtt g gtgagaggcc agcacaggga gggagggtgt ctgctggaag              338
Lys Arg Val ccaggctcag cgctcctgcc tggacgcatc ccggctatgc agtcccagtc cagggcagca     398
aggcaggccc cgtctgcctc ttcacccgga ggcctctgcc cgccccactc atgctcaggg     458
agagggtctt ctggcttttt ccccaggctc tgggcaggca caggctaggt gcccctaacc     518
caggccctgc acacaaaggg gcaggtgctg ggctcagacc tgccaagagc catatccggg     578
aggaccctgc ccctgaccta agcccacccc aaaggccaaa ctctccactc cctcagctcg     638
gacaccttct ctcctcccag attccagtaa ctcccaatct tctctctgca g ag  ccc      694
                                                         Glu Pro
                                                         100 aaa tct tgt gac aaa act cac aca tgc cca ccg tgc cca g gtaagccagc     744
Lys Ser Cys Asp Lys Thr His Thr Cys Pro Pro Cys Pro
            105                 110 ccaggcctcg ccctccagct caaggcggga caggtgccct agagtagcct gcatccaggg     804
acaggcccca gccgggtgct gacacgtcca cctccatctc ttcctcag ca  cct gaa      860
                                                     Ala Pro Glu
                                                     115 ctc ctg ggg gga ccg tca gtc ttc ctc ttc ccc cca aaa ccc aag gac       908
Leu Leu Gly Gly Pro Ser Val Phe Leu Phe Pro Pro Lys Pro Lys Asp
        120                 125                 130 acc ctc atg atc tcc cgg acc cct gag gtc aca tgc gtg gtg gtg gac       956
Thr Leu Met Ile Ser Arg Thr Pro Glu Val Thr Cys Val Val Val Asp
    135                 140                 145 gtg agc cac gaa gac cct gag gtc aag ttc aac tgg tac gtg gac ggc      1004
Val Ser His Glu Asp Pro Glu Val Lys Phe Asn Trp Tyr Val Asp Gly
150                 155                 160                 165 gtg gag gtg cat aat gcc aag aca aag ccg cgg gag gag cag tac aac      1052
Val Glu Val His Asn Ala Lys Thr Lys Pro Arg Glu Glu Gln Tyr Asn
                170                 175                 180 agc acg tac cgt gtg gtc agc gtc ctc acc gtc ctg cac cag gac tgg      1100
Ser Thr Tyr Arg Val Val Ser Val Leu Thr Val Leu His Gln Asp Trp
```

```
                           185                 190                      195
ctg aat ggc aag gag tac aag tgc aag gtc tcc aac aaa gcc ctc cca            1148
Leu Asn Gly Lys Glu Tyr Lys Cys Lys Val Ser Asn Lys Ala Leu Pro
            200                 205                  210 gcc ccc atc gag aaa acc atc tcc aaa gcc aaa g gtgggacccg                   1192
Ala Pro Ile Glu Lys Thr Ile Ser Lys Ala Lys
            215                 220 tggggtgcga gggccacatg gacagaggcc ggctcggccc accctctgcc ctgagagtga          1252
ccgctgtacc aacctctgtc cctacag gg  cag ccc cga gaa cca cag gtg tac          1305
                                 Gly Gln Pro Arg Glu Pro Gln Val Tyr
                                         225                 230 acc ctg ccc cca tcc cgg gag gag atg acc aag aac cag gtc agc ctg            1353
Thr Leu Pro Pro Ser Arg Glu Glu Met Thr Lys Asn Gln Val Ser Leu
        235                 240                 245 acc tgc ctg gtc aaa ggc ttc tat ccc agc gac atc gcc gtg gag tgg            1401
Thr Cys Leu Val Lys Gly Phe Tyr Pro Ser Asp Ile Ala Val Glu Trp
250                 255                 260                 265 gag agc aat ggg cag ccg gag aac aac tac aag acc acg cct ccc gtg            1449
Glu Ser Asn Gly Gln Pro Glu Asn Asn Tyr Lys Thr Thr Pro Pro Val
                270                 275                 280 ctg gac tcc gac ggc tcc ttc ttc ctc tat agc aag ctc acc gtg gac            1497
Leu Asp Ser Asp Gly Ser Phe Phe Leu Tyr Ser Lys Leu Thr Val Asp
            285                 290                 295 aag agc agg tgg cag cag ggg aac gtc ttc tca tgc tcc gtg atg cat            1545
Lys Ser Arg Trp Gln Gln Gly Asn Val Phe Ser Cys Ser Val Met His
        300                 305                 310 gag gct ctg cac aac cac tac acg cag aag agc ctc tcc ctg tcc ccg            1593
Glu Ala Leu His Asn His Tyr Thr Gln Lys Ser Leu Ser Leu Ser Pro
    315                 320                 325 ggt aaa tga                                                                1602
Gly Lys
330

<210> SEQ ID NO 44
<211> LENGTH: 331
<212> TYPE: PRT
<213> ORGANISM: Homo sapiens
<220> FEATURE:
<221> NAME/KEY: MISC_FEATURE
<223> OTHER INFORMATION: Human IGHG1 constant region

<400> SEQUENCE: 44

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125
```

```
Pro Lys Pro Lys Asp Thr Leu Met Ile Ser Arg Thr Pro Glu Val Thr
    130                 135                 140
Cys Val Val Asp Val Ser His Glu Asp Pro Glu Val Lys Phe Asn
145                 150                 155                 160
Trp Tyr Val Asp Gly Val Glu Val His Asn Ala Lys Thr Lys Pro Arg
                165                 170                 175
Glu Glu Gln Tyr Asn Ser Thr Tyr Arg Val Val Ser Val Leu Thr Val
            180                 185                 190
Leu His Gln Asp Trp Leu Asn Gly Lys Glu Tyr Lys Cys Lys Val Ser
        195                 200                 205
Asn Lys Ala Leu Pro Ala Pro Ile Glu Lys Thr Ile Ser Lys Ala Lys
210                 215                 220
Gly Gln Pro Arg Glu Pro Gln Val Tyr Thr Leu Pro Pro Ser Arg Glu
225                 230                 235                 240
Glu Met Thr Lys Asn Gln Val Ser Leu Thr Cys Leu Val Lys Gly Phe
                245                 250                 255
Tyr Pro Ser Asp Ile Ala Val Glu Trp Glu Ser Asn Gly Gln Pro Glu
            260                 265                 270
Asn Asn Tyr Lys Thr Thr Pro Pro Val Leu Asp Ser Asp Gly Ser Phe
        275                 280                 285
Phe Leu Tyr Ser Lys Leu Thr Val Asp Lys Ser Arg Trp Gln Gln Gly
290                 295                 300
Asn Val Phe Ser Cys Ser Val Met His Glu Ala Leu His Asn His Tyr
305                 310                 315                 320
Thr Gln Lys Ser Leu Ser Leu Ser Pro Gly Lys
                325                 330

<210> SEQ ID NO 45
<211> LENGTH: 8
<212> TYPE: PRT
<213> ORGANISM: Mus musculus
<220> FEATURE:
<221> NAME/KEY: MISC_FEATURE
<223> OTHER INFORMATION: 4785/5143 HCDR1

<400> SEQUENCE: 45

Gly Tyr Ser Phe Thr Ser Tyr Tyr
1               5

<210> SEQ ID NO 46
<211> LENGTH: 8
<212> TYPE: PRT
<213> ORGANISM: Mus musculus
<220> FEATURE:
<221> NAME/KEY: MISC_FEATURE
<223> OTHER INFORMATION: 4785/5143 HCDR2

<400> SEQUENCE: 46

Ile Tyr Pro Gly Ser Gly His Thr
1               5

<210> SEQ ID NO 47
<211> LENGTH: 14
<212> TYPE: PRT
<213> ORGANISM: Mus musculus
<220> FEATURE:
<221> NAME/KEY: MISC_FEATURE
<223> OTHER INFORMATION: 4785/5143 HCDR3

<400> SEQUENCE: 47

Cys Ala Arg Pro Pro Tyr Tyr Ser Asn Tyr Ala Asp Val Trp
```

<210> SEQ ID NO 48
<211> LENGTH: 9
<212> TYPE: PRT
<213> ORGANISM: Mus musculus
<220> FEATURE:
<221> NAME/KEY: MISC_FEATURE
<223> OTHER INFORMATION: 4889/5082 HCDR1

<400> SEQUENCE: 48

Gly Tyr Ser Ile Thr Ser Ala Tyr Tyr
1               5

<210> SEQ ID NO 49
<211> LENGTH: 7
<212> TYPE: PRT
<213> ORGANISM: Mus musculus
<220> FEATURE:
<221> NAME/KEY: MISC_FEATURE
<223> OTHER INFORMATION: 4889 HCDR2

<400> SEQUENCE: 49

Val Ser Tyr Asp Gly Ser Asn
1               5

<210> SEQ ID NO 50
<211> LENGTH: 13
<212> TYPE: PRT
<213> ORGANISM: Mus musculus
<220> FEATURE:
<221> NAME/KEY: MISC_FEATURE
<223> OTHER INFORMATION: 4889 HCDR3

<400> SEQUENCE: 50

Cys Ala Arg Glu Gly Asp Tyr Gly Tyr Ser Asp Tyr Trp
1               5                   10

<210> SEQ ID NO 51
<211> LENGTH: 8
<212> TYPE: PRT
<213> ORGANISM: Mus musculus
<220> FEATURE:
<221> NAME/KEY: MISC_FEATURE
<223> OTHER INFORMATION: 4935 HCDR1

<400> SEQUENCE: 51

Gly Tyr Thr Phe Thr Ser Tyr Tyr
1               5

<210> SEQ ID NO 52
<211> LENGTH: 8
<212> TYPE: PRT
<213> ORGANISM: Mus musculus
<220> FEATURE:
<221> NAME/KEY: MISC_FEATURE
<223> OTHER INFORMATION: 4935 HCDR2

<400> SEQUENCE: 52

Ile Tyr Pro Gly Asn Val His Thr
1               5

<210> SEQ ID NO 53
<211> LENGTH: 15
<212> TYPE: PRT
<213> ORGANISM: Mus musculus
<220> FEATURE:
<221> NAME/KEY: MISC_FEATURE

```
<223> OTHER INFORMATION: 4935 HCDR3

<400> SEQUENCE: 53

Cys Val Arg Arg Tyr Gly Tyr Asp Gly Asp Trp Phe Ala Tyr Trp
1               5                   10                  15

<210> SEQ ID NO 54
<211> LENGTH: 9
<212> TYPE: PRT
<213> ORGANISM: Mus musculus
<220> FEATURE:
<221> NAME/KEY: MISC_FEATURE
<223> OTHER INFORMATION: 5038 HCDR1

<400> SEQUENCE: 54

Gly Tyr Ser Ile Thr Ser Gly Phe Tyr
1               5

<210> SEQ ID NO 55
<211> LENGTH: 7
<212> TYPE: PRT
<213> ORGANISM: Mus musculus
<220> FEATURE:
<221> NAME/KEY: MISC_FEATURE
<223> OTHER INFORMATION: 5038 HCDR2

<400> SEQUENCE: 55

Ile Ser Tyr Asp Gly Ser Asn
1               5

<210> SEQ ID NO 56
<211> LENGTH: 15
<212> TYPE: PRT
<213> ORGANISM: Mus musculus
<220> FEATURE:
<221> NAME/KEY: MISC_FEATURE
<223> OTHER INFORMATION: 5038 HCDR3

<400> SEQUENCE: 56

Cys Ala Arg Gly Gly Gly Tyr Tyr Gly Asn Leu Phe Asp Tyr Trp
1               5                   10                  15

<210> SEQ ID NO 57
<211> LENGTH: 7
<212> TYPE: PRT
<213> ORGANISM: Mus musculus
<220> FEATURE:
<221> NAME/KEY: MISC_FEATURE
<223> OTHER INFORMATION: 5082 HCDR2

<400> SEQUENCE: 57

Ile Gly Tyr Asp Gly Arg Asn
1               5

<210> SEQ ID NO 58
<211> LENGTH: 13
<212> TYPE: PRT
<213> ORGANISM: Mus musculus
<220> FEATURE:
<221> NAME/KEY: MISC_FEATURE
<223> OTHER INFORMATION: 5082 HCDR3

<400> SEQUENCE: 58

Cys Ser Arg Glu Gly Asp Tyr Gly Tyr Ser Asp Tyr Trp
1               5                   10

<210> SEQ ID NO 59
```

```
<211> LENGTH: 8
<212> TYPE: PRT
<213> ORGANISM: Mus musculus
<220> FEATURE:
<221> NAME/KEY: MISC_FEATURE
<223> OTHER INFORMATION: 5101 HCDR1

<400> SEQUENCE: 59

Gly Phe Thr Phe Ser Ser Tyr Gly
1               5

<210> SEQ ID NO 60
<211> LENGTH: 8
<212> TYPE: PRT
<213> ORGANISM: Mus musculus
<220> FEATURE:
<221> NAME/KEY: MISC_FEATURE
<223> OTHER INFORMATION: 5101 HCDR2

<400> SEQUENCE: 60

Ile Arg Asp Gly Gly Gly Tyr Thr
1               5

<210> SEQ ID NO 61
<211> LENGTH: 9
<212> TYPE: PRT
<213> ORGANISM: Mus musculus
<220> FEATURE:
<221> NAME/KEY: MISC_FEATURE
<223> OTHER INFORMATION: 5101/5106 HCDR3

<400> SEQUENCE: 61

Cys Ala Arg Gly Ile Leu Asp Tyr Trp
1               5

<210> SEQ ID NO 62
<211> LENGTH: 8
<212> TYPE: PRT
<213> ORGANISM: Mus musculus
<220> FEATURE:
<221> NAME/KEY: MISC_FEATURE
<223> OTHER INFORMATION: 5106 HCDR1

<400> SEQUENCE: 62

Gly Phe Thr Phe Ser Ser Phe Ala
1               5

<210> SEQ ID NO 63
<211> LENGTH: 8
<212> TYPE: PRT
<213> ORGANISM: Mus musculus
<220> FEATURE:
<221> NAME/KEY: MISC_FEATURE
<223> OTHER INFORMATION: 5106 HCDR2

<400> SEQUENCE: 63

Ile Ser Asp Gly Gly Ser His Leu
1               5

<210> SEQ ID NO 64
<211> LENGTH: 8
<212> TYPE: PRT
<213> ORGANISM: Mus musculus
<220> FEATURE:
<221> NAME/KEY: MISC_FEATURE
<223> OTHER INFORMATION: 5144 HCDR1

<400> SEQUENCE: 64
```

```
Gly Phe Ser Leu Ser Arg Tyr Ser
1               5

<210> SEQ ID NO 65
<211> LENGTH: 7
<212> TYPE: PRT
<213> ORGANISM: Mus musculus
<220> FEATURE:
<221> NAME/KEY: MISC_FEATURE
<223> OTHER INFORMATION: 5144/5259 HCDR2

<400> SEQUENCE: 65

Ile Trp Gly Gly Gly Ser Thr
1               5

<210> SEQ ID NO 66
<211> LENGTH: 14
<212> TYPE: PRT
<213> ORGANISM: Mus musculus
<220> FEATURE:
<221> NAME/KEY: MISC_FEATURE
<223> OTHER INFORMATION: 5144 HCDR3

<400> SEQUENCE: 66

Cys Val Arg Lys Gly Ile Thr Thr Thr Gly Phe Asp Tyr Trp
1               5                   10

<210> SEQ ID NO 67
<211> LENGTH: 8
<212> TYPE: PRT
<213> ORGANISM: Mus musculus
<220> FEATURE:
<221> NAME/KEY: MISC_FEATURE
<223> OTHER INFORMATION: 5259 HCDR1

<400> SEQUENCE: 67

Gly Phe Ser Leu Ser Arg Tyr Thr
1               5

<210> SEQ ID NO 68
<211> LENGTH: 14
<212> TYPE: PRT
<213> ORGANISM: Mus musculus
<220> FEATURE:
<221> NAME/KEY: MISC_FEATURE
<223> OTHER INFORMATION: 5259 HCDR3

<400> SEQUENCE: 68

Cys Ala Arg Lys Gly Ile Thr Thr Thr Gly Phe Asp Tyr Trp
1               5                   10

<210> SEQ ID NO 69
<211> LENGTH: 12
<212> TYPE: PRT
<213> ORGANISM: Mus musculus
<220> FEATURE:
<221> NAME/KEY: MISC_FEATURE
<223> OTHER INFORMATION: 4785/5143 LCDR1

<400> SEQUENCE: 69

Gln Ser Leu Leu Asn Ser Gly Asn Gln Lys Asn Tyr
1               5                   10

<210> SEQ ID NO 70
<211> LENGTH: 11
<212> TYPE: PRT
<213> ORGANISM: Mus musculus
<220> FEATURE:
```

<221> NAME/KEY: MISC_FEATURE
<223> OTHER INFORMATION: 4785 LCDR3

<400> SEQUENCE: 70

Cys Gln Ser Asp Tyr Ser Tyr Pro Tyr Thr Phe
1               5                   10

<210> SEQ ID NO 71
<211> LENGTH: 6
<212> TYPE: PRT
<213> ORGANISM: Mus musculus
<220> FEATURE:
<221> NAME/KEY: MISC_FEATURE
<223> OTHER INFORMATION: 4889/5038/5101 LCDR1

<400> SEQUENCE: 71

Gln Asp Ile Ser Asn Tyr
1               5

<210> SEQ ID NO 72
<211> LENGTH: 11
<212> TYPE: PRT
<213> ORGANISM: Mus musculus
<220> FEATURE:
<221> NAME/KEY: MISC_FEATURE
<223> OTHER INFORMATION: 4889 LCDR3

<400> SEQUENCE: 72

Cys Gln Gln Ser Asn Thr Leu Pro Trp Thr Phe
1               5                   10

<210> SEQ ID NO 73
<211> LENGTH: 10
<212> TYPE: PRT
<213> ORGANISM: Mus musculus
<220> FEATURE:
<221> NAME/KEY: MISC_FEATURE
<223> OTHER INFORMATION: 4935 LCDR1

<400> SEQUENCE: 73

Glu Ser Val Asp Ser Tyr Gly Asn Thr Phe
1               5                   10

<210> SEQ ID NO 74
<211> LENGTH: 11
<212> TYPE: PRT
<213> ORGANISM: Mus musculus
<220> FEATURE:
<221> NAME/KEY: MISC_FEATURE
<223> OTHER INFORMATION: 4935 LCDR3

<400> SEQUENCE: 74

Cys Gln Gln Ser Asn Glu Asp Pro Trp Thr Phe
1               5                   10

<210> SEQ ID NO 75
<211> LENGTH: 11
<212> TYPE: PRT
<213> ORGANISM: Mus musculus
<220> FEATURE:
<221> NAME/KEY: MISC_FEATURE
<223> OTHER INFORMATION: 5038 LCDR3

<400> SEQUENCE: 75

Cys Gln Gln Gly Ile Thr Leu Pro Trp Thr Phe
1               5                   10

```
<210> SEQ ID NO 76
<211> LENGTH: 6
<212> TYPE: PRT
<213> ORGANISM: Mus musculus
<220> FEATURE:
<221> NAME/KEY: MISC_FEATURE
<223> OTHER INFORMATION: 5082/5106 LCDR1

<400> SEQUENCE: 76

Gln Asp Ile Asn Asn Tyr
1               5

<210> SEQ ID NO 77
<211> LENGTH: 11
<212> TYPE: PRT
<213> ORGANISM: Mus musculus
<220> FEATURE:
<221> NAME/KEY: MISC_FEATURE
<223> OTHER INFORMATION: 5082 LCDR3

<400> SEQUENCE: 77

Cys Gln Gln Ser Glu Thr Leu Pro Trp Thr Phe
1               5                   10

<210> SEQ ID NO 78
<211> LENGTH: 11
<212> TYPE: PRT
<213> ORGANISM: Mus musculus
<220> FEATURE:
<221> NAME/KEY: MISC_FEATURE
<223> OTHER INFORMATION: 5101 LCDR3

<400> SEQUENCE: 78

Cys Gln Gln Gly Asn Thr Leu Pro Tyr Thr Phe
1               5                   10

<210> SEQ ID NO 79
<211> LENGTH: 11
<212> TYPE: PRT
<213> ORGANISM: Mus musculus
<220> FEATURE:
<221> NAME/KEY: MISC_FEATURE
<223> OTHER INFORMATION: 5106 LCDR3

<400> SEQUENCE: 79

Cys Gln Gln Tyr Ser Arg Ile Pro Tyr Thr Phe
1               5                   10

<210> SEQ ID NO 80
<211> LENGTH: 11
<212> TYPE: PRT
<213> ORGANISM: Mus musculus
<220> FEATURE:
<221> NAME/KEY: MISC_FEATURE
<223> OTHER INFORMATION: 5143 LCDR3

<400> SEQUENCE: 80

Cys Gln Asn Asp Tyr Ser Tyr Pro Tyr Thr Phe
1               5                   10

<210> SEQ ID NO 81
<211> LENGTH: 5
<212> TYPE: PRT
<213> ORGANISM: Mus musculus
<220> FEATURE:
<221> NAME/KEY: MISC_FEATURE
<223> OTHER INFORMATION: 5144/5259 LCDR1

<400> SEQUENCE: 81
```

```
Ser Ser Val Ser Tyr
1               5

<210> SEQ ID NO 82
<211> LENGTH: 11
<212> TYPE: PRT
<213> ORGANISM: Mus musculus
<220> FEATURE:
<221> NAME/KEY: MISC_FEATURE
<223> OTHER INFORMATION: 5144 LCDR3

<400> SEQUENCE: 82

Cys Gln Gln Leu Ser Ser Tyr Pro Pro Thr Phe
1               5                   10

<210> SEQ ID NO 83
<211> LENGTH: 11
<212> TYPE: PRT
<213> ORGANISM: Mus musculus
<220> FEATURE:
<221> NAME/KEY: MISC_FEATURE
<223> OTHER INFORMATION: 5259 LCDR3

<400> SEQUENCE: 83

Cys Gln Gln Leu Asn Ser Tyr Pro Pro Thr Phe
1               5                   10
```